(12) United States Patent
Nazzaro et al.

(10) Patent No.: US 11,129,943 B2
(45) Date of Patent: Sep. 28, 2021

(54) SINGLE DOSE DRUG DELIVERY DEVICE

(71) Applicant: Insulet Corporation, Acton, MA (US)

(72) Inventors: David Nazzaro, Groveland, MA (US);
Ian McLaughlin, Boxboro, MA (US);
Simon Kozin, Lexington, MA (US);
Maureen McCaffrey, Boston, MA (US); Jackie Mac, Malden, MA (US);
Alexander Doudoumopoulos, Los Angeles, CA (US); Bhavin Patel, Acton, MA (US)

(73) Assignee: INSULET CORPORATION, Acton, MA (US)

(*) Notice: Subject to any disclaimer, the term of this patent is extended or adjusted under 35 U.S.C. 154(b) by 571 days.

(21) Appl. No.: 15/980,469

(22) Filed: May 15, 2018

(65) Prior Publication Data
US 2018/0256823 A1 Sep. 13, 2018

Related U.S. Application Data

(63) Continuation of application No. 15/607,169, filed on May 26, 2017, now Pat. No. 10,342,926.
(Continued)

(51) Int. Cl.
A61M 5/315 (2006.01)
A61M 5/142 (2006.01)
(Continued)

(52) U.S. Cl.
CPC .... A61M 5/31593 (2013.01); A61M 5/14248 (2013.01); A61M 5/28 (2013.01);
(Continued)

(58) Field of Classification Search
CPC .......... A61M 5/31593; A61M 5/14248; A61M 2005/14252; A61M 5/31531;
(Continued)

(56) References Cited

U.S. PATENT DOCUMENTS

| 4,313,439 A | 2/1982 | Babb et al. |
| 4,898,578 A | 2/1990 | Rubalcaba |

(Continued)

FOREIGN PATENT DOCUMENTS

| WO | 200048112 A2 | 8/2000 |
| WO | 2001078812 A1 | 10/2001 |

(Continued)

OTHER PUBLICATIONS

International Search Report and Written Opinion for Application No. PCT/US17/61336, dated Jan. 25, 2018, 11 pages.

Primary Examiner — Theodore J Stigell
(74) Attorney, Agent, or Firm — Kacvinsky Daisak Bluni PLLC

(57) ABSTRACT

A wearable drug delivery device that can deliver a liquid drug stored in a container to a patient is provided. The container can be a prefilled cartridge that can be loaded into the drug delivery device by the patient or that can be preloaded within the drug delivery device when provided to the patient. A sealed end of the container is pierced to couple the stored liquid drug to a needle conduit that is coupled to a needle insertion component that provides access to the patient. A drive system of the drug delivery device can expel the liquid drug from the cartridge to the patient through the needle conduit. The drive system can be controlled to provide the liquid drug to the patient in a single dose or over multiple doses.

20 Claims, 41 Drawing Sheets

Related U.S. Application Data

(60) Provisional application No. 62/449,845, filed on Jan. 24, 2017, provisional application No. 62/449,849, filed on Jan. 24, 2017, provisional application No. 62/385,749, filed on Sep. 9, 2016, provisional application No. 62/375,026, filed on Aug. 15, 2016, provisional application No. 62/374,881, filed on Aug. 14, 2016, provisional application No. 62/374,394, filed on Aug. 12, 2016, provisional application No. 62/341,898, filed on May 26, 2016.

(51) Int. Cl.
*A61M 5/28* (2006.01)
*A61M 5/32* (2006.01)
*A61M 5/24* (2006.01)
*A61M 37/00* (2006.01)
*A61M 5/31* (2006.01)
*A61M 5/42* (2006.01)

(52) U.S. Cl.
CPC .......... *A61M 5/31531* (2013.01); *A61M 5/32* (2013.01); *A61M 5/42* (2013.01); *A61M 37/00* (2013.01); *A61M 2005/2474* (2013.01); *A61M 2005/3142* (2013.01); *A61M 2005/31518* (2013.01)

(58) Field of Classification Search
CPC .......... A61M 2005/31518; A61M 2005/3142; A61M 2005/2474; A61M 5/28; A61M 5/32; A61M 5/24; A61M 5/42
See application file for complete search history.

(56) References Cited

U.S. PATENT DOCUMENTS

| | | | |
|---|---|---|---|
| 5,189,609 A | 2/1993 | Tivig et al. | |
| 5,254,096 A | 10/1993 | Rondelet et al. | |
| 5,261,882 A | 11/1993 | Sealfon | |
| 5,858,239 A | 1/1999 | Kenley et al. | |
| 5,965,848 A | 10/1999 | Altschul et al. | |
| 6,474,219 B2 | 11/2002 | Klitmose et al. | |
| 6,595,956 B1 | 7/2003 | Gross et al. | |
| 7,771,391 B2 * | 8/2010 | Carter | A61M 5/1452 604/151 |
| 9,180,244 B2 | 11/2015 | Anderson et al. | |
| 9,192,716 B2 | 11/2015 | Jugl et al. | |
| 2002/0173769 A1 * | 11/2002 | Gray | A61M 39/14 604/506 |
| 2003/0040715 A1 | 2/2003 | D'Antonio et al. | |
| 2004/0069044 A1 | 4/2004 | Lavi et al. | |
| 2005/0182366 A1 | 8/2005 | Vogt et al. | |
| 2007/0100635 A1 | 5/2007 | Mahajan et al. | |
| 2007/0118405 A1 | 5/2007 | Campbell et al. | |
| 2008/0160492 A1 | 7/2008 | Campbell et al. | |
| 2010/0017141 A1 | 1/2010 | Campbell et al. | |
| 2010/0064243 A1 | 3/2010 | Buck et al. | |
| 2010/0077198 A1 | 3/2010 | Buck et al. | |
| 2010/0185183 A1 | 7/2010 | Alme et al. | |
| 2010/0241066 A1 | 9/2010 | Hansen et al. | |
| 2012/0150446 A1 | 6/2012 | Chang et al. | |
| 2012/0226259 A1 | 9/2012 | Yodfat et al. | |
| 2013/0172710 A1 | 7/2013 | Mears et al. | |
| 2013/0245545 A1 | 9/2013 | Arnold et al. | |
| 2014/0018730 A1 | 1/2014 | Muller-Pathle | |
| 2014/0032549 A1 | 1/2014 | McDaniel et al. | |
| 2017/0021096 A1 | 1/2017 | Cole et al. | |
| 2017/0239415 A1 | 8/2017 | Hwang et al. | |

FOREIGN PATENT DOCUMENTS

| | | |
|---|---|---|
| WO | 2002076535 A1 | 10/2002 |
| WO | 2011133823 A1 | 10/2011 |
| WO | 2015167201 A1 | 11/2015 |

\* cited by examiner

SINGLE DOSE DRUG DELIVERY DEVICE

CROSS-REFERENCE TO RELATED APPLICATIONS

This application is a Continuation of U.S. application Ser. No. 15/607,169, filed on May 26, 2017, which claims the benefit of U.S. Provisional Application No. 62/341,898, filed May 26, 2016, U.S. Provisional Application No. 62/374,394, filed Aug. 12, 2016, U.S. Provisional Application No. 62/374,881, filed Aug. 14, 2016, U.S. Provisional Application No. 62/375,026, filed Aug. 15, 2016, U.S. Provisional Application No. 62/385,749, filed Sep. 9, 2016, U.S. Provisional Application No. 62/449,845, filed Jan. 24, 2017, and U.S. Provisional Application No. 62/449,849, filed Jan. 24, 2017, each of which is incorporated herein by reference in its entirety.

TECHNICAL FIELD

Embodiments generally relate to medication delivery. More particularly, embodiments relate to wearable drug delivery devices.

BACKGROUND

Many conventional drug delivery systems, such as hand-held auto-injectors, are designed to rapidly delivery a drug to a patient. These conventional drug delivery systems are generally not suitable for delivering a drug to a user over relatively longer periods of time as may be required for many drugs.

As an alternative to conventional auto-injectors, many conventional drug delivery systems are designed to be wearable and to deliver a drug more slowly to the patient. However, these conventional wearable drug delivery systems often require a patient to transfer a drug or other medicine from a vial to a container within the drug delivery system. Transferring the drug can be a challenging task for many patients as it may require precise handling of the drug, a transfer mechanism (e.g., a syringe), and the drug delivery system. Some conventional wearable drug delivery systems use prefilled cartridges that contain the drug intended for the patient, obviating the need for such drug transfers. However, these conventional cartridge-based drug delivery systems are often bulky and cumbersome due to the included cartridge and can be uncomfortable when worn by the patient.

A need therefore exists for a more convenient and user-friendly wearable drug delivery device for providing a drug to a user.

DETAILED DESCRIPTION

This disclosure presents various systems, components, and methods for delivering a liquid drug or medicine to a patient or user. Each of the systems, components, and methods disclosed herein provides one or more advantages over conventional systems, components, and methods.

Various embodiments include a wearable drug delivery device that can deliver a liquid drug stored in a container to a patient or user. The container can be a prefilled cartridge that can be loaded into the drug delivery device by the patient or that can be preloaded within the drug delivery device when provided to the patient. A sealed end of the container can be pierced to couple the stored liquid drug to a needle conduit. The needle conduit can be coupled to a needle insertion component that provides access to the patient. A drive system of the drug delivery device can expel the liquid drug from the container to the patient through the needle conduit. The drive system can be controlled to provide the liquid drug to the patient in a single dose or over multiple doses. The drive system can include an energy storage component and an energy transfer component to enable the drug delivery device to maintain a small form factor. As a result, the patient's comfort when using the drug delivery device is improved. Other embodiments are disclosed and described.

Figure 1:
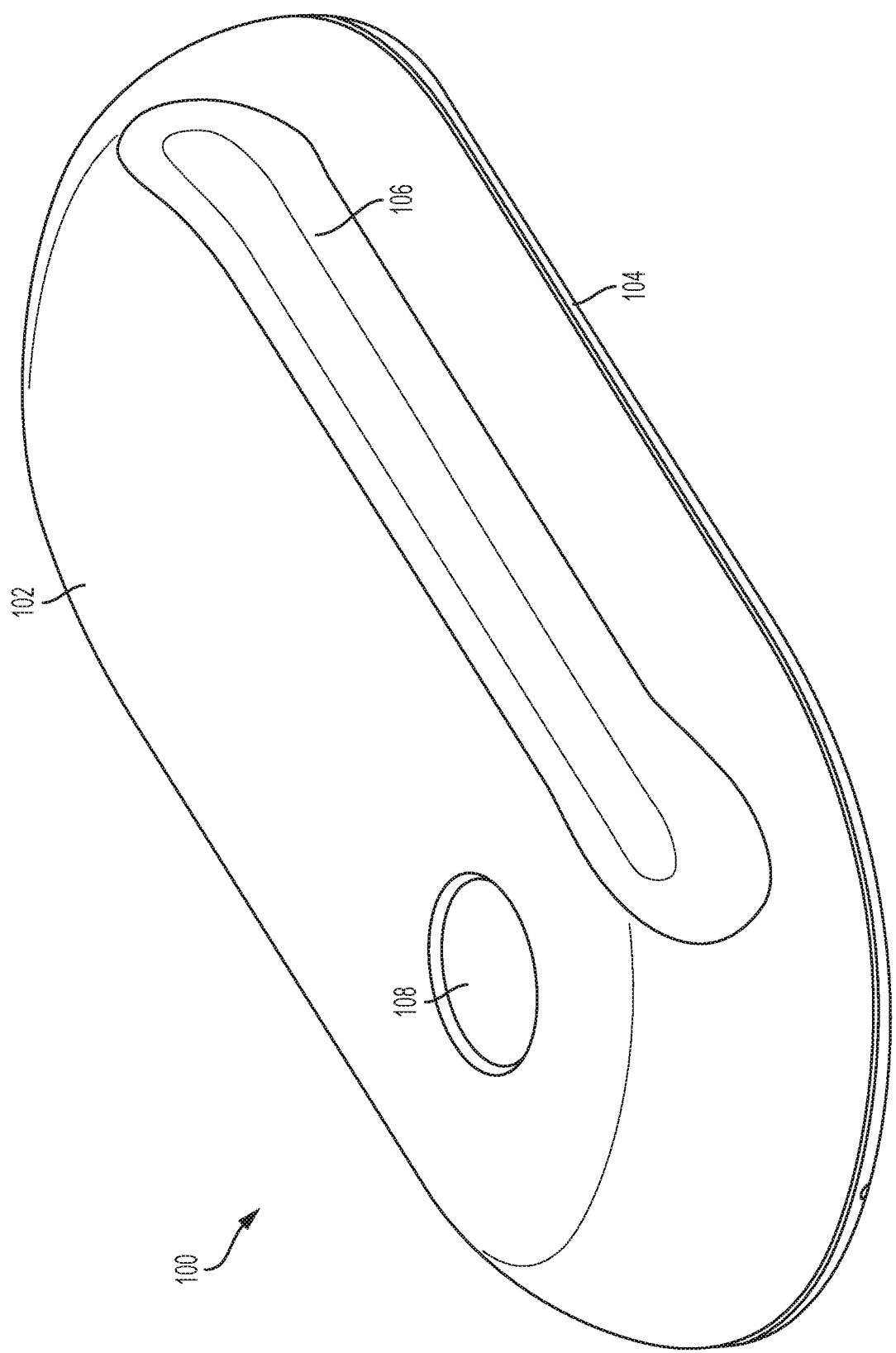
FIG. 1 illustrates a first exemplary embodiment of a drug delivery device.

FIG. 1 illustrates a first exemplary embodiment of a drug delivery device 100. The drug delivery device 100 can include a top portion or cover 102 and a lower portion or base 104. The top portion 102 and the lower portion 104 can together form a housing of the drug delivery device 100. The top portion 102 and the lower portion 104 can be coupled together to form an outside of the drug delivery device 100. The top portion 102 and the lower portion 104 can be formed from any material including, for example, plastic, metal, rubber, or any combination thereof.

The drug delivery device 100 can be used to deliver a therapeutic agent (e.g., a drug) drug to a patient or user. In various embodiments, the drug delivery device 100 can include a container for retaining a liquid drug. The drug delivery device 100 can be used to deliver the liquid drug from the container to the patient. Any type of liquid drug can be stored by the drug delivery device 100 and delivered to a patient. In various embodiments, the container can contain any therapeutic agent such as, for example, a drug, a subcutaneous injectable, a medicine, or a biologic. A patient receiving a drug or other medicine (or any liquid) from the drug delivery device 100 can also be referred to as a user.

The drug delivery device 100 can operate as a bolus drug delivery device. In general, the drug delivery device 100 can provide any amount of the stored liquid drug to a patient over any period of time. In various embodiments, the drug delivery device 100 can provide the stored liquid drug to the patient in a single dose over a desired amount of time. In various embodiments, the drug delivery device 100 can provide the stored liquid drug to the patient over multiple doses. Each of the multiple doses can include substantially the same amount of the liquid drug or the sizes of the doses can vary. Further, each of the multiple doses can be provided to the patient over substantially the same amount of time or the delivery times can vary. Additionally, the times between multiple doses can be approximately equal or can vary.

The drug delivery device 100 can maintain the liquid drug within a primary drug container. The primary drug container can be a cartridge. As an example, the cartridge can be an International Organization for Standardization (ISO) standardized cartridge. The drug delivery device 100 can be provided to the patient with a preloaded and prefilled cartridge. In various embodiments, the drug delivery device 100 can include a slot or opening for a patient to load a prefilled cartridge into the drug delivery device 100. In various embodiments, the drug delivery device 100 can be designed and/or intended for a single use such that after the liquid drug is delivered to the patient, the drug delivery device 100 can be discarded. In various embodiments, the primary drug container can be filled or refilled by a patient such that the drug delivery device 100 can be reused. In various embodiments, the drug delivery device 100 can include a port for accessing and filling the primary drug container.

As shown in FIG. 1, the top portion 102 of the drug delivery device 100 can include a raised portion 106. The raised portion 106 can be elongated and run along a side of the drug delivery device 100. A liquid drug cartridge can be approximately positioned under the raised portion 106 such that the raised portion 106 accommodates the size and positioning of the liquid drug container within the drug delivery device 102. The top portion 102 can also include a patient interaction element or component 108. In various embodiments, the patient interaction element 108 can be a push button or other patient input device. The patient interaction element 108 can be used to activate the drug delivery device 100. For example, when a patient presses on the patient interaction element 108, the drug delivery device 100 can begin delivering the stored liquid drug to the patient. Prior to activation, the drug delivery device 100 can remain in an idle state of operation. In various embodiments, the patient interaction element 108 can be used to start, stop, and/or restart delivery of the liquid drug to the patient to enable a patient to dispense multiple doses of the liquid drug.

The drug delivery device 100 can be a wearable drug delivery device 100. As a wearable device, the drug delivery device 100 can be an on-body delivery system (OBDS). The drug delivery device 100 can be coupled to a patient in a number of ways. For example, the lower portion 104 of the drug delivery device 100 can include an adhesive for attaching to a patient. In various embodiments, the drug delivery device 100 can be attached to a secondary device attached or worn by the patient such that the drug delivery device 100 fits onto or can be coupled to the secondary device.

FIG. 1 illustrates an exemplary form factor of the drug delivery device 100. In various embodiments, the drug delivery device 100 can be designed according to any desired form factor—for example, according to any desired shape and size of the top and lower portions 102 and 104. Further, the drug delivery device 100 can include any number of components that can be coupled together to form the housing of the drug delivery device 100. In various embodiments, the drug delivery device 100 can be a handheld device operating, for example, similar to an auto-injector.

The drug delivery device 100 can also include multiple patient interaction elements and is not limited to only including the patient interaction element 108. In various embodiments, the drug delivery device 100 can include two or more patient interaction elements 108. In various embodiments, the drug delivery device 100 can include an on-body interlock that may be required to be engaged prior to allowing the drug delivery device 100 to operate. For example, the on-body interlock can be positioned on a bottom side of the drug delivery device 100 (e.g., on an outside portion of the lower portion 104). The on-body interlock can be an exposed button or switch that can be passively depressed when coupled to the patient. After the on-body interlock is depressed, the drug delivery device 100 can be operated, for example, by a patient interacting with the patient interaction element 108. In various embodiments, operation of the drug delivery device 100 can be stopped when the drug delivery device 100 is decoupled or removed from the patient—for example, when the on-body interlock is no longer passively depressed.

In various embodiments, the drug delivery device 100 can operate as a mechanical device. For example, the drug delivery device 100 can include only mechanical components and/or can provide only mechanical functionality and operation. In various other embodiments, the drug delivery device 100 can operate as an electromechanical device. For example, the drug delivery device 100 can include one or more controllers associated memory for controlling various components of the drug delivery device 100. As an electromechanical device, the drug delivery device 100 can include other electrical and/or electromechanical components such as, for example, sensors, user interfaces, and communication interfaces. In various embodiments, a first portion of the drug delivery device 100 can be a mechanical based system (e.g., a drive system for expelling a drug from a container for delivery to the user) while a second portion of the drug delivery device 100 can be an electromechanical based system (e.g., components for measuring and recoding dosage amounts). Operation of the drug delivery device 100 can be entirely patient-based, automated, and/or semi-autonomous.

Figure 2:
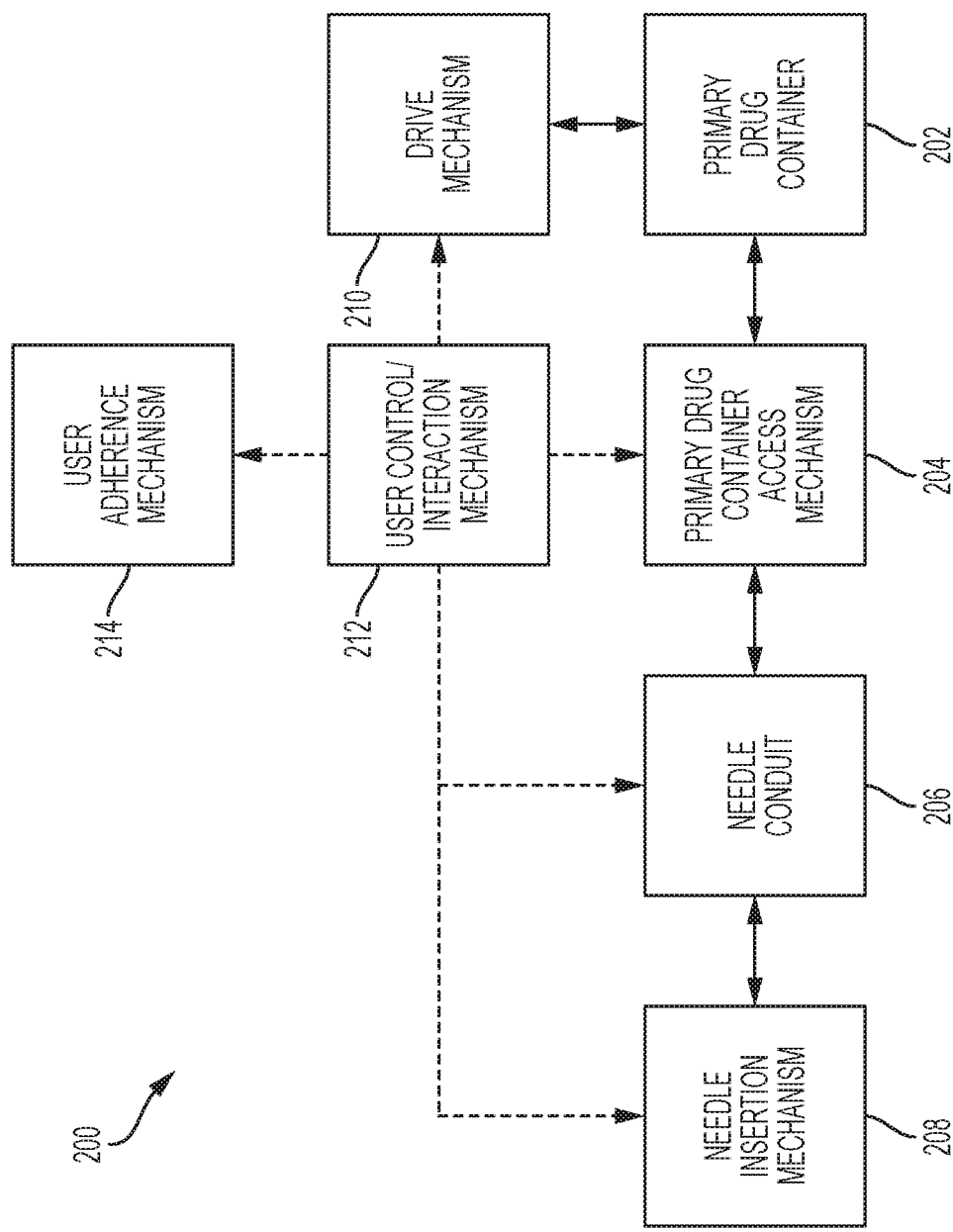
FIG. 2 illustrates a first exemplary embodiment of various functional components of the drive delivery device of FIG. 1.

FIG. 2 illustrates an exemplary embodiment 200 of various functional components of the drive delivery device 100. FIG. 2 can represent the various functional components of the drug delivery device 100 when implemented as a mechanical device (e.g., including the function and operation of the constituent components of the drug delivery device 100 depicted in FIG. 2). The functional components depicted in FIG. 2 can be contained or positioned within the drug delivery device 100 (e.g., contained within the top portion 102 and the lower portion 104).

As shown in FIG. 2, the mechanical implementation of the drug delivery device 100 can include a primary drug container 202, a primary drug container access mechanism or component 204, a needle conduit 206, a needle insertion mechanism or component 208, a drive mechanism or component 210, a user control and/or interaction mechanism or component 212, and a patient (or user) adherence or coupling mechanism component 214.

The primary drug container 202 can store any type of liquid drug. As mentioned, the primary drug container 202 can be a cartridge including, for example, an ISO standardized cartridge. The primary drug container 202 can be provided as preloaded into the drug delivery device 100 and prefilled with the stored liquid drug. In various embodiments, the patient can load a prefilled cartridge into the drug delivery device 100. Further, in various embodiments, the primary drug container 202 can be accessible for filling or refilling through a port provided on the drug delivery device 100. Prior to activation of the drug delivery device 100, the primary drug container 202 can maintain the stored liquid drug. That is, the liquid drug can be sealed or contained within the primary drug container 202. Once the drug delivery device 100 is activated, the liquid drug stored in the primary drug container 202 can be accessed to provide the stored liquid drug to the patient.

The primary drug container access mechanism or component 204 can be coupled to the primary drug container 202. The primary drug container access mechanism 204 can provide access to the liquid drug stored in the primary drug container 202. When activated, the primary drug container access mechanism 204 can couple the stored liquid drug to the needle conduit 206. In various embodiments, the primary drug container access mechanism 204 can pierce a sealable end of the primary drug container, thereby obtaining access to the stored liquid drug.

The needle conduit 206 can include tubing or other fluid delivery mechanisms for transferring the stored liquid drug retained in the primary drug container 202 to the needle insertion mechanism 208. The needle conduit 206 can be routed around any internal portion of the drug delivery device 100. The needle conduit 206 can be formed, for example, from plastic tubing, metal tubing (e.g., stainless steel tubing), or a combination thereof. In general, the needle conduit 206 can provide a fluid path for the liquid drug when expelled from the primary drug container 202.

The needle insertion mechanism or component 208 can provide access to the patient. For example, the needle insertion mechanism 208 can include a needle and/or a cannula for providing access to a patient and for providing a path for delivering the liquid drug to the patient. The needle insertion mechanism 208 can include a hard needle that can be maintained in a retracted mode inside of the drug delivery device 100 prior to activation. Once activated, the needle insertion mechanism 208 can extend the hard needle into the patient. The hard needle can then be retracted while leaving a cannula or soft needle inside of the patient. The soft needle of the needle insertion mechanism 208 can be coupled to the needle conduit 206. Accordingly, after activation, a complete path from the primary drug container 202 to the needle insertion mechanism 208 through the needle conduit 206 can be provided.

Once a complete fluid path for the liquid drug is provided, the drive mechanism 210 can be used to expel the liquid drug from the primary drug container 202 for delivery to the patient. For example, the drive mechanism 210 can be used to expel a desired amount of the liquid drug that is to be provided to the patient over a certain amount of time. In various embodiments, the drive mechanism 210 can operate and control a plunger that can expel a portion of the liquid drug from the primary drug container 202 based on the movement of the plunger. In various embodiments, the flow of the liquid drug to the patient can be based on the drive mechanism 210 and other factors such as the size (e.g., diameter and length) of the needle conduit 206 to the patient.

The user control/interaction mechanism or component 212 can include any number of patient input elements or components including, for example, one or more buttons, triggers, knobs, switches, and/or sliding features. The user control/interaction mechanism 212 can be positioned on any outer surface of the drug delivery device 100. The user control/interaction mechanism 212 can be used to activate initial operation of the drug delivery device 100. For example, by interacting with the user control/interaction mechanism 212, a patient can initiate insertion of the hard needle and/or soft needle of the needle insertion mechanism 208 into the patient. Further, the patient can initiate access to the liquid drug stored in the primary drug container 202 by the primary drug container access mechanism 204. Additionally, the patient can initiate activation of the drive mechanism 210 to initiate delivery of the stored liquid drug from the primary drug container 202 to the patient.

In various embodiments, the user control/interaction mechanism 212 can be used to start, stop, and/or restart delivery of the liquid drug to the patient. In various embodiments, the user control/interaction mechanism 212 can be used to initiate delivery of the liquid drug to the patient in a single dose. In various embodiments, the user control/interaction mechanism 212 can be used to initiate delivery of the liquid drug to the patient over multiple doses (e.g., multiple discrete doses). In various embodiments, one or more elements of the user control/interaction mechanism 212 can be used to control operation of the drug delivery device 100 (e.g., starting and stopping delivery of the liquid drug using separate buttons of the user control/interaction mechanism 212). In various embodiments, operation of the drug delivery device 100 can be automated based on use of the user control/interaction mechanism 212.

The patient (or user) adherence mechanism 214 can be used to couple the drug delivery device 100 to the patient. As mentioned, the patient adherence mechanism 214 can include an adhesive for attaching the drug delivery device 100 to the patient. For example, the drug delivery device 100 can include an adhesive strip or pad positioned on the lower portion 104 of the drug delivery device to facilitate adherence to a patient (e.g., a "peel and stick" adherence mechanism). In various embodiments, the patient adherence mechanism 214 can include one or more features for coupling to another device coupled to the patient. The user control/interaction mechanism 212 can be used to engage or disengage the drug delivery device 100 to any secondary device coupled to the patient.

The constituent components of the drug delivery device 100 depicted in FIG. 2 can be mechanically designed and operated. That is, the constituent components of the drug delivery device 100 depicted in FIG. 2 can be operated to deliver a stored liquid drug to a patient in one or more doses over a desired amount of time without the use of any electrical components or an electrical power source. As a result, a mechanical implementation of the drug delivery device 100 can be provided in a cost-effective and reliable manner.

Figure 3:
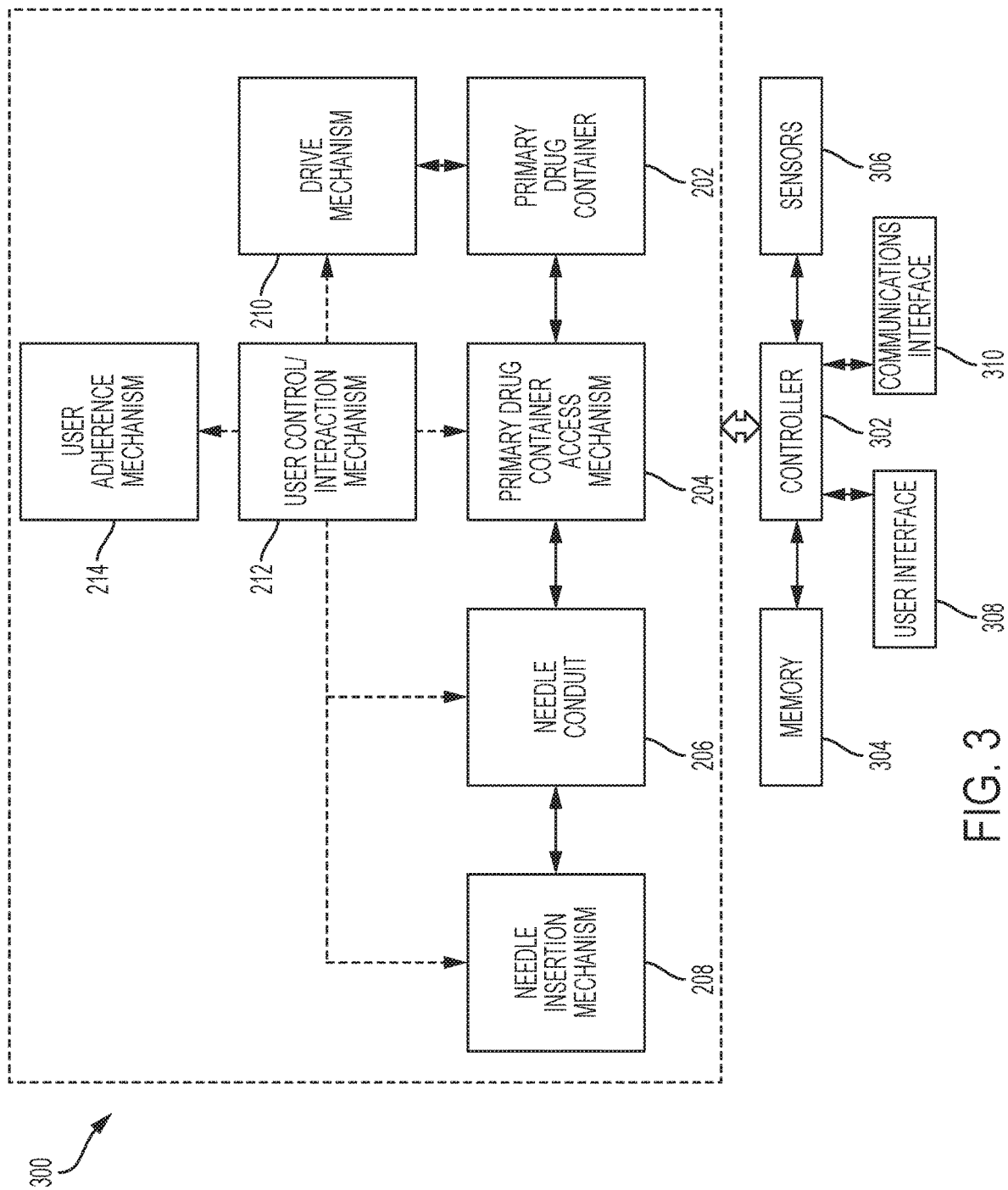
FIG. 3 illustrates a second exemplary embodiment of various functional components of the drive delivery device of FIG. 1.

FIG. 3 illustrates a second exemplary embodiment 300 of the various functional components of the drug delivery device 100. FIG. 3 can represent the various functional components of the drug delivery device 100 when implemented as an electromechanical device (e.g., including the function and operation of the constituent components of the drug delivery device 100). The functional components depicted in FIG. 3 can be contained or positioned within the drug delivery device 100 (e.g., contained within the top portion 102 and the lower portion 104).

As shown in FIG. 3, the exemplary embodiment 300 can include the functional components included in the exemplary embodiment 200: a primary drug container 202, a primary drug container access mechanism or component 204, a needle conduit 206, a needle insertion mechanism or component 208, a drive mechanism or component 210, a user control and/or interaction mechanism or component 212, and a patient adherence or coupling mechanism or component 214. Each of these components can be implemented as mechanical or electromechanical components. The exemplary embodiment 300 can further include a controller 302, a memory 304, a sensor 306, an additional user interface 308, and a communications interface 310.

The memory 304 can be coupled to the controller 302. The controller 302 can include one or more processors. The controller 302 can implement any software, code, or instructions stored in the memory 304. The sensor 306 can be any type of sensor. In various embodiments, the sensor 306 can include any type of sensor for monitoring a condition of the patient or for monitoring operation of the drug delivery device 100. For example, the sensor 306 can be flow sensor, a viscosity sensor, a sensor for determining a positioning of a plunger of the drug delivery device 100, a sensor for determining an amount of liquid drug delivered to the user, a sensor for determining how much liquid drug remains in the drug delivery device 100, a Hall effect sensor, and or a photogate. The sensor 306 can also be a temperature sensor, an electrocardiography (ECG) sensor, a blood pressure sensor, a blood glucose sensor, or any other type of patient biometric sensor.

The user interface 308 can include, for example, a touchscreen, a liquid crystal display (LCD), light emitting diode (LED) display, or any other type of display for presenting information to the patient and/or receiving an input from the patient. The user interface 308 can also include interfaces for providing feedback or an output to the patient such as haptic feedback (e.g., vibrational feedback) or an audio or visual output. In general, the user interface 308 can include one or more interfaces for displaying or providing information to the patient and/or receiving information from the patient.

The communications interface 310 can include any type of communications interface for communicatively coupling the drug delivery device 100 to an external or remote device. In various embodiments, the communications interface 310 can include a wireless or wired communications interface operating according to any wired or wireless communications standard. In various embodiments, the communications interface 310 can include a Bluetooth, Bluetooth Low Energy, and/or WIFI communications interface. The communications interface 310 can also include a wired interface such as a USB interface. Information or data related to the operation of the drug delivery device 100 or state of the patient can be conveyed from the drug delivery device 100 to a remote device (e.g., a mobile device, tablet, computer, or smartphone) coupled to the communications interface 310. Further, data collected or monitored by the sensor 306 can be provided to a remote device by way of the communications interface 310. Such data can also be stored by the memory 304. Operation of the drug delivery device 100 can be controlled or adjusted by a remote device coupled to the drug delivery device 100 by the communications interface 310.

The controller 302 can be coupled to any other component of the drug delivery device 100. The controller 302 can monitor the status of any other component of the drug delivery device 100 and can control the operation of any component of the drug delivery device 100. The controller 302 can determine the operation of the drug delivery device 100 based on, for example, patient input provided through the user control/interaction mechanism 212 and/or the user interface 308. Overall, the controller 302 can operate to activate the drug delivery device 100—for example, to initiate activation of the needle insertion mechanism 208 and the primary drug container access mechanism 204 to begin delivery of the stored liquid drug to the patient. Further, the controller 302 can stop (and restart) delivery of the liquid drug to the patient—either automatically or subject to patient control—to facilitate delivery of the liquid drug over multiple doses.

In various embodiments, one or more of the controller 320, the memory 304, the sensor 306, the user interface 308, and the communications interface 310 can be positioned or contained within the housing of the drug delivery device 100. In various embodiments, one or more of the controller 320, the memory 304, the sensor 306, the user interface 308, and the communications interface 310 can be positioned or contained within the housing of the drug delivery device 100 can be provided on an electronics connectivity module that can be coupled to the drug delivery device 100. For example, the electronics connectivity module can be inserted into the drug delivery device 100.

In various embodiments, the controller 302 can provide audible, visual, and/or haptic-based alarms and reminders to the patient. Further, the controller 302 can monitor and store dosing information (e.g., in the memory 304) including predetermined or preprogrammed dosing schedules and actual dosing schedules. In general, the controller 302 can operate as a timer to control dosing. Information regarding dosages (e.g., times and amounts) can be stored in the memory 304. Further, the communications interface can be coupled to any type of remote device either directly (e.g., over a wired or wireless commutations interface 310) or indirectly (e.g., over a cloud-based or other network-based communications link).

Each of the individual components shown in FIG. 3—the primary drug container 202, the primary drug container access mechanism 204, the needle conduit 206, the needle insertion mechanism 208, the drive mechanism 210, the user control and/or interaction mechanism 212, and the patient adherence or coupling mechanism 214—can function and operate as described in relation to FIG. 2 and/or can include electrical and/or electromechanical features and can enable control by the controller 302.

The drug delivery device 100—including the functional components of the drug delivery device 100 depicted in FIGS. 2 and 3—can operate according to a number of operational states. In various embodiments, the drug delivery device 100 can include an idle state. In the idle state, the drug delivery device 100 can maintain the stored liquid drug in the primary drug container 202. The idle state can represent a state of operation prior to accessing the patient using the needle insertion mechanism 204 and prior to accessing the primary drug container 202 using the primary drug container access mechanism 204. Accordingly, while in the idle state, the needle conduit 206 can remain decoupled from the stored liquid drug.

From the idle state, the drug delivery device 100 can enter an activation state. The drug delivery device 100 can enter the activation state based on patient input or can enter the activation state automatically without patient input. During a first portion of the activation state (e.g., initial activation), the needle insertion mechanism 208 can provide access to the patient. Further, the primary drug container access mechanism 204 can provide access to the liquid drug stored in the primary drug container 202. As a result, the needle conduit 206 can be coupled to the stored liquid drug such that the liquid drug can be provided to the needle insertion mechanism 208.

During a second portion of the activation state (e.g., delivery), the drive mechanism 210 can help expel the liquid drug from the primary storage container 202, through the needle conduit 206, and on to the needle insertion mechanism 208 for delivery to the patient. The drive mechanism 210 can be operated based on patient input and/or can be operated automatically.

Figure 4:
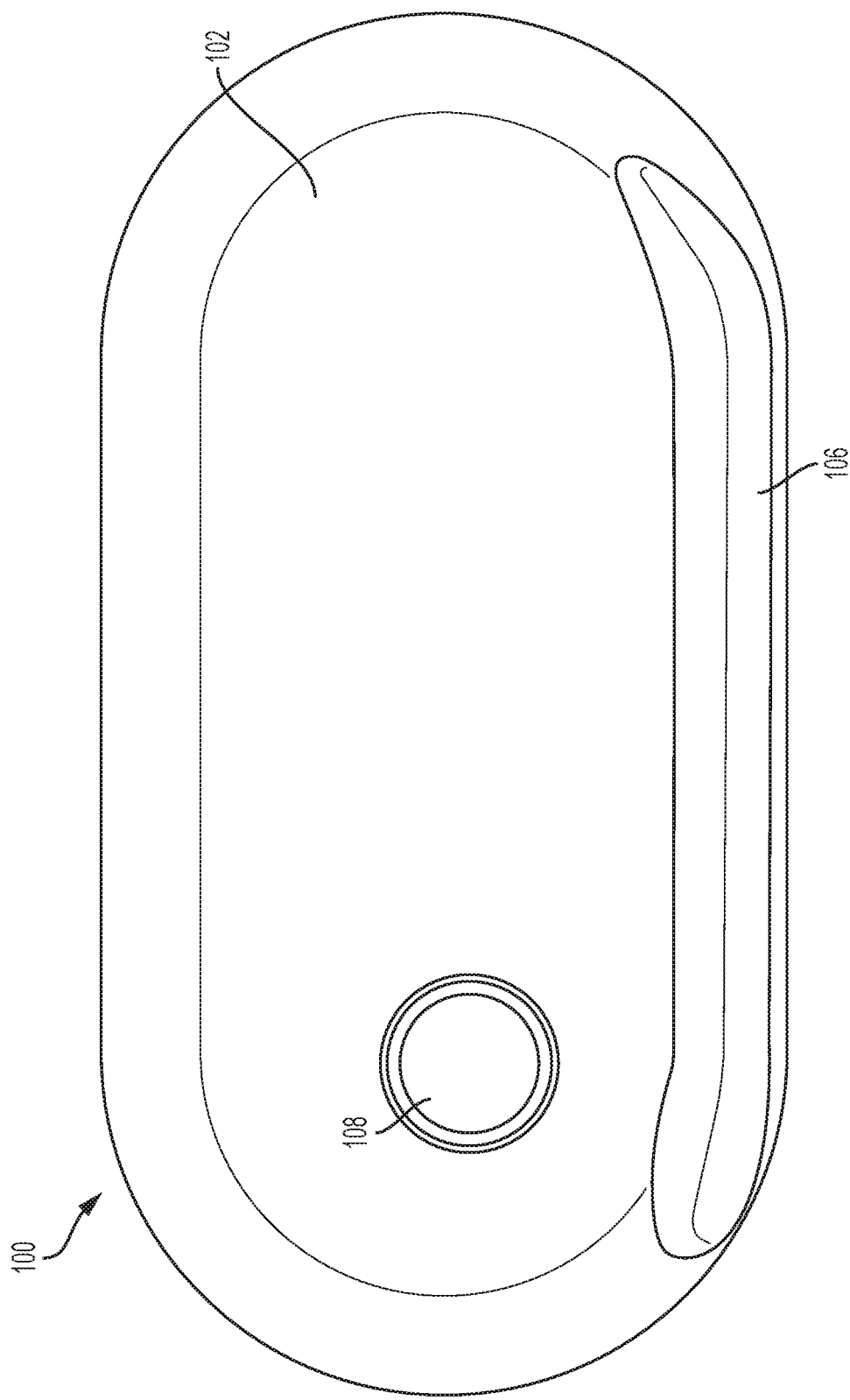
FIG. 4 illustrates a top view of the drug delivery device of FIG. 1.

FIG. 4 illustrates a top view of the drug delivery device 100. As shown in FIG. 4, the patient interaction element 108 can be positioned on the top surface of the top portion 102. The patient interaction element 108 can be positioned along any portion of a top surface of the top portion 102 (or along any portion of the drug delivery device 100). The raised portion 106 is shown positioned along a periphery of the top surface of the top portion 102 but is not so limited. That is, the raised portion 106 can be positioned along any portion of the top surface of the top portion 102 (or along any portion of the drug delivery device 100).

Figure 5:
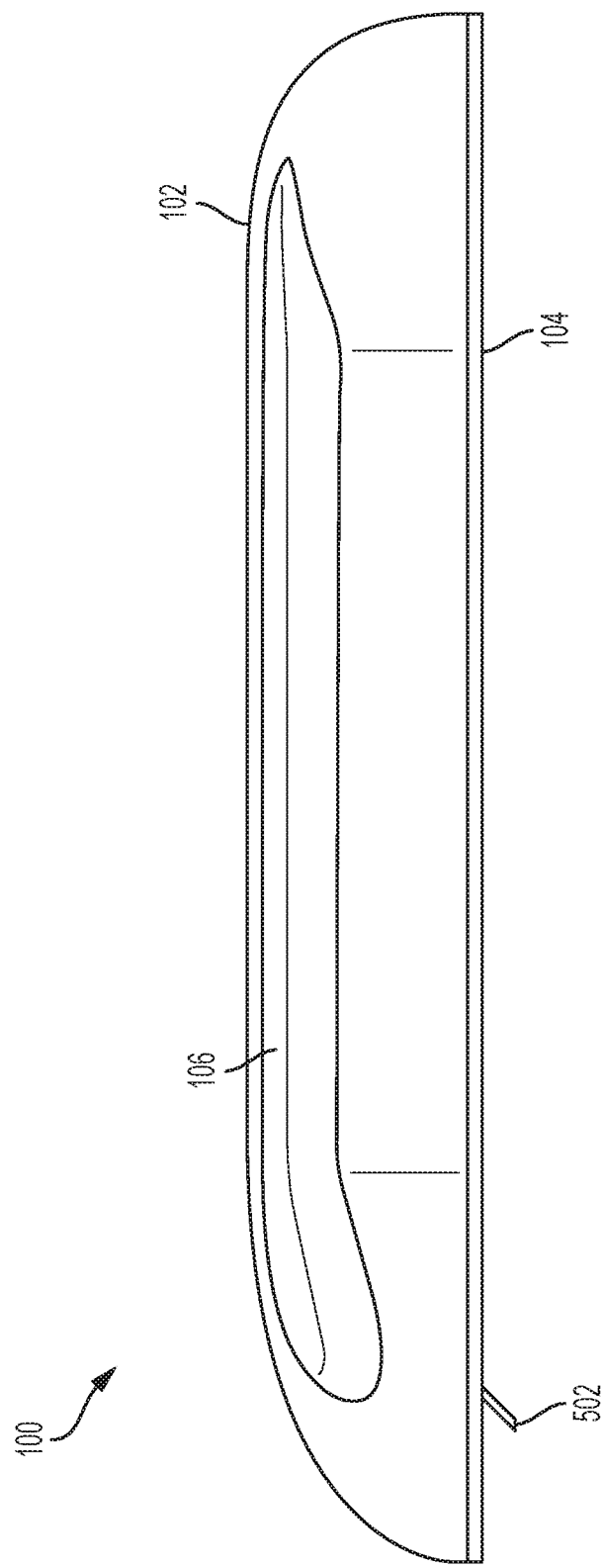
FIG. 5 illustrates a first side view of the drug delivery device of FIG. 1.

FIG. 5 illustrates a first side view of the drug delivery device 100. As shown in FIG. 5, the drug delivery device 100 can include a protrusion 502. The protrusion 502 can extend from the bottom portion 104 of the drug delivery device 100. The protrusion 502 can extend from along any portion of the bottom portion 104 of the drug delivery device 100. The protrusion 502 can be of any length and can extend below the bottom portion 104 by any amount. The protrusion 502 can be a portion of the needle insertion mechanism 208 depicted in FIGS. 2 and 3. In various embodiments, the protrusion 502 can be a soft needle or cannula that extends from the drug delivery device 100 into the patient once a hard needle of the needle insertion mechanism 208 has been retracted back inside the drug delivery device 100. The protrusion 502 can extend below the bottom portion 104 when attached to a patient and when delivering a liquid drug to the patient. The bottom portion 104 of the drug delivery device 100 can include a port or opening allowing for extension of the hard and soft needle and retraction of the hard needle of the needle insertion mechanism 208. In various embodiments, the protrusion 502, as a soft needle, can remain extended outside of the drug delivery device 100 after activation. Accordingly, the drug delivery device 100 can provide sharps protection as no sharp or hard needle remains extended from the drug delivery device 100. Prior to activation, the protrusion 502 can be positioned within the drug delivery device 100 (e.g., so as not to extend below the lower portion 104). The first side view of the drug delivery device 100 shown in FIG. 5 illustrates the raised portion 106 positioned on a first side of the drug delivery device 100.

Figure 6:
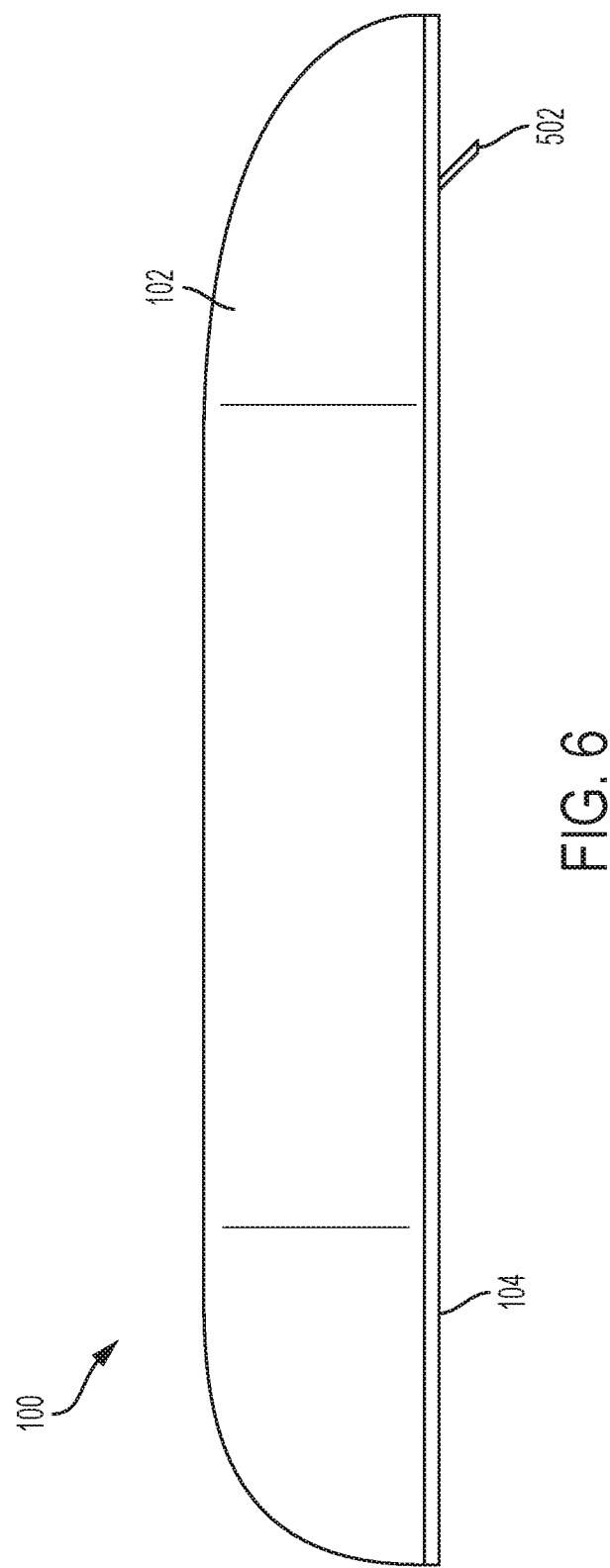
FIG. 6 illustrates a second side view of the drug delivery device of FIG. 1.
Figure 7:
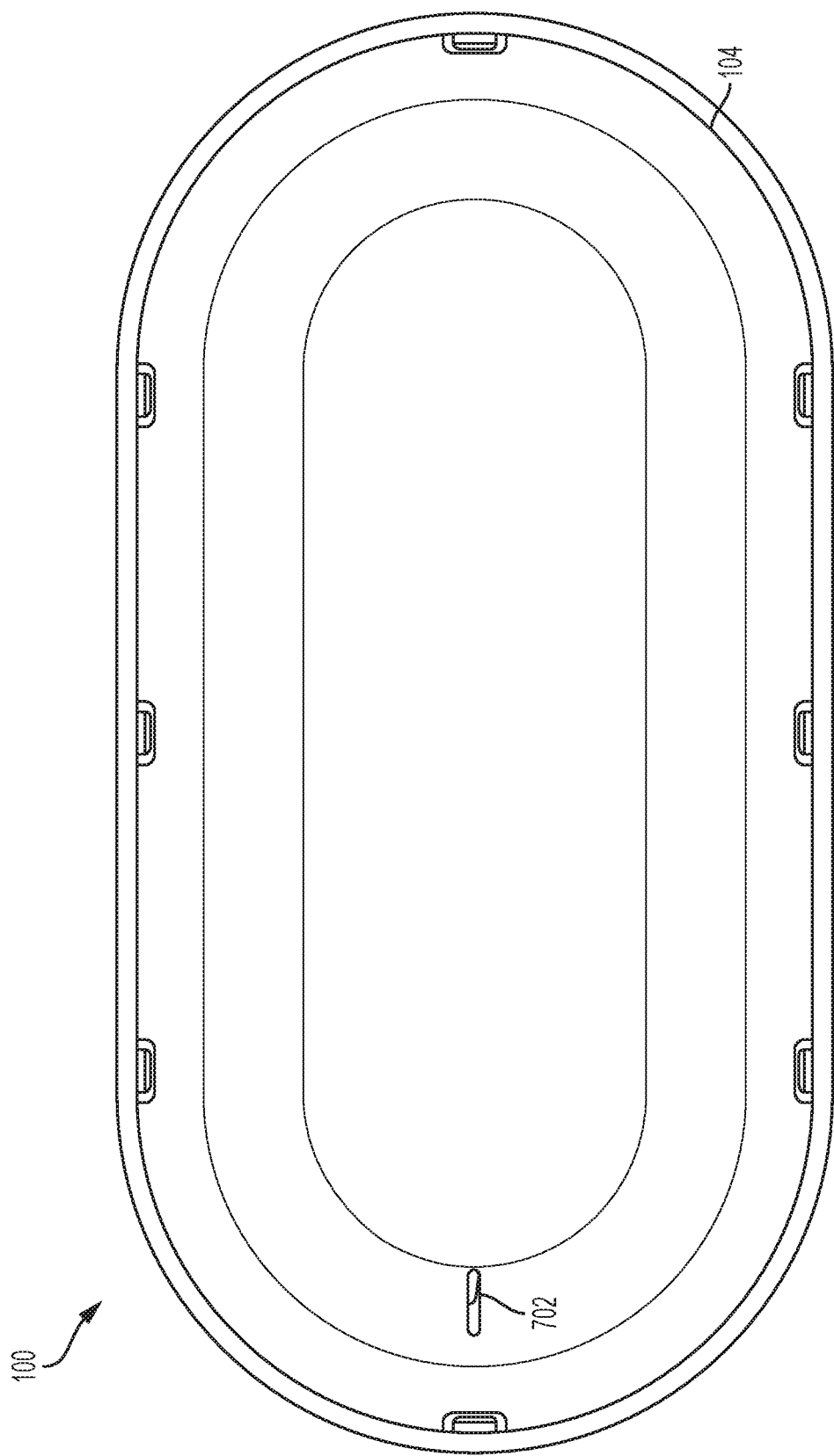
FIG. 7 illustrates a bottom view of the drug delivery device of FIG. 1.

FIG. 6 illustrates a second side view of the drug delivery device 100. As shown in FIG. 6, the protrusion 502 extends below the lower portion 104. FIG. 7 illustrates a bottom view of the drug delivery device 100. As shown in FIG. 7, the bottom portion 104 of the drug delivery device 100 can include an opening or a port 702. The opening 702 can provide a space for a hard needle, soft needle, or other element of the needle insertion mechanism 208 to extend from inside of the drug delivery device 100 beyond the bottom portion 104. The opening 702 can also allow the hard (e.g., sharp) needle of the needle insertion mechanism 208 to retract back inside of the drug delivery device 100. As a result, the hard needle can remain above the lower portion 104 such that no sharp portion of the needle insertion mechanism 208 extends through the opening 702 and/or below the lower portion 104 of the drug delivery device 100.

Figure 8:
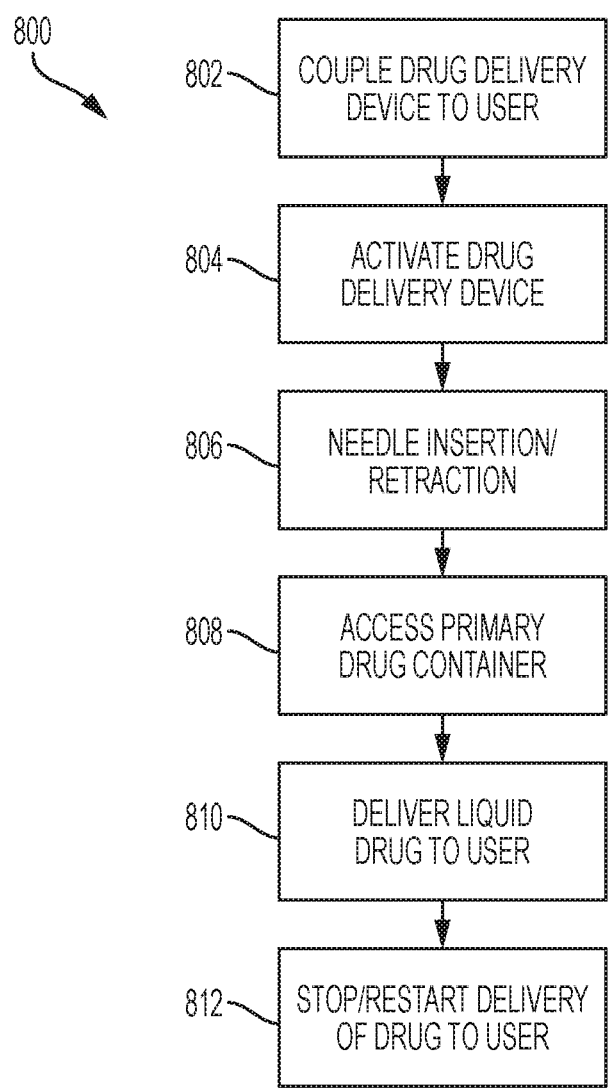
FIG. 8 illustrates an exemplary method of operation for the drug delivery device of FIG. 1.

FIG. 8 illustrates an exemplary method of operation 800 for the drug delivery device 100. At 802, the drug delivery device 100 can be coupled to a patient. The drug delivery device 100 can be coupled directly to a patient such that a hard needle, soft needle, and/or cannula of the needle insertion mechanism 208 can make contact with the patient when extended from the drug delivery device 100. The drug delivery device 100 can be coupled to a patient by, for example, the patient adherence mechanism 214. When coupled to the patient, the lower portion 104 of the drug delivery device 100 can be in direct contact with the patient.

At 804, the drug delivery device 100 can be activated. Prior to activation, the drug delivery device 100 can be maintained in an idle or waiting state when coupled to the patient. The drug delivery device 100 can be activated manually or automatically. In various embodiments, the drug delivery device 100 can be activated by a patient interacting with a patient control feature positioned on the drug delivery device 100 such as, for example, the patient control/interaction mechanism 212.

After activation, at 806, a needle of the drug delivery device 100 can be inserted into the patient. The needle can be a soft needle and can be a part of the needle insertion mechanism 208 of the drug delivery device 100. A hard needle can be inserted into the patient and then be retracted, leaving the soft needle or cannula coupled to the patient. The insertion and retraction of the hard needle and the placement of the soft needle or cannula in the patient can be triggered by the activation at 804. The needle insertion mechanism 208 can be considered to provide an access point to the patient for delivering the liquid drug to the patient.

After activation, at 808, the primary drug container 202 storing a liquid drug can be accessed. The primary drug container 202 can be accessed by the primary drug container access mechanism 204. Any portion of the primary drug container 202 can be accessed. In various embodiments, the primary drug container 202 can have two sealed ends, with either end providing access to the liquid drug at 808. Access to the primary drug container 202 can be triggered by the activation at 804. Steps 806 and 808 can be implemented in any order and are not limited to being implemented in the order as shown in FIG. 8. Further, steps 806 and 808 can occur approximately simultaneously at the time of activation at 804 and can be considered to be further steps of the activation step 804.

After activation—for example, after needle insertion at 806 and accessing the primary drug container 202 at 808—the liquid drug contained in the primary drug container 202 can be in fluid communication with the needle conduit 206, which can couple the liquid drug to the needle insertion mechanism 208. In various embodiments, at 808, a complete fluid path from the primary drug container 202 to the patient can be established (e.g., by the needle conduit 206 and the needle insertion mechanism 208). Subsequent operation of the drug delivery device 100 can regulate the flow of the liquid drug including starting, stopping, and restarting the flow of the liquid drug to the patient.

At 810, the liquid drug can be delivered to the patient. The liquid drug can be provided from the primary drug container 202, to the needle conduit 206, and on to the needle insertion mechanism 208 for delivery to the patient. Any amount of liquid drug can be delivered to the patient over any desired amount of time over one or more doses separated by any amount of time. At 810, the drive mechanism 210 can drive the liquid drug from the primary drug container 202 to the needle conduit 206. Operation of the drive mechanism 210, and consequently the delivery of the liquid drug to the patient, can be controlled by patient input and/or a controller to enable manual and/or automatic control.

At 812, the operation of the drug delivery device 100 can be controlled as desired to start, stop, and restart delivery of the liquid drug to the patient as desired. For example, the patient can stop operation of the drug delivery device 100 after a first dose of the liquid drug has been delivered to the patient and can then restart operation of the drug delivery device 100 to provide a subsequent dose of the liquid drug to the patient. Operation of the drive mechanism 210 can control the dosing of the liquid drug to the patient as described in relation to 810.

Figure 9:
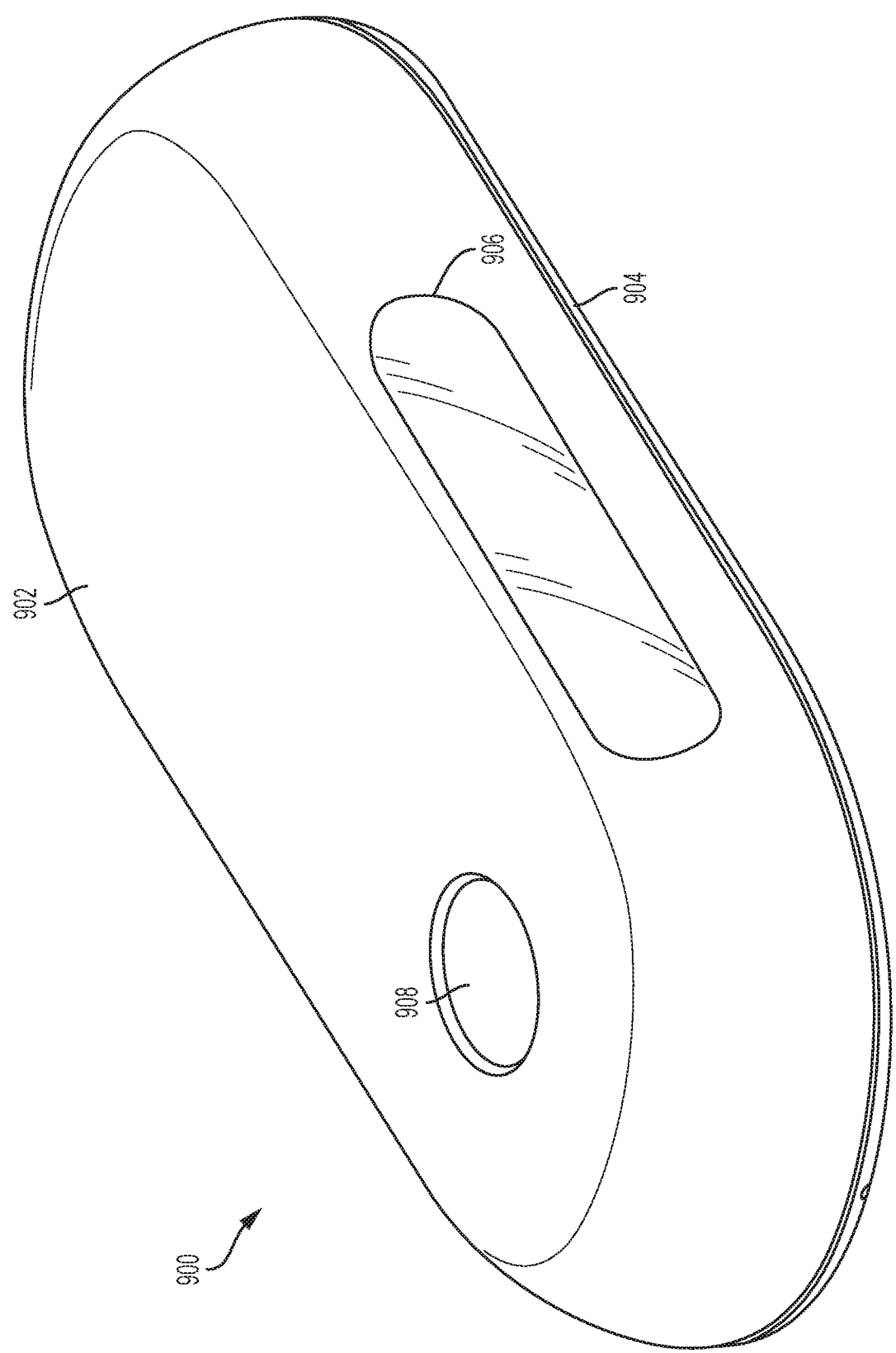
FIG. 9 illustrates a second exemplary embodiment of a drug delivery device.

FIG. 9 illustrates a second exemplary embodiment of a drug delivery device 900. The drug delivery device 900 can operate and provide substantially the same functionality as the drug device 100. As shown in FIG. 9, the drug delivery device 900 can include a top or upper portion 902 and a lower portion or base 904. The top portion 902 and the lower portion 904 can together form a housing of the drug delivery device 900. The top portion 902 and the lower portion 904 can be coupled together to form an outside of the drug delivery device 900. The drug delivery device 900 can represent another design or form factor of the drug delivery device 100.

The drug delivery device 900 can include an opening 906 that can expose a portion of a primary drug container (e.g., a cartridge) positioned within the drug delivery device 900. The opening 906 can allow visual inspection and monitoring of the primary drug container. For example, a patient of the drug delivery device 900 can monitor an amount of liquid drug remaining in the primary drug container. In this way, a patient can monitor dosing status. The opening 906 can also enable a patient to inspect the liquid drug for particles or discoloration. The opening 906 can be covered with a clear material such as plastic to allow a viewing of the primary drug container. The opening 906 can be of any size or shape and can be positioned along any portion of the drug delivery device 900.

The top portion 902 of the drug delivery device 900 can include a patient interaction element or component 908. In various embodiments, the patient interaction element 908 can be a push button. In various embodiments, the patient interaction element 908 can correspond to the patient interaction element 108. The patient interaction element 908 can be used to activate the drug delivery device 900. For example, when a patient presses on the patient interaction element 908, the drug delivery device 900 can begin delivering the stored liquid drug to the patient. In various embodiments, the patient interaction element 908 can be used to start and stop delivery of the liquid drug to the patient to enable a patient to dispense multiple doses of the liquid drug.

In various embodiments, the drug delivery device 900 can include two or more patient interaction elements. In various embodiments, the drug delivery device 900 can also include an on-body interlock device (not shown in FIG. 9).

Figure 10:
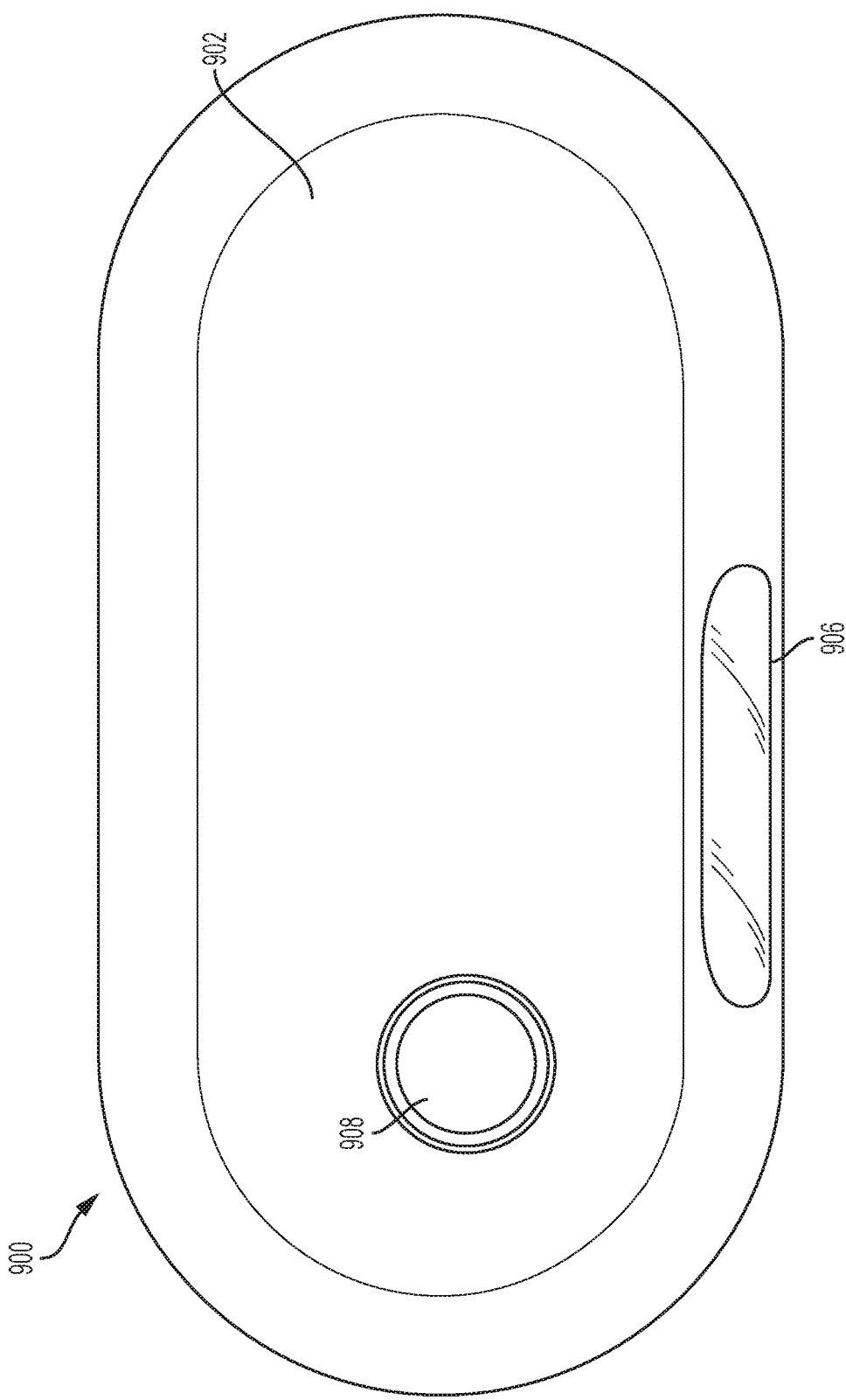
FIG. 10 illustrates a top view of the drug delivery device of FIG. 9.

FIG. 10 illustrates a top view of the drug delivery device 900. As shown in FIG. 10, the opening 906 can be positioned on a side of the upper portion 902 of the drug delivery device. The opening 906 can be positioned along any portion of the upper portion 902.

Figure 11:
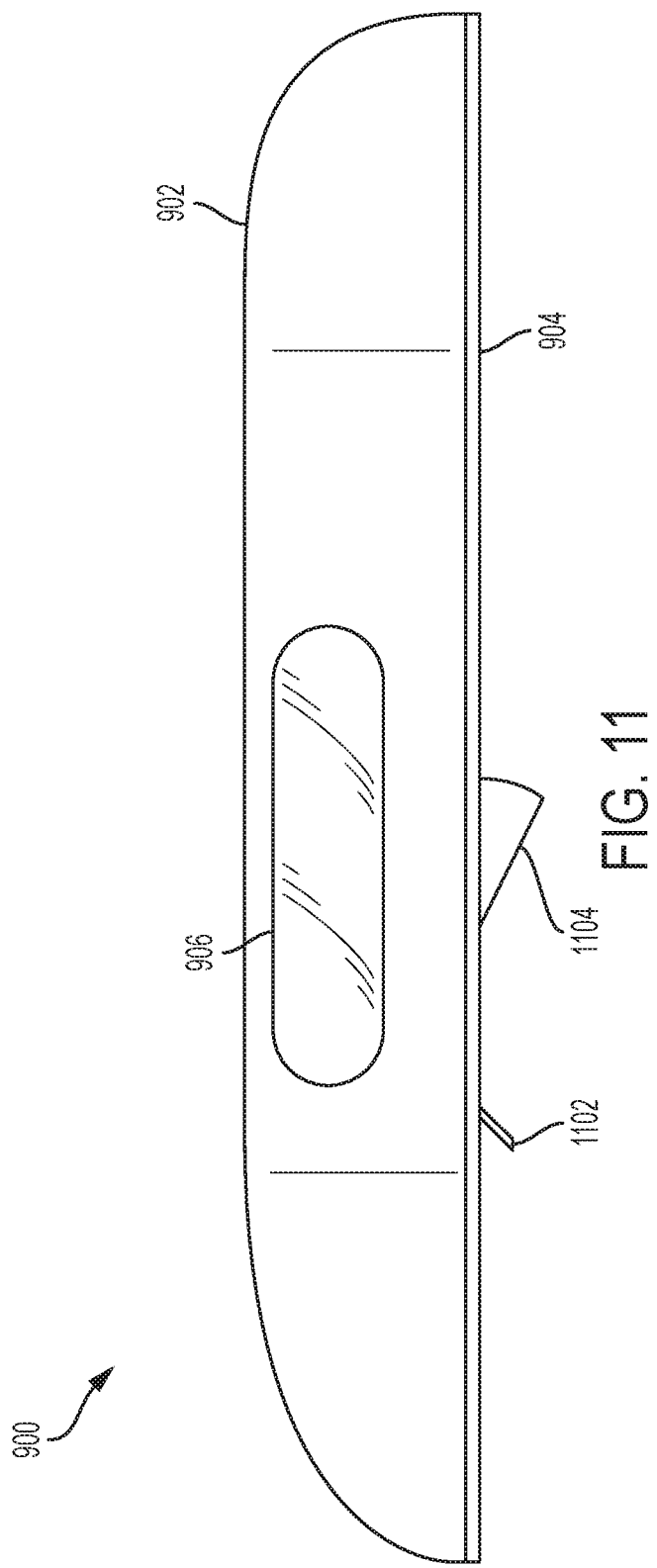
FIG. 11 illustrates a first side view of the drug delivery device of FIG. 9.

FIG. 11 illustrates a first side view of the drug delivery device 900. As shown in FIG. 11, the drug delivery device 900 can include a protrusion 1102. The protrusion 1102 can be a soft needle that can extend from the bottom portion 904 of the drug delivery device 900. The protrusion 1102 can be part of the needle insertion mechanism of the drug delivery device 900. The protrusion 1102 can extend below the bottom portion 902 when attached to a patient and when delivering a liquid drug to the patient. The protrusion 1102 can correspond to the protrusion 502. The protrusion 1102 can be positioned along any portion of the bottom portion 904. The protrusion 1102 can be of any length and can extend below the bottom portion 904 by any amount.

As further shown in FIG. 11, the drug delivery device 900 can include an on-body interlock 1104. The on-body interlock 1104 can also extend from the bottom portion 904 along any portion of the bottom portion 904. The on-body interlock 1104 can be a button or switch that can retract into the drug delivery device 900 when the lower portion 904 is coupled to the patient.

The on-body interlock device 1104 can be required to be depressed (e.g., passively) before the drug delivery device 900 can be activated. For example, when the drug delivery device 900 is coupled to a patient, the on-body interlock device 1104 can be passively depressed. Once depressed, the patient interaction element 108 can subsequently be used to activate the drug delivery device 900. Prior to the on-body interlock 1104 being depressed, the patient interaction element 108 can be disengaged such that manipulation of the patient interaction element 108 does not activate the drug delivery device 900.

The on-body interlock 1104 can also stop operation of the drug delivery device 900. For example, when the drug delivery device 900 is removed from a patient, the on-body interlock 1104 can be biased to extend from the lower portion 904. When so extended, the on-body interlock 1104 can place the drug delivery device 1104 into a stopped or idle state of operation that prevents or stops delivery of the liquid drug to the patient.

The on-body interlock 1104 can be any component that can be biased to extend from the drug delivery device 900 and that can be retracted inside of the drug delivery device 900 when a force is applied. As shown in FIG. 11, the on-body interlock 1104 can be implemented as a pivoting component, biased to remain outside of the drug delivery device 900 and to pivot into the drug delivery device 900 when passively depressed. In various other embodiments, the on-body interlock 1104 can be implemented as a push rod.

As further shown in FIG. 11, the opening 906 can be positioned a side of the upper portion 906. The opening 906 can be of any size and/or shape. The opening 906 can have any width or height.

Figure 12:
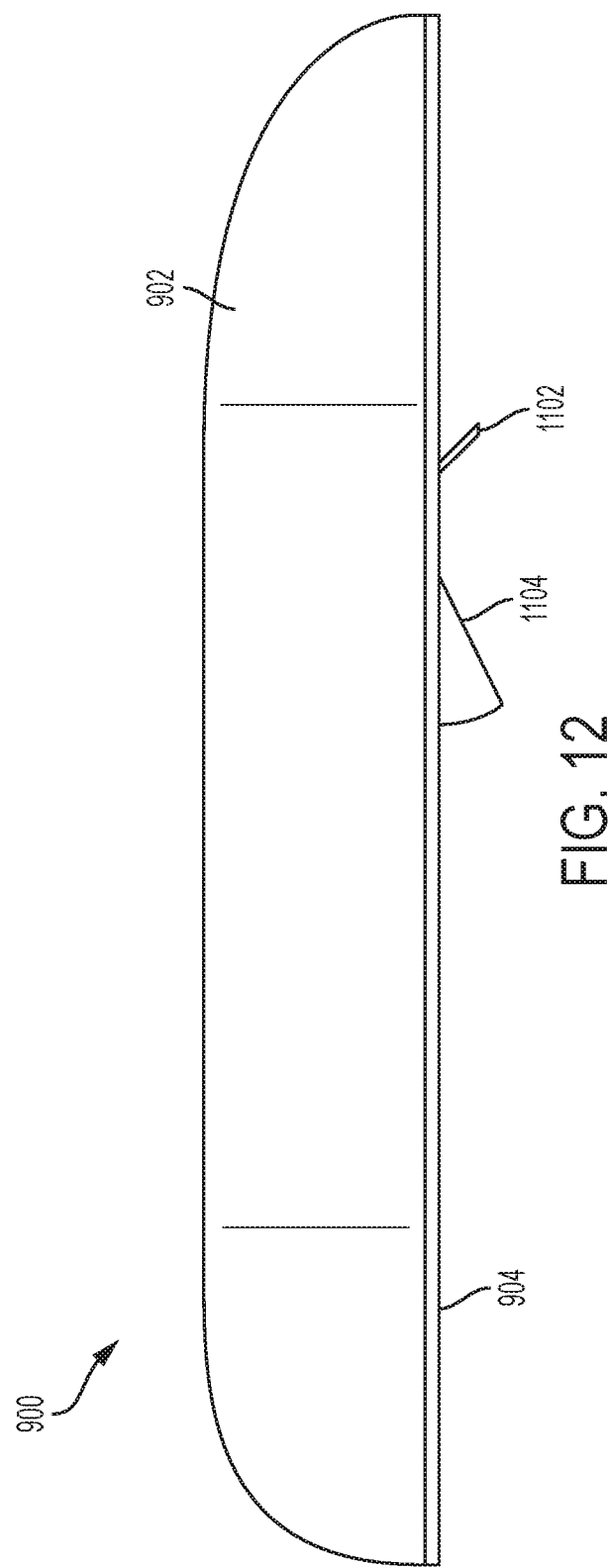
FIG. 12 illustrates a second side view of the drug delivery device of FIG. 9.

FIG. 12 illustrates a second side view of the drug delivery device 900. As shown in FIG. 12, the protrusion 1102 and the on-body interlock 1104 extend form the lower portion 904 of the drug delivery device 900.

Figure 13:
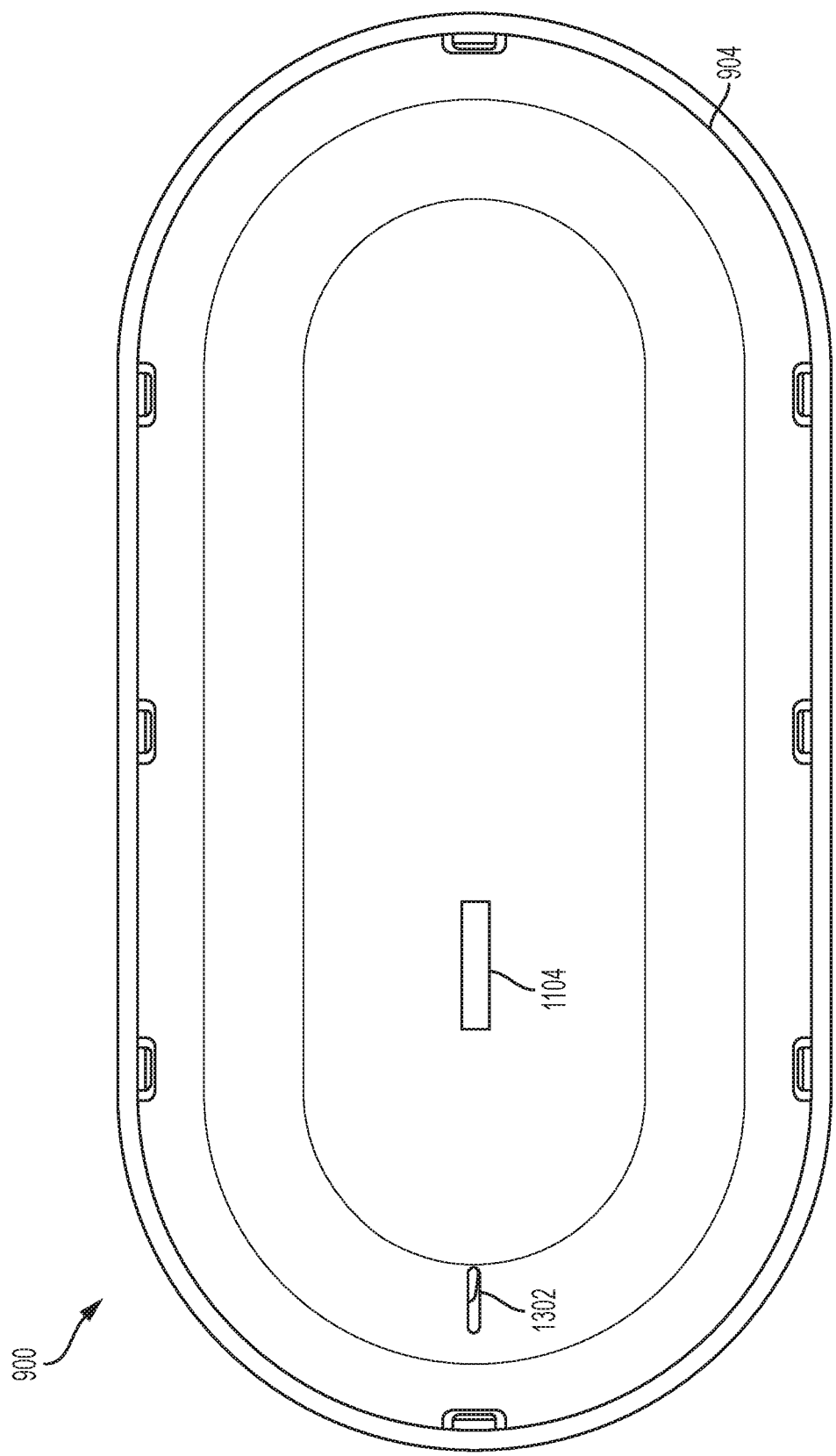
FIG. 13 illustrates a bottom view of the drug delivery device of FIG. 9.

FIG. 13 illustrates a bottom view of the drug delivery device 900. As shown in FIG. 13, the bottom portion 904 of the drug delivery device 900 can include an opening or a port 1302. The opening 1302 can correspond to the opening 702. A positioning of the on-body interlock 1104 is also shown in FIG. 13.

Figure 14:
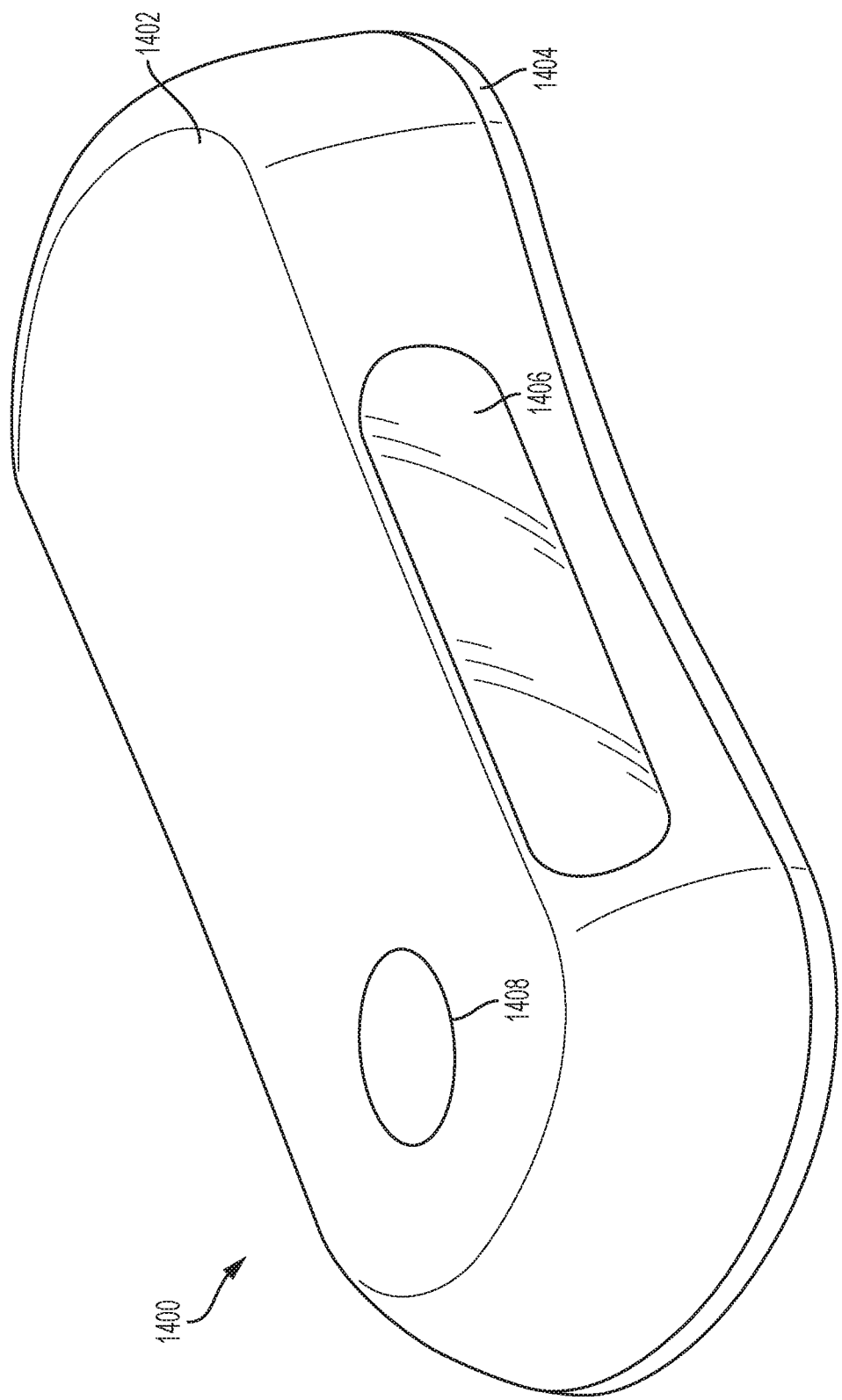
FIG. 14 illustrates a third exemplary embodiment of a drug delivery device.

FIG. 14 illustrates a third exemplary embodiment of a drug delivery device 1400. The drug delivery device 1400 can operate and provide substantially the same functionality as the drug device 100 and/or the drug delivery device 900. As shown in FIG. 14, the drug delivery device 1400 can include a top portion 1402 and a bottom portion 1404. The top portion 1402 and the bottom portion 1404 can together form a housing of the drug delivery device 1400. The top portion 1402 and the bottom portion 904 can be coupled together to form an outside of the drug delivery device 1400. The drug delivery device 900 can represent another design or form factor of the drug delivery device 100 and/or the drug delivery device 900.

The drug delivery device 1400 can include an opening or window 1406 that can expose a portion of a primary drug container and/or cartridge positioned within the drug delivery device 1400. The opening 1406 can correspond to the opening 906. The top portion 1402 can also include a patient interaction element or component 1408. In various embodiments, the patient interaction element 1408 can be a push button. In various embodiments, the patient interaction element 912 can correspond to the patient interaction element 108 and/or the patient interaction element 908. The drug delivery device 1400 can also include an on-body interlock positioned on an underside of the bottom portion 1404 (not shown in FIG. 14).

Figure 15:
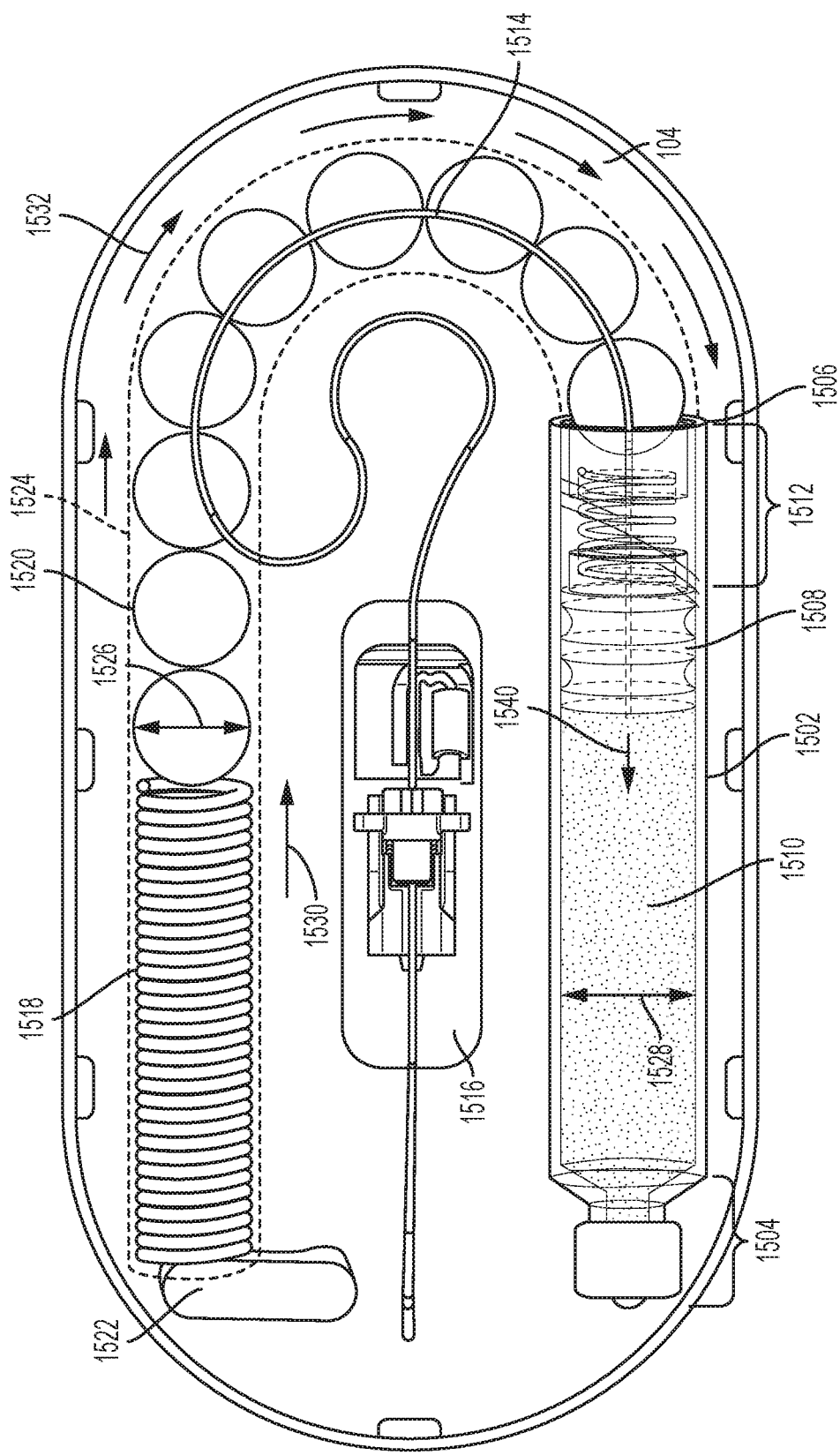
FIG. 15 illustrates a first exemplary arrangement of internal components of the drug delivery devices of FIGS. 1, 9, and 14.

FIG. 15 illustrates a first exemplary arrangement of internal components of the drug delivery device 100. For example, FIG. 15 shows various internal components of the drug delivery device 100 when the top portion 102 of the drug delivery device 100 is removed. The internal components shown in FIG. 15 can be substantially the same as and/or representative of the internal components of any other drug delivery devices disclosed herein including the drug delivery device 900 and the drug delivery device 1400. The arrangement and positioning of the internal components is not limited to that shown in FIG. 15.

Figure 41:
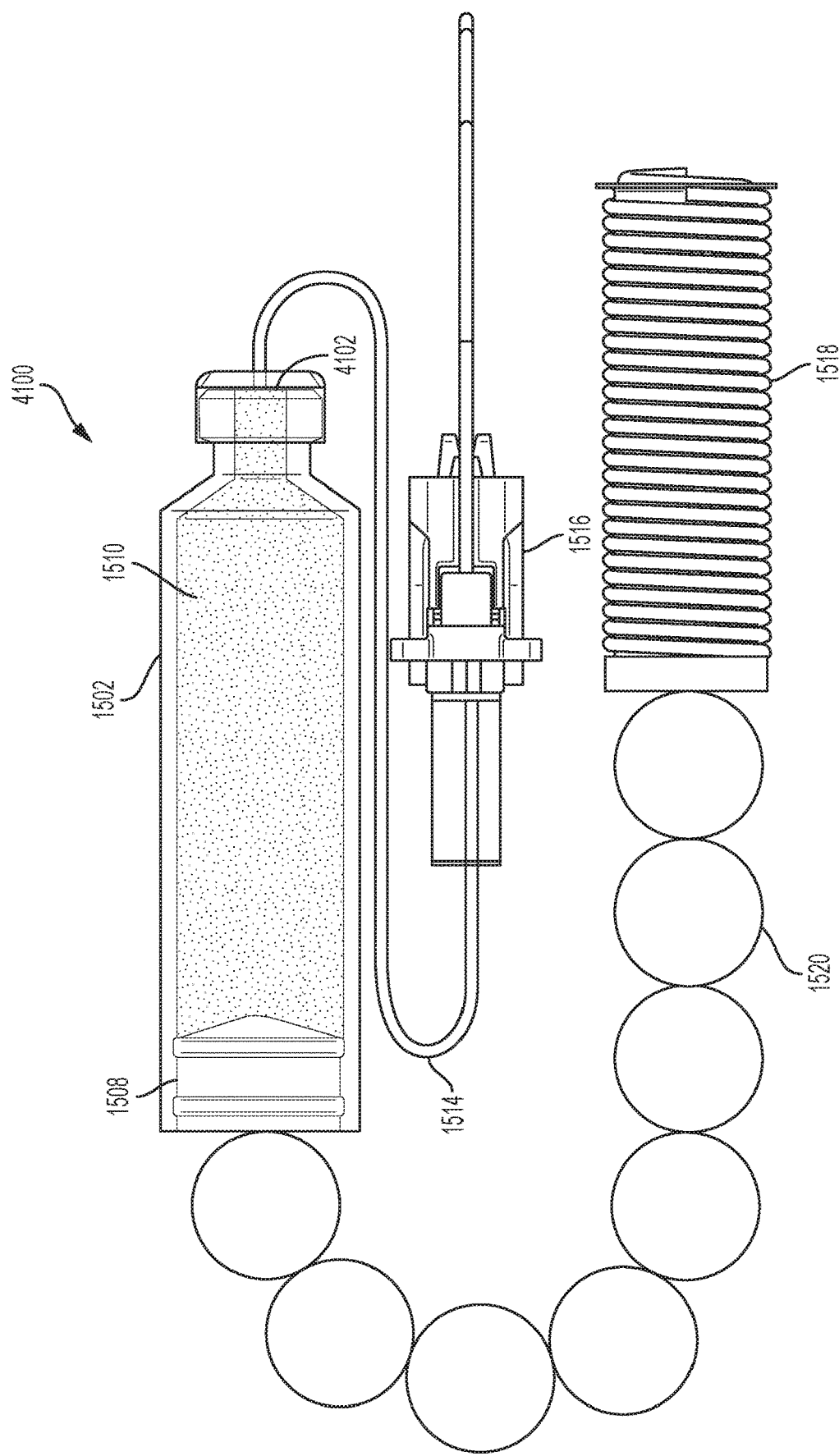
FIG. 41 illustrates an exemplary embodiment of an alternative routing of a needle conduit.

As shown in FIG. 15, the drug delivery device 100 can include a primary drug container 1502. The primary drug container 1502 can include a second end 1504 and a first end 1506. The primary drug container 1502 can be sealed at or near the second end 1504 and the first end 1506. The primary drug container 1502 can be formed from glass and/or plastic. The second end 1504 can include a neck and a cap as shown. The first end 1506 can include a plunger 1508. The plunger 1508 can be formed from a plastic material such as, for example, an elastomeric polymer material. A liquid drug 1510 can be contained between a sealing arrangement provided at the second end 1504 of the primary drug container 1502 and the plunger 1508. As an example, the second end 1504 of the primary drug container 1502 can be sealed by a septum (e.g., as shown in FIG. 41). The primary drug container 1502 of the drug delivery device 100 can be a drug cartridge such as, for example, an ISO standardized drug cartridge. The primary drug container 1502 can correspond to the primary drug container 202 described in relation to FIGS. 2 and 3.

The liquid drug 1510 contained within the primary drug container 1502 can be accessed through either the second end 1504 or the first end 1506. As shown in FIG. 15, the liquid drug 1510 is accessed through the first end 1506 of the primary drug container 1502. A primary drug container access mechanism or component 1512 can be positioned at or near the first end 1506 for accessing the liquid drug 1510. As shown in FIG. 15, the primary drug container access mechanism 1512 can access the liquid drug 1510 through the plunger 1508. The primary drug container access mechanism 1512 can include a needle or other component to pierce the plunger 1508 to access the liquid drug 1510. Prior to piercing the plunger 1508, the plunger 1508 can remain unpierced and the liquid drug 1510 inaccessible and sealed within the primary drug container 1502. The primary drug container access mechanism 1512 can remain in an idle state prior to being activated to access the liquid drug 1510. After activation, the needle of the primary drug container access mechanism 1512 can extend through the plunger 1508 as shown in FIG. 15.

The primary drug container access mechanism 1512 can couple the liquid drug 1510 to a needle conduit 1514. The needle conduit 1514 can include tubing (e.g., plastic tubing or metal tubing) and can provide a path for a portion of the liquid drug 1510 that is expelled from the primary drug container 1502. The primary drug container access mechanism 1512 can correspond to the primary drug container access mechanism 204 described in relation to FIGS. 2 and 3. The needle conduit 1514 can correspond to the needle conduit 206 described in relation to FIGS. 2 and 3. In various embodiments, the needle used to pierce the plunger 1508 can be a part of the needle conduit 1514 as opposed to a portion of the primary drug container access mechanism 1512.

In various embodiments, the liquid drug 1510 can be accessed through the second end 1504 of the primary drug container 1502. In various embodiments, the primary drug container access mechanism 1512 can be positioned at or near the second end 1504 along with the needle conduit 1514.

As shown in FIG. 15 and described herein, the liquid drug 1510 stored in the primary drug container 1502 can be accessed through the primary drug container access mechanism 204 without having to move the primary drug container 1502.

The needle conduit 1514 can route the liquid drug 1510 from the primary drug container 1502 to a needle insertion mechanism or component 1516. The needle insertion mechanism 1516 can provide an entry point to a patient. The needle insertion mechanism 1516 can include a hard needle and/or a soft needle or cannula that provides access to the patient such that the liquid drug 1510 can be delivered to the patient. The needle insertion mechanism 1516 can correspond to the needle insertion mechanism 208 described in relation to FIGS. 2 and 3.

As further shown in FIG. 15, the drug delivery device 100 can include a drive spring 1518 and a number of spherical elements or components 1520 (e.g., a plurality of spherical elements or spheres 1520). The spherical elements 1520 can be referred to as spherical energy transfer elements or components, or force transfer spheres. As used herein, the spherical elements 1520 can be referenced using any of these terms including, for example, spheres 1520. In various embodiments, the spheres 1520 can be ball bearings. The spheres 1520 can be formed of any type of material including glass, metal (e.g., stainless steel), or a polymer or other plastic.

The drive spring 1518 and the spheres 1520 can be used to expel the liquid drug 1510 from the primary drug container 1502. In particular, the drive spring 1518 can apply a force that can be applied to the spheres 1520. The spheres 1520 can be arranged to transfer the force from the drive spring 1518 to the plunger 1508. When the force from the drive spring 1518 is applied to the plunger 1508, the plunger 1508 can advance into the primary drug container 1502 (toward the second end 1504). As the plunger 1508 advances into the primary drug container 1502, the liquid drug 1510 within the primary drug container 1502 can be forced out of the primary drug container 1502 into the needle conduit 1514 and on to the needle insertion mechanism 1516 for delivery to the patient. In particular, as the plunger 1508 is moved toward to the second end 1504, the liquid drug 1510 can be forced out of the primary drug container 1502 through the plunger 1508 on to the needle conduit 1514. Accordingly, in various embodiments, the liquid drug 1510 can be expelled from the primary drug container 1502 in a direction that is approximately opposite to a direction of movement of the plunger 1508 as the plunger 1508 is moved toward the second end 1504.

The drive spring 1518 can be any type of spring. The drive spring 1518 can have any desired spring constant value, k. The drive spring 1518 is not limited to a single spring and can include one or more springs. In various embodiments, the drive spring 1518 can include one or more compression springs and/or torsion springs. For example, the drive spring 1518 can include one or more linear compression springs arranged in a parallel arrangement, a series arrangement, an arrangement of nested springs in series, or any combination thereof. In various embodiments, the drive spring 1518 can be implemented as double series springs. A dead bolt 1522 or other fixed element can be positioned at one end of the drive spring 1518. The dead bolt 1522 can provide a stable reference for the drive spring 1518 (e.g., a push off point). The dead bolt 1522 can be considered a thrust point for the drive spring 1518 (e.g., a force reactionary "thrust point"). The dead bolt 1522 can be considered to be or can represented a fixed component that can be coupled to the inner top surface of the lower portion 104. The fixed component 1522 can be positioned at an end of the drive spring 1518.

As shown in FIG. 15, the drive spring 1518 can be directly coupled to the spheres 1520. In various embodiments, the drive spring 1518 can include a fixed component or plate coupled to an end of the drive spring 1518. The fixed component can have a width that is substantially the same as the width of the coils of the coils of the drive spring 1518. The fixed component can be substantially flat and can be directly coupled to the spheres 1520 (e.g., the sphere 1520 positioned furthest from the plunger 1508 along the path of the spheres 1520.

The bottom portion 104 can include a track 1524 for guiding the spheres 1520. The track 1524 can be considered to be a guide, tube, or housing. In various embodiments, the drive spring 1518 and the spheres 1520 can be positioned within the track 1524. The track 1524 can completely surround or cover the drive spring 1518 and/or the spheres 1520. The track 1524 can be formed of any type of material including, for example, a plastic material or metal (e.g., stainless steel), or any combination thereof. For example, an outer portion of the curved portion of the track 1524 may be formed of a metal while an inner portion of the curved portion of the track may before formed of a hard plastic. The track 1524 can form any shape and can be arranged to take on any shape to guide the spheres 1520 from the drive spring 1518 to the cartridge 1502. In various embodiments, a first end of the track 1524 can be positioned adjacent to the dead bolt 1522 and a second end of the track 1524 can be positioned approximately adjacent to the first end 1506 of the cartridge. The first end of the track 1524 can be closed while the second end of the track 1524 can be open, to allow the spheres 1520 to exit the track 1524 and to enter the primary drug container 1502 as shown in FIG. 15. The track 1520 can provide a support or guide for the drive spring 1518. This can increase the efficiency of the drug delivery device 100 as the drive spring 1518 can be prevented from buckling or deforming during expansion (e.g., when the drug delivery device 100 is in motion due to movement of the patient).

In various embodiments, the track 1524 can cover any portion of the drive spring 1518 (e.g., less than the entirety of the drive spring 1518). In various embodiments, the track 1524 can have any cross-sectional shape. For example, the track 1524 can have a circular cross-sectional shape. Overall, the track 1524 can provide a desired arrangement and/or alignment of the spheres 1510 relative to the drive spring 1518 and the primary drug container 1502. Further, the track 1524 can ensure that the spheres 1520 are moved toward the cartridge 1502 by the drive spring 1518. In various embodiments, the drive spring 1518 can be extend into the primary drug container 1502.

The spheres 1520 can be arranged between the drive spring 1518 and the primary drug container 1502. In various embodiments, the spheres 1520 can be positioned adjacent to the primary drug container 1502, the primary drug container access mechanism 1512, and/or the plunger 1508. The spheres 1520 can be arranged to follow any path or route (e.g., as determined by the track 1524). The spheres 1520 can be considered as forming a ball chain. As an alternative to the spheres 1520, or in addition thereto, the drive mechanism 210 of a drug delivery device described herein can include chains, linkages, or other flexible or semi-flexible elements or components for translating a force form a source (e.g., the drive spring 1518) to the plunger 1508. In various embodiments, one or more rigid elements can be used transfer a force to the plunger 1508. In general, any combination of spheres 1520, flexible, semi-flexible, and/or rigid elements can be used to transfer a force to the plunger 1508.

Prior to activation, the drive spring 1518 can remain in an idle state. While in an idle state, the drive spring 1518 can be compressed (e.g., as shown in FIG. 15). When activated, the drive spring 1518 can be allowed to expand. For example, after activation, the drive spring 1518 can be allowed to expand in a direction away from the dead bolt 1522. The drive spring 1518 can be allowed to fully expand at one time or can be incrementally expanded so as to apply a force to the plunger 1508 through the spheres 1520 in an incremental manner. When initially activated, the drive spring 1518 can apply a force that enables the primary drug container access mechanism 1512 to access the liquid drug 1510. For example, the drive spring 1518 can apply a force that enables the primary drug container access mechanism 1512 to cause a needle coupled to the needle conduit 1514 to pierce the plunger 1508. The drive spring 1518 and the spheres 1520 can together correspond to the drive mechanism described in relation to FIGS. 2 and 3.

Once the plunger 1508 is pierced, the primary drug container 1502 can be drained of its contents and delivered to a patient. The liquid drug 1510 contained in the primary drug container 1502 can be drained at any desired rate over any amount of time over one or more doses. The liquid drug 1510 can be expelled from the primary drug container 1502 at one time (e.g., for a single dose delivery) or can be expelled over a series of start and stop intervals (e.g., for multiple dose delivery). The spheres 1520 and track 1524 can be used to transfer energy stored by the drive spring 1518 to the plunger 1508. Accordingly, the drive spring 1518 can be considered to be an energy storage mechanism or component and the spheres 1520 can be considered to be an energy transfer mechanism or component. The drive mechanism of the drug delivery device 100 can therefore be considered to include both an energy storage mechanism or component and an energy transfer mechanism or component. Any number of spheres 1520 can be used between the drive spring 1518 and the primary drug container 1502.

The drive spring 1518 and the spheres 1520 can be selected and adjusted to help regulate a flow of the liquid drug 1510 from the primary drug container 1502 to the needle insertion mechanism 1516 based on a variety factors including the viscosity of the liquid drug 1510. The needle conduit 1514 can be arranged as shown in FIG. 15 to provide a service loop that allows flexing to improve delivery and flow of the liquid drug 1510 to the patient.

In general, the drug delivery devices described herein can operates as follows. The plunger 1508 can be moved toward the second end 1504 of the primary drug container 1502 to expel the liquid drug 1510 from the primary drug container 1502. The liquid drug 1510 expelled from the primary drug container 1502 can be provided to a needle conduit 1514. The needle conduit 1514 can be coupled to a needle insertion mechanism 1516 that can provide an access point to the patient. The needle conduit 1514 can be coupled to the plunger 1518 or can be coupled to a septum of the primary drug container 1502. The flow (e.g., speed) of the liquid drug 1510 can be determined by a variety of factors including a viscosity of the liquid drug 1510, a length and size (e.g., internal diameter) of the needle conduit 1514 and any fluid path portion of the needle mechanism 1516, and the force provided by the drive spring 1518. Given a viscosity of for a particular liquid drug 1510, the force provided by the drive spring 1518 as well as parameters of the fluid path (e.g., length and width of the provided fluid path through the needle conduit 1514) can be tuned or adjusted to provide a desired flow rate. In particular, a desired flow rate of the liquid drug 1510. In this way, a particular liquid drug 1510 can be delivered to the patient over a desired amount of time. In various embodiments, flow restrictions can be add to the fluid path (e.g., along any portion of the needle conduit 1514) to adjust flow of the liquid drug 1541 as desired. The force of the spring 1518 can be determined by the size and arrangement of the one or more springs used for the drive spring 1518 including the spring constants of the one or more springs.

In various embodiments, the drive spring 1518 can be maintained in a compressed state prior to activation. Once activated, the drive spring 1518 can be allowed to expand and apply a force to the one or more spheres 1520. An initial force provided by the drive spring 1518 can cause the primary drug container access mechanism 1512 to access the primary drug container 1502. Specifically, the primary drug container access mechanism 1512 can couple the liquid drug 1510 to the needle conduit—for example, by forcing a needle of the needle conduit 1514 to pierce the plunger 1518.

To provide the liquid drug 1510 to the patient in a single dose, the drive spring 1518 can be allowed to expand fully in substantially one motion over a desired period of time. In doing so, the liquid drug 1510 can be expelled from the primary drug container 1502 substantially continuously. To provide the liquid drug 1510 to the patient over two or more doses, application of the force from the drive spring 1518 to the plunger 1508 can be interrupted. For example, the drive spring 1518 can be prevented from expanding and/or the spheres 1520 can be held back from advancing. By applying and interrupting the force from the drive spring 1518 to the plunger 1508, the liquid drug 1510 can be delivered to the patient in multiple discrete amounts, thereby providing multiple doses of the liquid drug 1510 to the patient over time. The needle insertion mechanism 1516 and/or the needle conduit 1514 can also block the flow of the liquid drug 1510 when desired to enable the liquid drug 1510 to be delivered to the patient over multiple doses.

The spheres 1520 can provide efficient energy transfer from the drive spring 1518 to the plunger 1508 due in part to the spheres 1520 providing point to point contact to one another. This point to point contact can introduce less friction into a drive system than a drive system that relies on line to line contact between elements for transferring energy. Further, the drive mechanism of the drug delivery device 100 enables energy to be transferred in a different direction than the energy is initially provided. For example, as shown in FIG. 15, the energy stored by the drive spring 1518 can be transferred around a tight radius of curvature by the spheres 1520 (e.g., around a corner or 180 degrees from the where the energy is first directed as shown by the exemplary arrangement of the track 1524). This enables the drug delivery device 100 to remain small and compact.

As shown in FIG. 15, a force can be provided by the drive spring 1518 when it is allowed to expand. The force provided by the drive spring 1518 can be applied in a direction 1530 toward the spheres 1520. The direction 1530 can correspond to a direction in which the drive spring 1518 is allowed to expand, based on a positioning of the dead bolt 1522, which can provide a thrust point for the drive spring 1518. With reference to the arrangement of the components shown in FIG. 15, the direction 1530 of the force provided by the drive spring 1518 can be from the dead bolt 1522 to the spheres 1520. The spheres 1520 can translate or transfer the force from the drive spring 1518 to the plunger 1508. The spheres 1520 allow the force to be translated to a different direction than the original direction of the force. Specifically, the spheres 1520 can apply the force in a direction toward the second end 1504 of the primary drug container 1502 relative to the first end 1506 of the primary drug container 1502. Consequently, the spheres 1520 enable the force provide by the drive spring 1518 provided in a first direction to be applied to the plunger 1508 in a second, approximately opposite direction.

In particular, as shown in FIG. 15, the direction 1530 of the force provided by the drive spring 1518 can cause the spheres 1520 to move in the direction 1532—that is, through the track 1524 toward the first end 1506 of the primary drug container 1502 (e.g., clockwise). The spheres 1520 can therefore transfer the force from the drive spring 1518 to the plunger 1508, thereby causing the plunger 1508 to move in a direction 1540. The movement of the plunger 1508 in the direction 1540 can force the liquid drug 1510 out of the primary drug container 1502 and into the needle conduit 1514.

Further, the spheres 1520 enable the plunger 1508 to move in a first direction from the first end 1506 of the primary drug container 1502 to the second end 1504 of the primary drug container 1502. In doing so, the plunger 1508 can force, expel, or push the liquid drug 1510 out of the primary drug container 1502 through the needle conduit 1514. As shown in FIG. 15, the needle conduit 1514 can be directly coupled to the plunger 1508. As a result, the liquid drug 1510 can be expelled from the primary drug container 1502 in a direction approximately opposite to a direction of the movement of the plunger 1508 toward the second end 1504 of the primary drug container 1502. The direction of the expelled liquid drug 1510 is approximately the same direction as the direction of the force provided by the drive spring 1518.

In general, the drug delivery device 100, and any other drug delivery device described herein, can generate a force in a first direction (e.g., the direction 1530 based on the drive spring 1518) and can apply the force in a second, opposite direction (e.g., the direction 1540 based on the spheres 1520) to expel the liquid drug 1510 from a primary drug container 1502 in a precise and controlled manner. The direction 1540 need not be opposite to the direction 1530. That is, in various embodiments, the direction 1540 of the force applied to the plunger 1508 by the spheres 1520 can be in any direction relative to the direction 1530 of the force provided by the drive spring 1518.

Further, in various embodiment, the liquid drug 1510 can be expelled from either end of the primary drug container 1502. This enables the components of the drug delivery device 100 (as shown in FIG. 15) to be arranged in a close and tight manner, allowing the drug delivery device 100 to remain small and compact. In turn, the drug delivery device 100 can be more comfortable to wear and less cumbersome to the patient.

The drive spring 1518 and the spheres 1520 can be operated to enable any number of spheres 1520 or any portion of a single sphere 1520 to advance the plunger 1508. In various embodiments, one stroke of delivery of the liquid drug 1510 can correspond to one sphere 1520. For example, the width or diameter 1526 of one sphere 1520 can correspond to one stroke of liquid drug 1510 delivery. In various embodiments, the widths 1526 of the spheres 1520 can all be approximately equal. By controlling the number of spheres 1520 or portion of any one sphere 1520 that can be advanced into the primary drug container 1502 to push on the plunger 1508, the drug delivery device 100 can provide the liquid drug 1510 to a patient in a single dose or over multiple doses.

As shown in FIG. 15, the primary drug container 1502 can have an inner diameter 1528 (and an outer diameter; not shown in FIG. 15 for simplicity). The inner diameter 1528 of the primary drug container 1502 can be slightly larger than the diameter of the spheres 1520, thereby allowing the spheres 1520 to fit inside of the primary drug container 1502. Further, the track 1524 can have an inner diameter (not shown in FIG. 15 for simplicity) that is also slightly larger than the diameter 1526 of the spheres 1520, to also allow the spheres 1520 to move through the interior of the track 1524.

In various embodiments, the needle conduit 1514 can be a needle formed from plastic or metal, or a combination thereof. As shown in FIG. 15, an end of the need conduit 1514 that can be coupled to the liquid drug 1510 can be a hard end of the needle conduit 1514 while the portion of the needle conduit 1514 routed toward the needle mechanism 1516 can be a soft portion of the needle conduit 1514.

Figure 16:
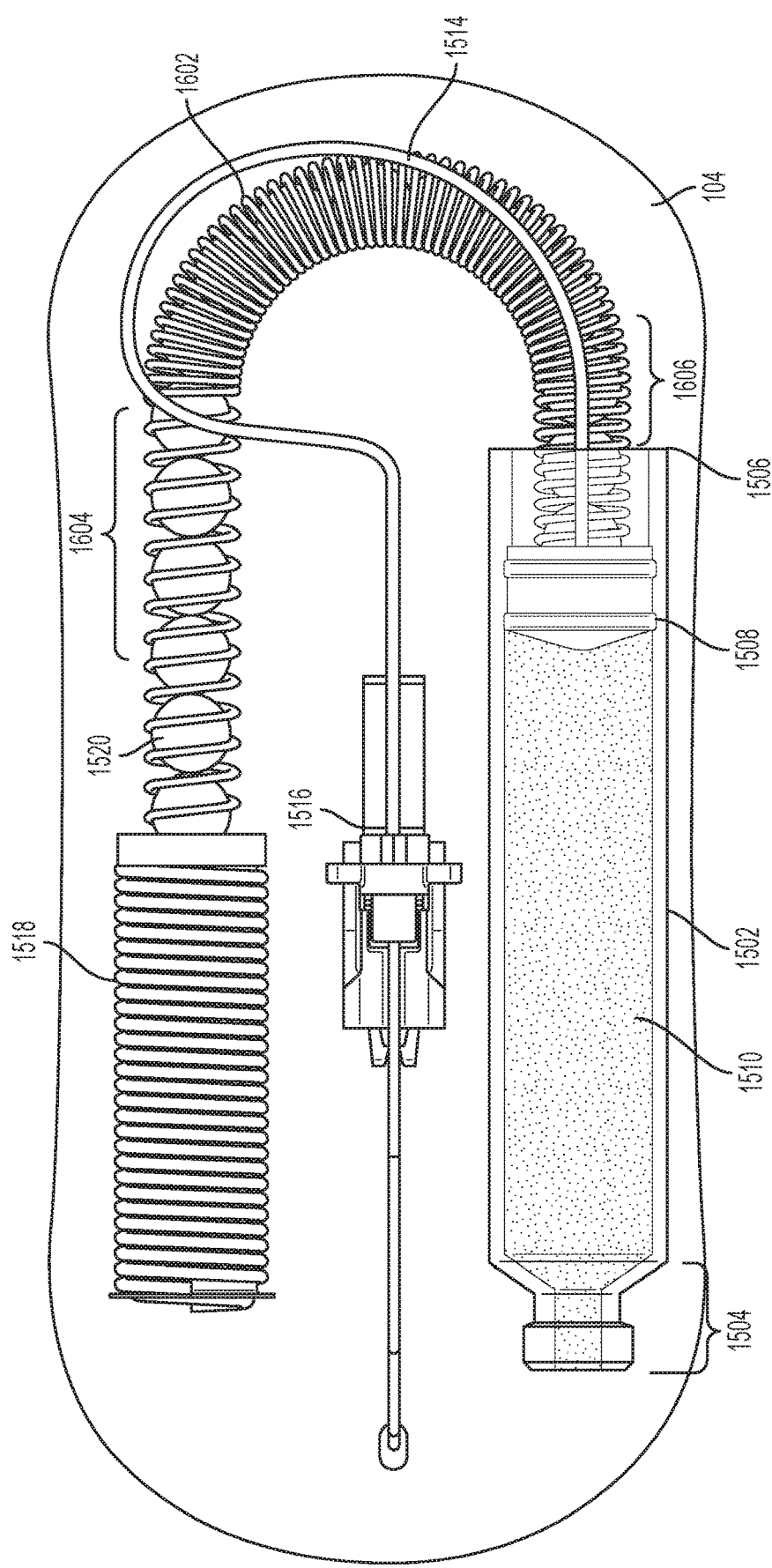
FIG. 16 illustrates a second exemplary arrangement of internal components of the drug delivery devices of FIGS. 1, 9, and 14.

FIG. 16 illustrates a second exemplary arrangement of internal components of the drug delivery device 100. For example, FIG. 16 shows various internal components of the drug delivery device 100 when the top portion 102 of the drug delivery device 100 is removed. The internal components shown in FIG. 16 can be substantially the same as and/or representative of the internal components of any other drug delivery devices disclosed herein including the drug delivery device 900 and the drug delivery device 1400. The arrangement and positioning of the internal components is not limited to that shown in FIG. 16.

As shown in FIG. 16, the drug delivery device 100 includes a guide 1602. The guide 1602 can be a spring or coil guide. The guide 1602 can be formed of any material including plastic or metal. The guide 1602 can contain and provide a route or an alignment for the spheres 1520. The guide 1502 can be positioned between the drive spring 1518 and the primary drug container 1502. The guide 1602 can extend into the primary drug container 1502 to enable the spheres 1520 to make contact with the plunger 1508 as the drug delivery device 100 operates to deliver the liquid drug 1510 to the patient. Accordingly, in various embodiments, the guide 1502 can apply a force to the plunger 1508. In various other embodiments, the guide 1602 does not apply any force to the plunger 1508 and instead maintains an alignment and routing of the spheres 1520.

As shown in FIG. 16, the guide 1502 can include a first region 1604 and a second region 1606. When the drive spring 1518 is allowed to expand, the first region 1604 can be driven forward and can begin to collapse. The second region 1606 can begin to expand as the plunger 1508 is moved forward toward the second end 1504 of the primary drug container 1502. Accordingly, portions of the guide 1602 can be allowed to expand or compress as appropriate based on its positioning relative to the drive spring 1518 and the plunger 1508 and based on the expanded state of the drive spring 1518.

FIGS. 15 and 16 show the liquid drug 1510 of the primary drug container 1502 as accessible through the plunger 1508. In various embodiments, the liquid drug 1510 of the primary drug container 1502 can be accessed through the second end 1504 of the primary drug container 1502, which may include or may be referred to as the "septum" (e.g., as depicted and described in relation to FIG. 41). In various embodiments, the primary drug container access mechanism 1512 can be positioned at or near the second end 1504 of the primary drug container 1502. The primary drug container access mechanism 1512 can access the liquid drug 1510 through a septum positioned at or near the second end 1504 of the primary drug container 1502. In various embodiments, the primary drug container 1502 can be held in a stationary position and the primary drug container access mechanism 1512 can be moved relative to the primary drug container 1502 to pierce the septum. In various embodiments, the primary drug container access mechanism 1512 can be held in a stationary position and the primary drug container 1502 can be moved relative to the primary drug container access mechanism 1512 to pierce the septum. Under either scenario, a force provided by the drive spring 1518 can cause the septum to be pierced, thereby coupling the liquid drug 1510 to the needle conduit 1514. As shown in FIG. 16, the drive spring 1518 is shown with the fixed component or plate positioned at an end of the drive spring 1518 and directly coupled to the spheres 1520. In various embodiments, the drive spring 1518 as illustrated can be used as the drive spring 1518 depicted in FIG. 15.

The various internal components of the drug delivery device 100 depicted in FIGS. 15 and 16 can be mechanically operated and controlled or can be electromechanically operated and controlled. In various embodiments, the internal components of the drug delivery device 100 depicted in FIGS. 15 and 16 can be operated to deliver the liquid drug 1510 to the patient in a single dose. In various embodiments, the internal components of the drug delivery device 100 depicted in FIGS. 15 and 16 can be operated to deliver the liquid drug 1510 to the patient in two or more doses (e.g., in multiple doses).

To provide the liquid drug 1510 across multiple doses, the flow of the liquid drug 1510 can be stopped or interrupted such that it does not flow out of the primary drug container 1502, through the needle conduit 1514, and/or through the needle insertion mechanism 1516. In general, multiple doses can be provided by interrupting the flow of the liquid drug 1510 from the primary drug container 1520. The flow of the liquid drug 1510 can be interrupted by removing the force applied to the plunger 1508 that can push the liquid drug 1510 out of the primary drug container 1502. The force applied to the plunger 1508 can be interrupted by retaining the drive spring 1518 and/or by retaining the spheres 1520 from applying any translated force from the drive spring 1518 to the plunger 1508. By alternatively applying and interrupting the force applied to the plunger 1508, the drug delivery device 100 can provide the liquid drug 1510 to the patient over multiple doses.

Figure 17:
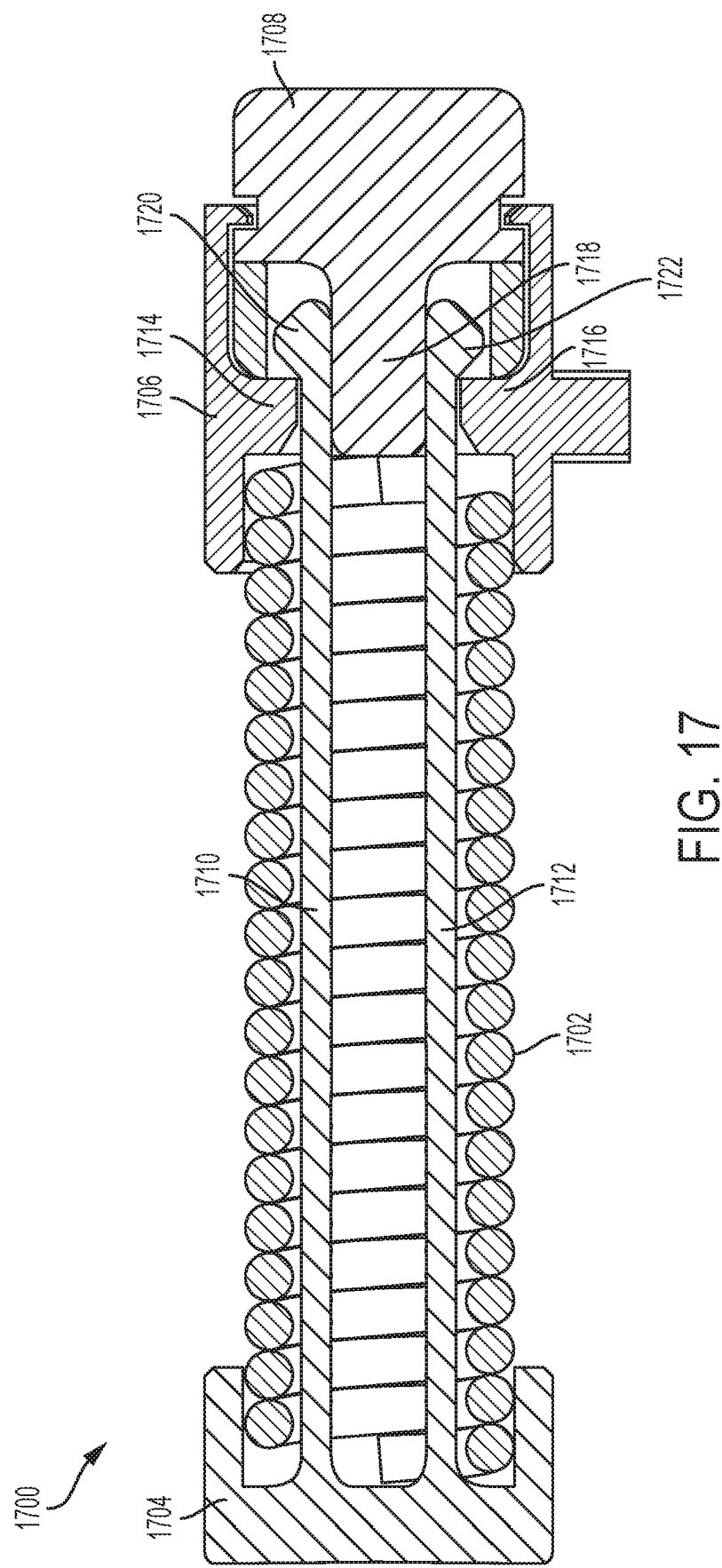
FIG. 17 illustrates an exemplary drive spring release mechanism in a first state.

FIG. 17 illustrates an exemplary drive spring release mechanism or component 1700. The drive spring release mechanism 1700 can include a drive spring 1702, a tension member 1704, a spring retainer 1706, and a release cam 1708. The drive spring 102 can correspond to or represent the drive spring 1518 depicted, for example, in FIGS. 15 and 16. FIG. 17 illustrates a cross-sectional view of the drive spring release mechanism 1700. The drive spring release mechanism 1700 can be a component of the drive mechanism 210 depicted in FIGS. 2 and 3.

FIG. 17 shows the drive spring release mechanism 1700 in a first state or locked state with the drive spring 1702 in a compressed state. The tension member 1704 and the spring retainer 1706 can prevent the drive spring 1702 from extending in a direction towards the tension member 1704 relative to a positioning of the spring retainer 1706. The tension member 1704 can include a first arm or extension 1710 and a second arm or extension 1712. The first and second extensions 1710 and 1712 can extend from a first end or base end of the tension member 1704 through a center portion of the drive spring 1702. The first and second extensions 1710 and 1712 can extend beyond an end of the drive spring 1702.

A first end 1720 of the first extension 1710 can be retained in place as shown by the spring retainer 1706. Similarly, a second end 1722 of the second extension 1712 can also be retained in place as shown by the spring retainer 1706. Specifically, the spring retainer 1706 can include a first portion 1714 positioned between the end of the drive spring 1702 (e.g., a top or first end) and the end 1720 of the first extension 1710. Similarly, the spring retainer 1706 can include a second portion 1716 positioned between the end of the drive spring 1702 (e.g., a bottom or second end) and the end 1722 of the second extensions 1712. The first end 1720 and the second end 1722 can be considered to be lips or traverse extensions of the first and second extensions 1710 and 1712, respectively.

The release cam 1708 can have a first portion 1718 positioned between the first portion 1714 and the second portion 1716 of the spring retainer 1706. The first portion 1714 of the spring retainer 1706 and the first portion 1718 of the release cam 1708 can retain the end 1720 of the first extension 1710 of the tension member 1704 as shown. Specifically, the first portion 1714 of the spring retainer 1706 and the first portion 1718 of the release cam 1708 can prevent the end 1720 of the first extension 1710 from moving away from the release cam 1708 towards the drive spring 1702. Similarly, the second portion 1716 of the spring retainer 1706 and the first portion 1718 of the release cam 1708 can prevent the end 1722 of the second extension 1712 from moving away from the release cam 1708 towards the drive spring 1702. Accordingly, the first and second extensions 1710 and 1712 can be maintained a distance apart from each other so that the respective lips 1720 and 1722 disposed on the extensions 1710 and 1712 interfere with the first and second portions 1714 and 1716, respectively.

The end 1720 of the first extension 1710 can be thicker or wider than the portion of the first extension 1710 that is positioned in a center or middle of the drive spring 1702 (e.g., to form a lip or traverse extension as described above). As a result, the first portion 1714 of the spring retainer 1706 and the first portion 1718 of the release cam 1708 can retain the first portion 1714 of the spring retainer 1706 as shown. Similarly, the end 1722 of the second extension 1712 can be thicker or wider than the portion of the second extension 1712 that is positioned in a center or middle of the drive spring 1702 such that the second portion 1716 of the spring retainer 1706 and the first portion 1718 of the release cam 1708 can retain the second portion 1712 of the spring retainer 1706. The drive spring release mechanism 1700 can maintain the drive spring 1702 in a compressed or locked state as shown in FIG. 17 until activated—for example, by a patient input.

Figure 18:
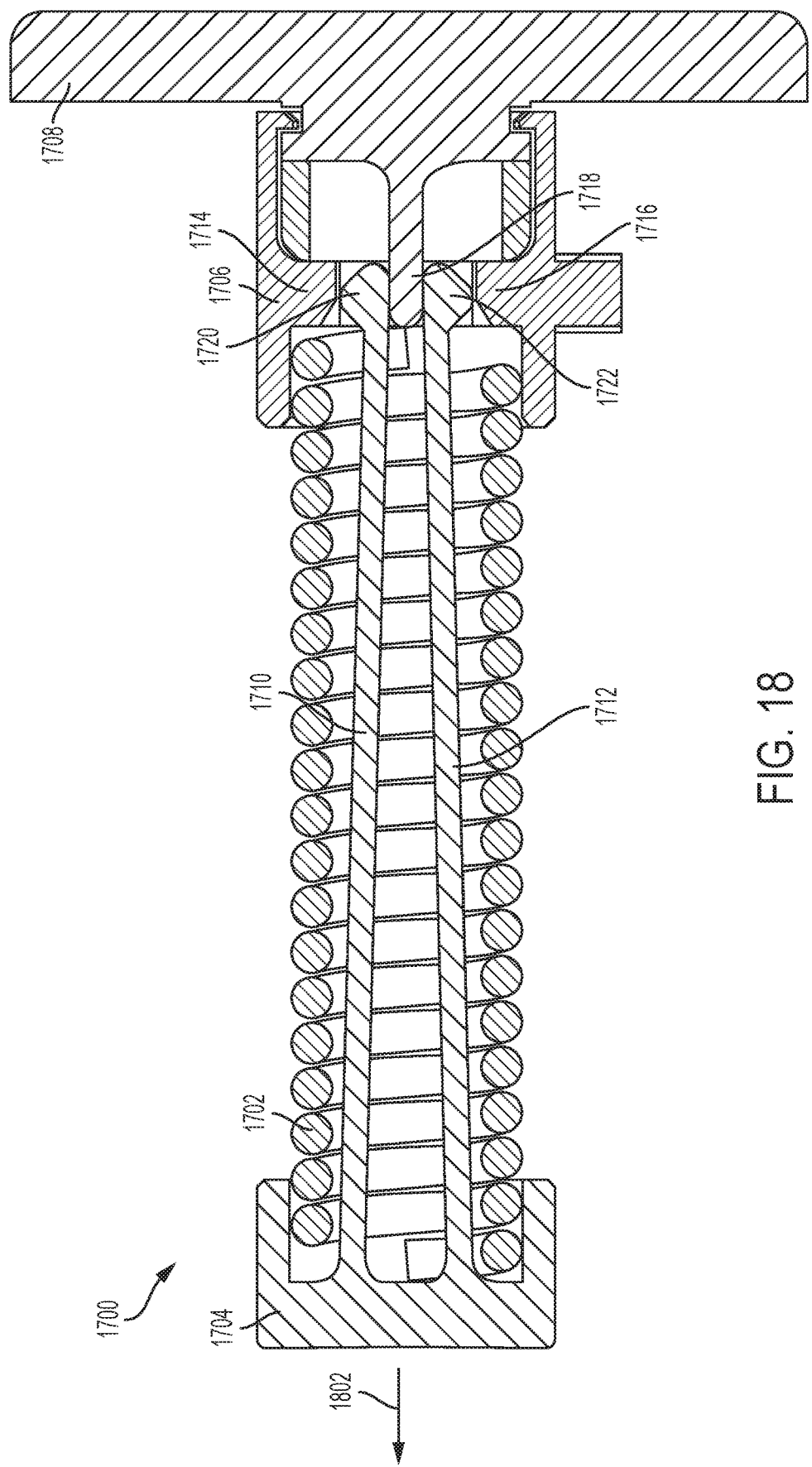
FIG. 18 illustrates the exemplary drive spring release mechanism of FIG. 17 in a second state.

FIG. 18 illustrates the drive spring release mechanism 1700 in a second state or released state (also in cross-section). To release the drive spring 1702 so that it can expand, the release cam 1708 can be rotated. For example, the release cam 1708 can be rotated about an axis that is approximately parallel and/or coaxial to an axis of the drive spring 1702. The first portion 1718 of the release cam 1708 can have a variable width such that the first portion 1718 has a narrower width when the release cam 1708 is rotated to release the drive spring 1702. As shown in FIG. 18, the narrow width or thickness of the first portion 1718 of the release cam 1708 allows the end 1720 of the first extension 1710 of the tension member 1704 to move away from the release cam 1708 toward the second extension 1712 and under the first portion 1714 of the spring retainer 1706. Similarly, the end 1722 of the second extension 1712 of the tension member 1704 is also allowed to move away from the release cam 1708 toward the first extension 1710 and over the second portion 1716 of the spring retainer 1706.

When the first extension 1710 of the tension member 1704 is able to move under the first portion 1714 of the spring retainer 1706 and the second extension 1712 of the tension member 1704 is able to move over the second portion 1716 of the spring retainer 1706, the base portion of the tension member 1704 located on an end of the drive spring 1702 can no longer maintain the drive spring 1702 in a compressed state. Accordingly, the drive spring 1702 is allowed to expand in a direction away from the release cam 1708 as shown by a direction of movement indicator 1802. The tension member 1704 and the drive spring 1702 can be allowed to move in substantially the same direction away from the release cam 1708. In various embodiments, the tension member 1704 can be coupled to the spheres 1520 illustrated in FIGS. 15 and 16. The movement of the tension member 1704 and the drive spring 1702 can apply a force to the spheres 1520, thereby causing the plunger 1508 to advance into the primary drug container 1502 to expel the liquid drug 1510.

In various embodiments, the release cam 1708 may be mechanically actuated. For example, the release cam 1708 can be mechanically actuated by a patient applying a direct rotational force to the release cam 1708. In various other embodiments, the release cam 1708 can be mechanically actually by a patient by applying a rotational force indirectly—for example, by a linkage. In various embodiments, the release cam 1708 may be electromechanically actuated—for example, by a motor or any other appropriate manner as will be appreciated by one of ordinary skill in the art.

Figure 19:
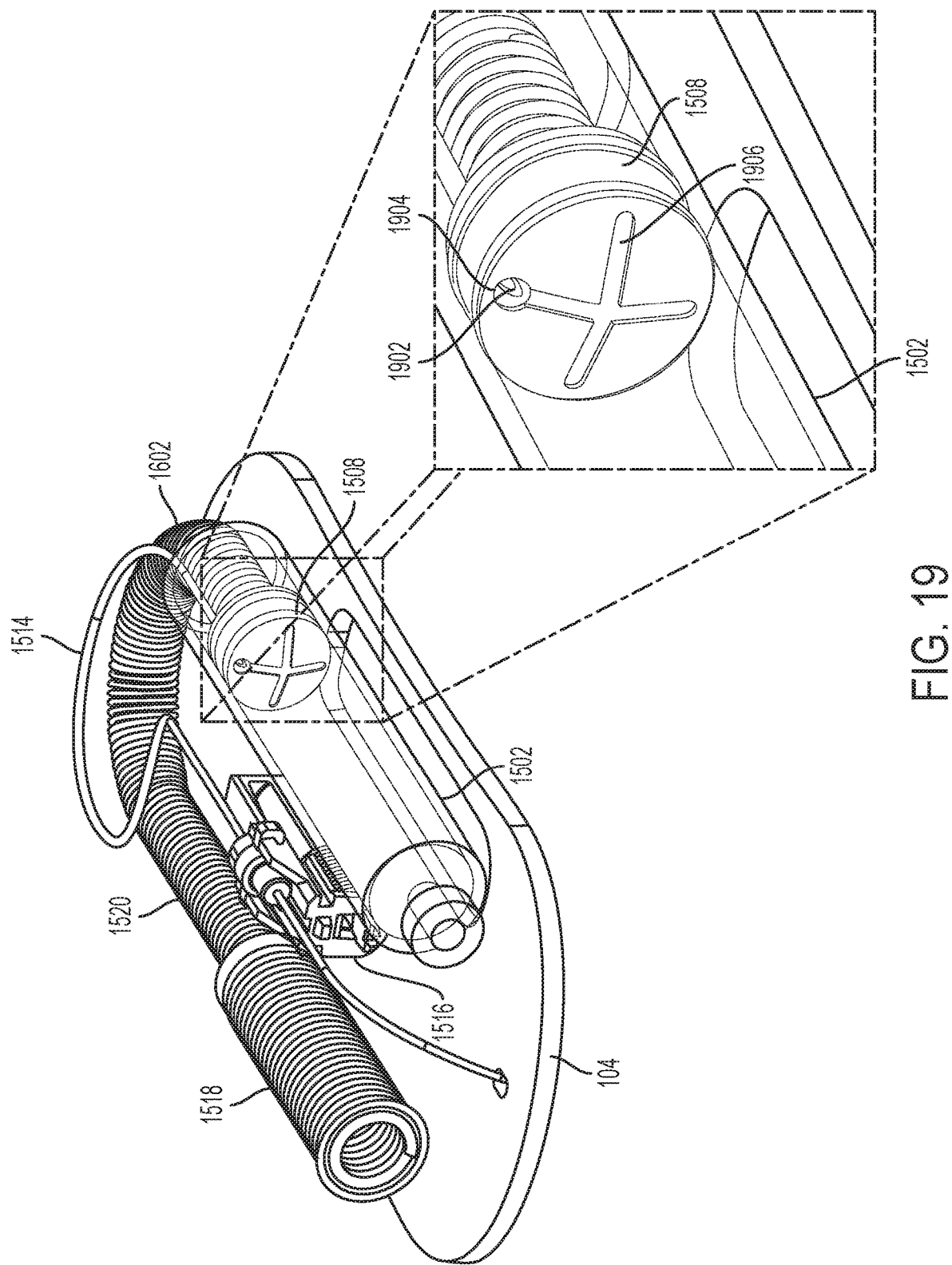
FIG. 19 illustrates an exemplary mechanism for accessing a liquid drug stored in a drug cartridge.

FIG. 19 illustrates an exemplary mechanism for accessing a liquid drug stored in a drug cartridge. In relation to the internal components of the drug delivery device 100 depicted in FIG. 16, FIG. 19 shows a first view of the drug delivery device 100 and close-up view of the interaction between the plunger 1508 and the primary drug container 1502. The mechanism depicted in FIG. 19 can be used or included within any of the drug delivery devices described herein.

As mentioned, the plunger 1508 can be pierceable. For example, the plunger 1508 can be pierceable by a hard needle 1902 coupled to the needle conduit 1514. The hard needle 1902 can be coupled to an end of the needle conduit 1514. An initial force provide by the drive spring 1518 when the drive spring 1518 is initially released can provide a force to enable the hard needle 1902 to pierce the plunger 1508 and extend into the primary drug container 1502. The hard needle 1902 can extend into the primary drug container 1502 through an inlet or opening 1904 formed when the hard needle 1902 is pressed against the plunger 1508.

It will be appreciated that before the hard needle 1902 pierces the plunger 1508, the plunger 1508 may seal the primary drug container 1502 to contain the liquid drug 1510. Further, prior to the plunger 1508 being pierced, the plunger 1508 may seal the liquid drug 1510 off from the needle conduit 1514 (e.g., decouple or separate the liquid drug 1510 from the needle conduit 1514) such that the liquid drug 1510 cannot be supplied to the patient.

The plunger 1508 can be designed to facilitate removal of the liquid drug 1510 from the primary drug container 1502. For example, an end of the plunger 1508 that is adjacent to the portion of the primary drug container 1502 that holds the liquid drug 1510 can include one or more channels 1906. The channels 1906 can be arranged and positioned in any manner. As shown in FIG. 19, the channels 1906 can form a cross-like pattern or shape. As the plunger 1508 is moved, the liquid drug 1510 can be forced out of the primary drug container 1502 through the hard needle 1902 and on to the needle conduit 1514. The channels 1906 can help force or funnel the liquid drug 1510 towards the needle 1902 and needle inlet 1904. As a result, more of the liquid drug 1510 can be expelled from the primary drug container 1502 by reducing the amount of the liquid drug 1510 trapped or retained inside of the primary drug container 1502.

As shown in FIG. 19, the needle 1902 and opening 1904 are positioned away from a center of the plunger 1508. For example, the needle 1902 and opening 1904 are positioned towards an outer diameter of the spheres 1520 and can be positioned outside of the guide coil 1602. In various embodiments, the needle 1902 and opening 1904 can be positioned at or near an approximate center of the plunger 1508 with the channels 1906 arranged and positioned to guide the liquid drug toward the center of the plunger 1508.

Figure 20:
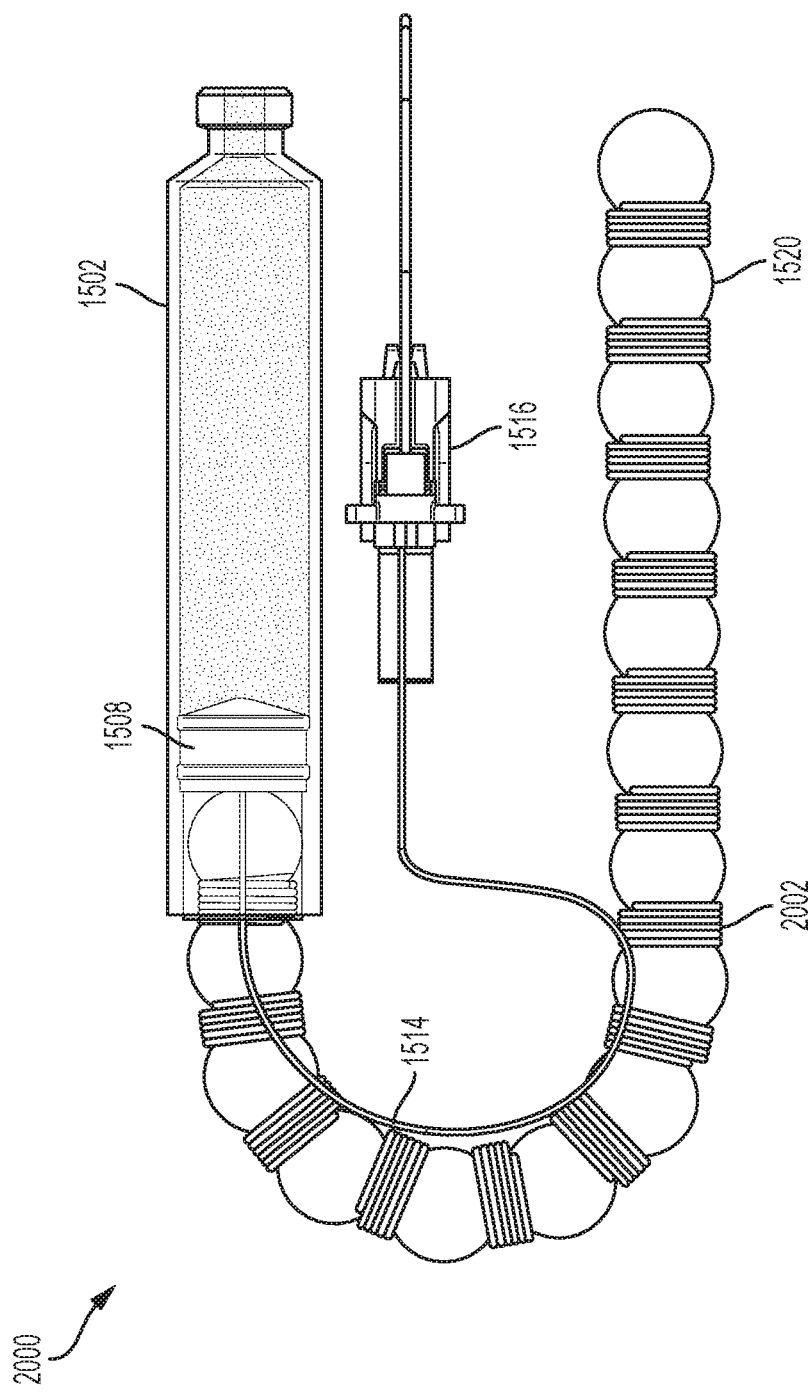
FIG. 20 illustrates a first exemplary alternative drive system for delivering a liquid drug to a patient.

FIG. 20 illustrates an exemplary alternative drive system 2000 for delivering a liquid drug to a patient. The drive system 2000 can be used with any of the drug delivery devices described herein (e.g., the drug delivery device 100). The drive system 2000 can be used to provide a single dose of liquid drug to a patient over a specified amount of time or multiple doses of the liquid drug to the patient. The drive system 2000 can correspond to the drive mechanism 210 described in relation to FIGS. 2 and 3.

As shown in FIG. 20, the drive system 2000 can include springs 2002 positioned between the spheres 1520. The springs 2002 can be considered interstitial springs or intermediate springs. The springs 2002 can be compressions springs or conical helical springs. As shown in FIG. 20, springs 2002 can be positioned between each sphere 1520. In various embodiments, the drive system 2000 can include one or more springs 2002 positioned between at least two adjacent spheres 1520. For example, the drive system 2000 can include as few as a single spring 2002 positioned between two adjacent spheres 1520. When two or more springs 2002 are used, the springs 2002 can be considered in series.

The drive system 2000 can include a release mechanism—for example, a gate or lynch pin—that can control advancement of the spheres 1520 and the springs 2002 toward the plunger 1508. In various embodiments, a gate or lynch pin can be positioned between the plunger 1508 and the first sphere 1520 positioned adjacent to the plunger 1508. The gate or lynch pin can prevent advancement of the spheres 1520 and can therefore prevent a force from being applied to the plunger 1508. When the gate or lynch pin is removed, a force from the spheres 1520 and the springs 2002 can be applied to the plunger 1508. Removal of the gate or lynch pin can initiate activation of the drug delivery device incorporating the drive system 2000. Other release mechanism can include a spring release mechanism that can restrict or allow movement (e.g., expansion) of one or more of the springs 2002. For example, the drive system 2000 can include a release mechanism that can maintain the springs 2002 in a compressed state and can allow the springs 2002 to expand when desired. The springs 2002 can be released at substantially the same time (e.g., to provide the liquid drug 1510 to the patient in a single dose). Alternatively, the springs 2002 can be released at different times (e.g., to provide the liquid drug 1510 to the patient over multiple doses).

In various embodiments, one or more the spheres 1520 of the drive system 2000 can be directly touching or in contact with one another with a spring 2002 positioned between any adjacent touching spheres 1520. The springs 2002 can be of the same size or of different sizes. The springs 2002 can each provide a same force or different forces when expanded. As The release mechanism of the drive system 2000 can allow the springs 2002 to be released/expanded at substantially the same time or at different times. For example, the springs 2002 can be released sequentially (or released in groups sequentially). In general, the springs 2002 can be allowed to expand at desired times according to a desired dosing schedule.

A track or housing or other guide (not shown in FIG. 20 for simplicity) can surround or partial enclose or contain the spheres 1520 and the springs 2002 to guide the movement of the spheres 1520 and the springs 2002. The last sphere 1520 of the drive system 2000 (e.g., the sphere 1520 positioned furthest from the plunger 1508) can be positioned against a solid element (not shown in FIG. 7) which can provide a push point for the drive system 2002. Alternatively, an assistor spring can be placed at the end of the depicted spheres 1520 and springs 2002. In various embodiments, the drive spring 1518 can be used as an assister spring. An assistor spring can be used to provide additional force to the plunger 1508. In various embodiments, an assistor spring can be similar to the previously mentioned drive spring 1518. For example, an assistor spring can be similar to the drive spring 1518 but may have a lower spring constant, k, since the springs 2002 can each provide a component of the overall provided driving force. The assistor spring can be a coil spring, an elastomeric element, or any other appropriate device (e.g., one or more compression springs arranged in any manner or configuration) for providing a desired actuation assisting force to the spheres 1520. Further, the springs 2002 can be arranged in series, which can result in a lower total or equivalent spring constant that can provide a more even force overtime as the springs 2002 expand.

The drive system 2000 can provide tunability for adjusting how quickly the liquid drug of the primary drug container 1502 can be expelled. For example, the springs 2002 can be added or removed to speed up or slow down the rate of drug delivery, respectively, for a given liquid drug. More springs 2002 may be used for liquid drugs having a relatively higher viscosity while fewer springs 2002 may be used for liquid drugs having a relatively lower viscosity. Further, more springs 2002 can be used to increase a stroke of the plunger 1508. The introduction of the springs 2002 can provide a more constant force over time and distance such that the liquid drug 1510 can be delivered at a more constant rate throughout the delivery of the drug (e.g., as compared to drive system arrangements employing only a single drive spring). Further, each spring 2002 can be tailored to provide a desired spring constant and/or desired amount of force.

The drive system 2000 can provide an approximately constant spring force (e.g., a change of less than 5% of force over a stroke). By using a large number of springs 2002, the force provided by the series coupled springs 2002 can be largely constant, thereby ensuring precise drug delivery over a long period of time. The drive system 2000 is also space efficient as the air space between the spheres is largely consumed. Again, the drive system 2000 provides an easily tunable load (e.g., to provide a variable drive force). Specifically, the load pushing on the plunger 1508 can be adjusted by adding or removing springs 2002 between the spheres 1520. This can allow for tuning of the delivery rate for drugs of different viscosities without needing to change the base design or introduce new parts. Differently sized primary drug containers 1502 (e.g., cartridges of different lengths) can also be accommodated by adding or removing springs 2002 and spheres 1520. Any of the drive systems described herein can include one or more intermediate springs 2002. For example, the drive systems depicted in FIGS. 15 and 16 can be modified to include one or more springs 2002 as shown in FIG. 20.

Figure 21:
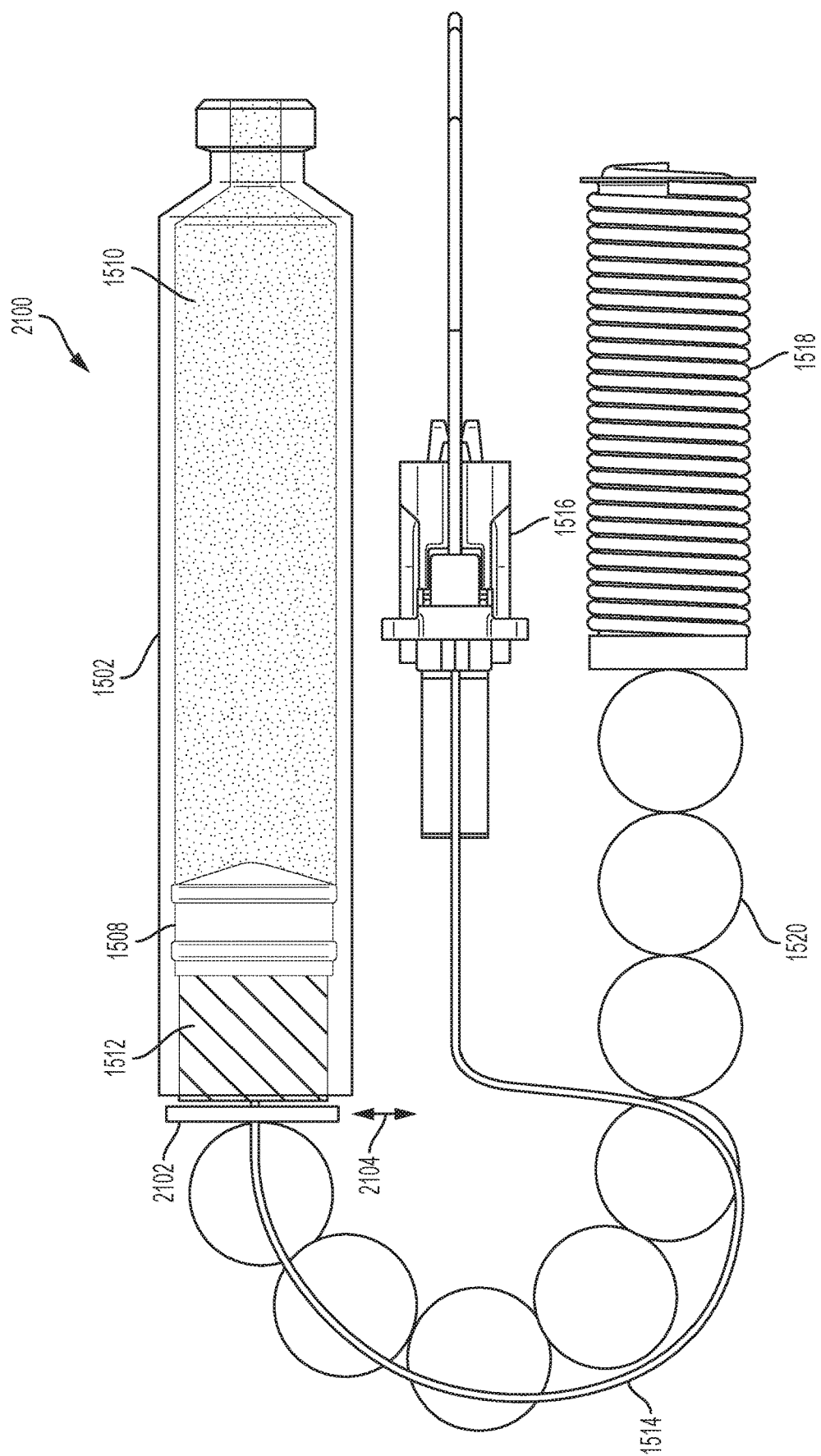
FIG. 21 illustrates a second exemplary alternative drive system for delivering a liquid drug to a patient in a first state of operation.

FIG. 21 illustrates an exemplary alternative drive system 2100 for delivering a liquid drug to a patient. The drive system 2100 can be used with any of the drug delivery devices described herein (e.g., the drug delivery device 100). The drive system 2100 can be used to advance the movement of spheres 1520 as desired to provide delivery of the liquid drug 1510 over multiple doses. The drive system 2100 can correspond to the drive mechanism 210 described in relation to FIGS. 2 and 3. The drive system can include any or all features of the drive systems described in relation to FIGS. 15, 16 and/or 20.

As shown in FIG. 21, the drive system 2100 can include a gate 2102. The gate 2102 can be positioned in front of the primary drug container 1502. The gate 2102 can be controlled to regulate the advancement of the spheres 1520 and application of a force against the plunger 1508. By regulating the advancement of the spheres 1520, the drive system 2100 can be considered as providing a metered ball or sphere drive system.

Figure 22:
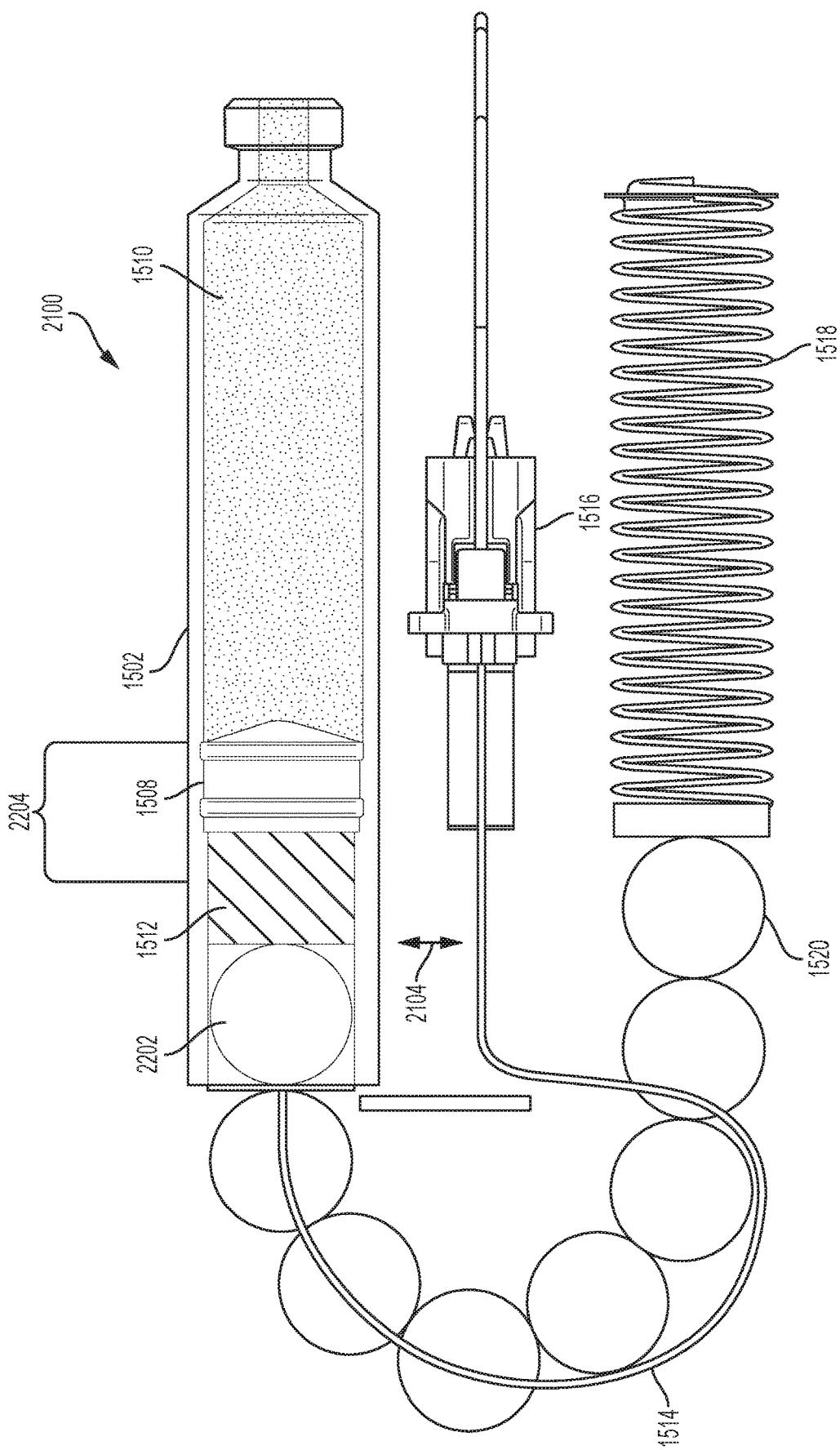
FIG. 22 illustrates the second exemplary alternative drive system of FIG. 21 in a second state of operation.

FIG. 21 shows the drive system 2100 in an initial or first state. Specifically, the gate 2102 is positioned between the first sphere 1520 and the primary drug container 1502. The spheres 1520 cannot advance further toward the plunger 1508. As result, the liquid drug 1510 is not expelled from the primary drug container 1502. As described herein, the gate 2102 can move in the directions 2104 to allow advancement of the spheres 1520 and to prevent advancement of the spheres 1520. As shown in FIG. 22, the primary drug container access mechanism 1512 can be positioned adjacent to the plunger 1508. One or more individual components of the primary drug container access mechanism 1512 are not shown in FIG. 21 for simplicity. In various embodiments, the spheres 1520 can advance the plunger 1508 by applying a force to the primary drug container access mechanism 1512, which, in turn, can apply the force to the plunger 1508. In various other embodiments, for example when the needle conduit 1514 is coupled to a septum end of the primary drug container 1502, the spheres 1520 can directly apply a force on the plunger 1508 (e.g., the primary drug container access mechanism 1512 can be removed).

FIG. 22 illustrates the drive system 2100 in a second or subsequent state of operation. Specifically, FIG. 22 shows the gate 2102 in an open state. When in an open state, the gate 2102 no longer interrupts the advancement of the spheres 1520. That is, the gate 2102 is moved to a different position that does not block the spheres 1520 from advancing toward the plunger 1508. As a result, the spheres 1520 can apply a force on the plunger 1508 to advance it forward, thereby expelling the liquid drug 1510 from the primary drug container 1502.

As shown in FIG. 22, a first sphere 2202 has advanced past the gate 2102 toward the plunger 1508. Consequently, the plunger 1508 has been advanced by an amount or distance 2204 relative to a starting point of the plunger 1508 as shown in FIG. 21. The amount 2204 that the plunger 1508 has advanced can correspond to approximately a diameter of the first sphere 2202. The diameter of the first sphere 2202 (as well as the diameters of all the spheres 1520) can correspond to one stroke of delivery of the liquid drug 1510. That is, for each sphere 1520 that advances past the gate 2102, an amount of the liquid drug 1510 corresponding to a size of each of the spheres 1520 (e.g., a diameter of the spheres 1520) can be pushed out from the primary drug container 1502. As further shown in FIG. 22, the drive spring 1518 can expand to apply the force to the spheres 1520, driving the spheres 1520 toward the plunger 1508.

By regulating the number of spheres 1520 that can advance past the gate 2102, the gate 2102 can control the amount of the liquid drug 1510 provided to the patient. Each time the gate 2102 is placed into an open position as shown in FIG. 22, one or more spheres 1520 can advance past the gate 2102. The number of spheres 1520 that advance past the gate 2102 can determine the amount of the liquid drug 1520 provided to the patient. The gate 2102 can allow the same number of spheres 1520 to advance each time the gate 2102 is opened or can allow different numbers of spheres 1520 to advance. When the gate 2102 is controlled to allow the same number of spheres 1520 to advance, then the drive system 2100 can provide multiple doses of approximately the same amount or volume of the liquid drug 1510 to the patient. When the gate is controlled to allow different numbers of spheres 1520 to advance, then the drive system 2100 can provide multiple doses of different amounts or volumes of the liquid drug 1510 to the patient. The gate 2102 can be controlled by a mechanical or electromechanical mechanism and can be automatically controlled or patient controlled. Overall, the gate 2102 can be controlled to provide a single dose to the patient or multiple doses to the patient at any desired time over any desired amount of time.

Figure 23:
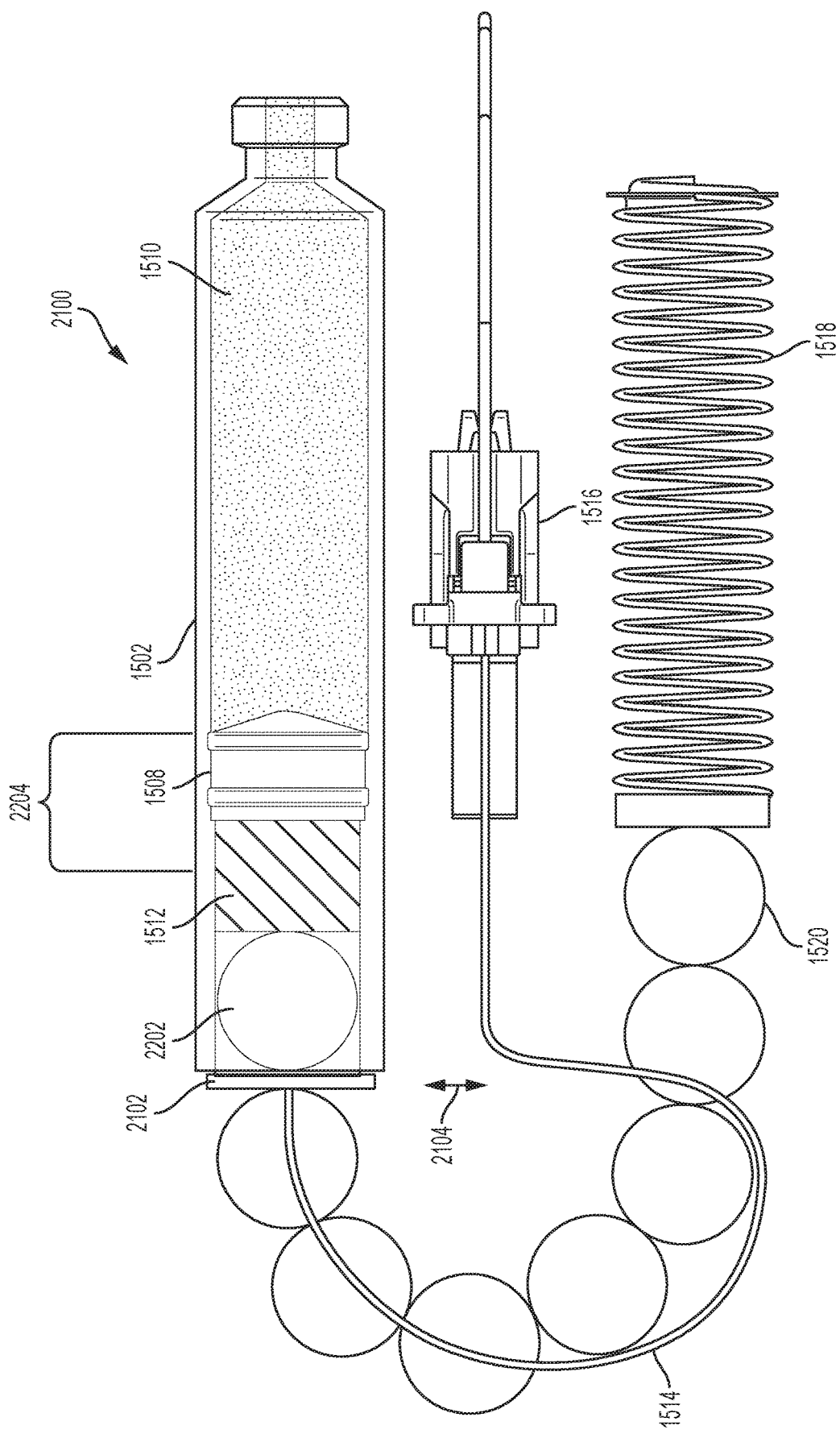
FIG. 23 illustrates the second exemplary alternative drive system of FIG. 21 in a third state of operation.

FIG. 23 illustrates the drive system 2100 in a third or subsequent state of operation. As shown in FIG. 23, the gate 2102 is in a closed position and the first sphere 2202 is positioned between the gate 2102 and the plunger 1508. With the gate 2102 in the closed position, the gate 2102 can impede further advancement of the remaining spheres 1520. As a result, a dose of the liquid drug 1510 corresponding the diameter of the first sphere 2202 has been provided to the patient.

Overall, regulating the location or position of the gate 2102 can in turn regulate delivery of the liquid drug 1510 to a patient. A desired dosage of the liquid drug 1510 can be delivered to a patient over a desired amount of time in this manner.

Figure 24:
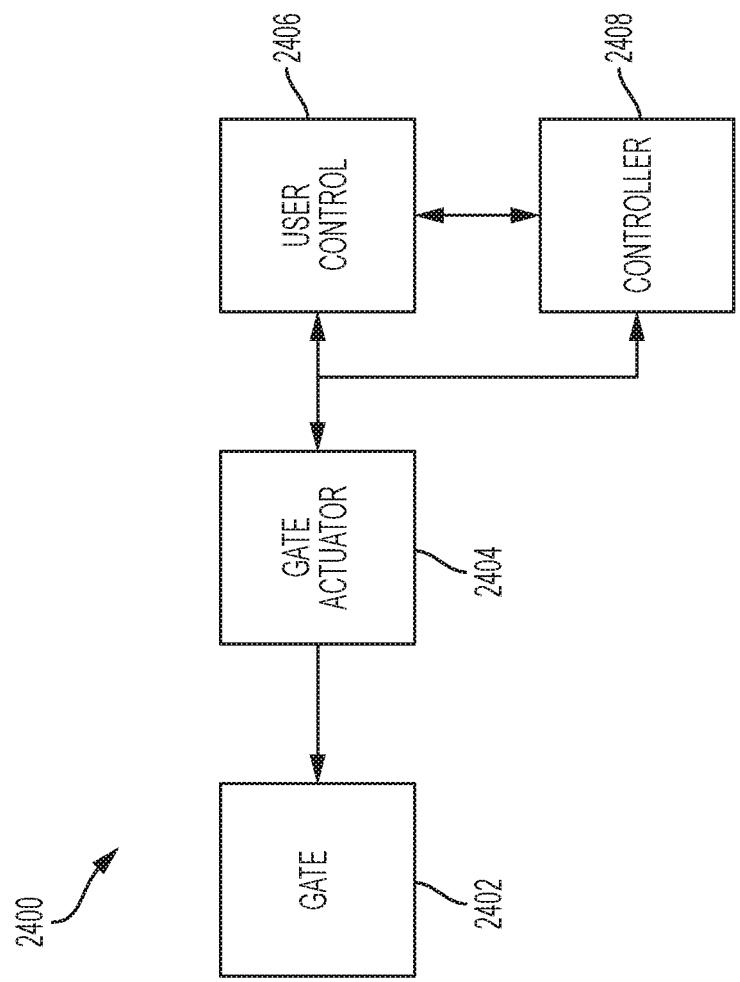
FIG. 24 illustrates an exemplary gate control mechanism of the second exemplary alternative drive system of FIGS. 21, 22, and 23.

FIG. 24 illustrate an exemplary gate control mechanism 2400. The gate control mechanism 2400 can be used to control operation and movement of the gate 2102. As shown in FIG. 24, the gate control mechanism 2400 can include a gate 2402, a gate actuator 2404, a patient control component 2406, and a controller 2408. The gate 2402 can correspond to the gate 2102. The gate actuator 2404 can be any device capable of moving the gate 2402 between at least a first position (e.g., a closed position as described in relation to FIG. 23) and a second position (e.g., an open positioning as described in relation to FIG. 23) responsive to the patient control component 2406 or the controller 2408. In various embodiments, the gate actuator 2404 can be a ratchet, a lever, a spring, or a gear. In various embodiments, the gate actuator 2404 can include a motor and an arm or other component to move the gate 2402. In various embodiments, the gate actuator 2404 can operate mechanically or electromechanically to adjust the positioning of the gate 2402.

The patient control component 2406 can be any component or feature for receiving input from a patient. In various embodiments, the patient control component 2406 can include one or more buttons or switches. The patient control component 2406 can be used to specify when the gate 2402 is to be in an open position or a closed position. The gate actuator 2404 can be responsive to the patient control component 2406 such that the gate 2402 opens and closes responsive to a patient. The patient control component 2406 can correspond to any of the patient interaction elements or components described herein (e.g., the patient interaction component 108 of the drug delivery device 100).

The controller 2408 can be used to automatically control operation of the gate 2402. In various embodiments, the controller 2408 can also control operation of the gate 2402 based on input from the patient control component 2406. The controller 2408 can correspond to the controller 302 described in relation to FIG. 3. The gate actuator 2404 can be responsive to controller 2408 such that the gate 2402 opens and closes responsive to the controller 2408. The controller 2408 can be programmed or otherwise instructed to regulate operation of the gate 2402 to provide multiple doses of a liquid drug to a patient as described in relation to FIG. 23.

Figure 25:
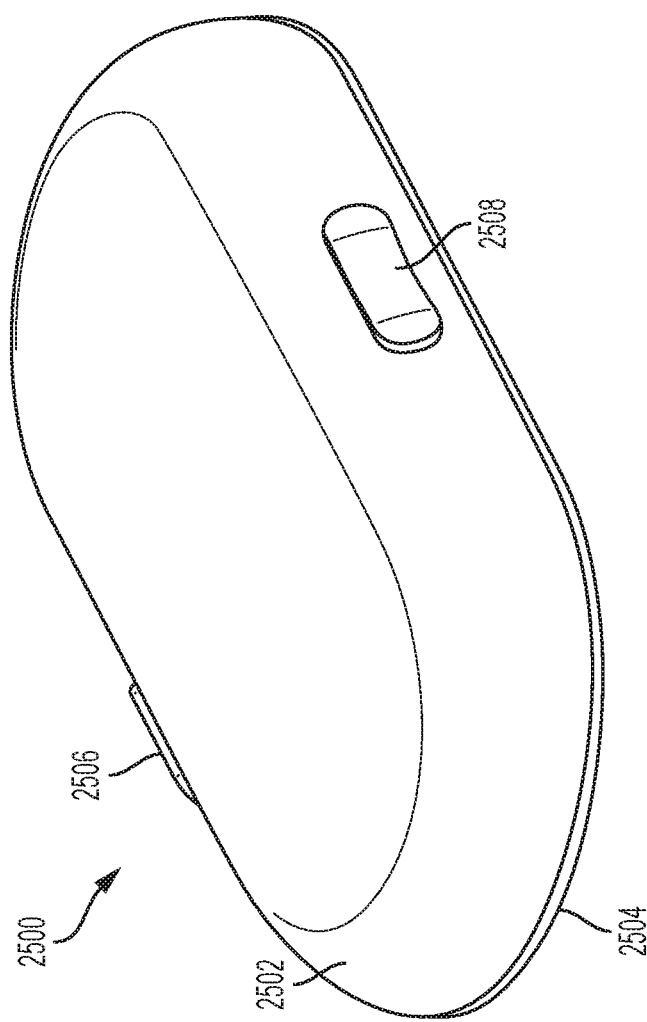
FIG. 25 illustrates a fourth exemplary embodiment of a drug delivery device.

FIG. 25 illustrates a fourth exemplary embodiment of a drug delivery device 2500. The drug delivery device 2500 can operate and provide substantially the same functionality as the drug device 100, the drug delivery device 900, and/or the drug delivery device 1400. As shown in FIG. 25, the drug delivery device 2500 can include a top portion 2502 and a bottom portion 2504. The top portion 2502 and the bottom portion 2504 can together form a housing of the drug delivery device 2500. The top portion 2502 and the bottom portion 2504 can be coupled together to form an outside of the drug delivery device 2500. The drug delivery device 2500 can represent another design or form factor of the drug delivery device 100, the drug delivery device 900, and/or the drug delivery device 1400.

As further shown in FIG. 25, the drug delivery device 2500 can include a first patient interaction element or component 2506 and a second patient interaction element or component 2508. The first and second patient interaction elements 2506 and 2508 can each be buttons located on opposite sides of the drug delivery device 2500. The buttons 2506 and 2508 can be used to activate and/or operate the drug delivery device 2500.

Figure 26:
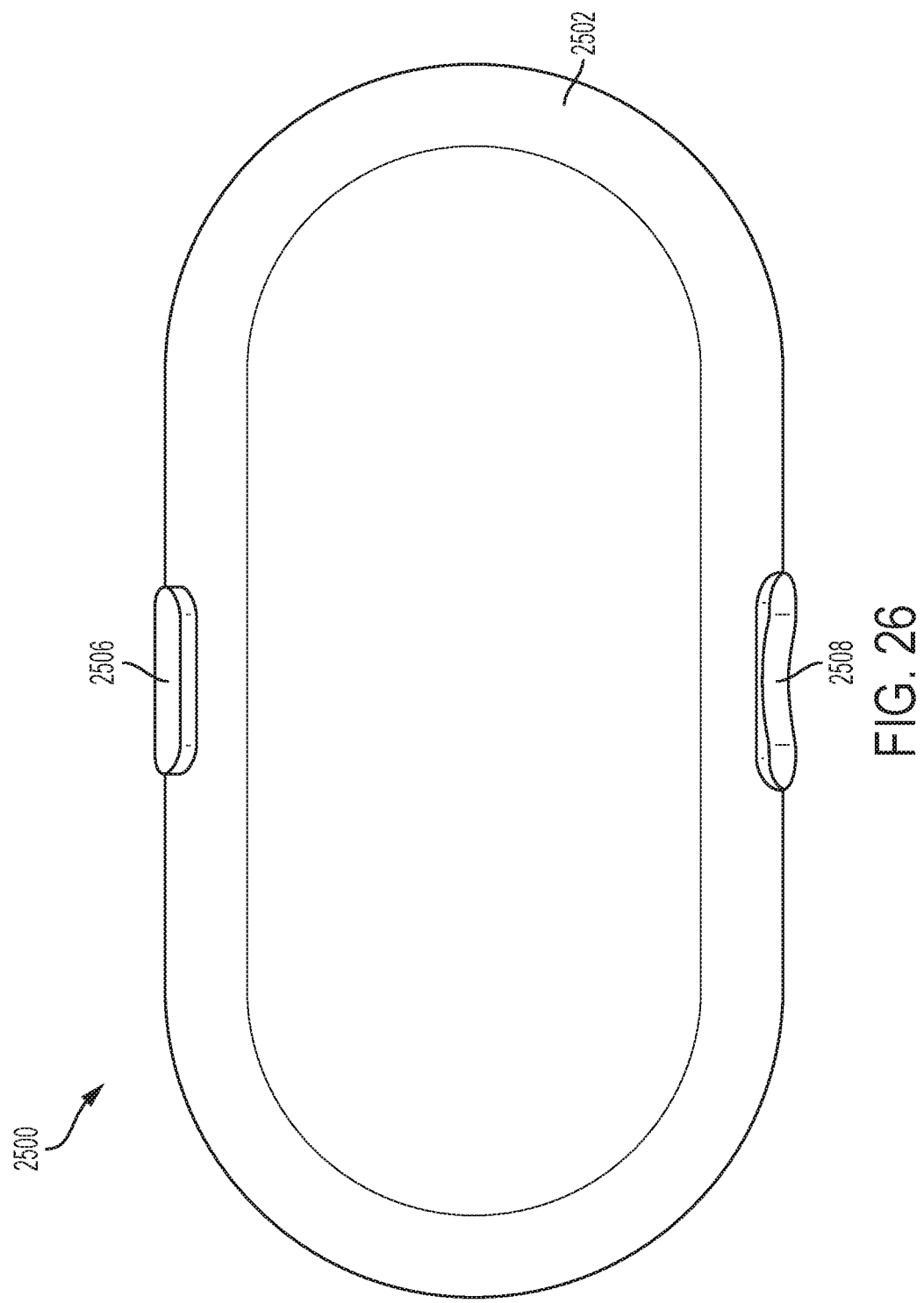
FIG. 26 illustrates a top view of the drug delivery device of FIG. 25.

FIG. 26 illustrates a top view of the drug delivery device 2500. As shown in FIG. 26, the first and second buttons 2506 and 2508 are positioned on opposite sides of the drug delivery device 2500.

Figure 27:
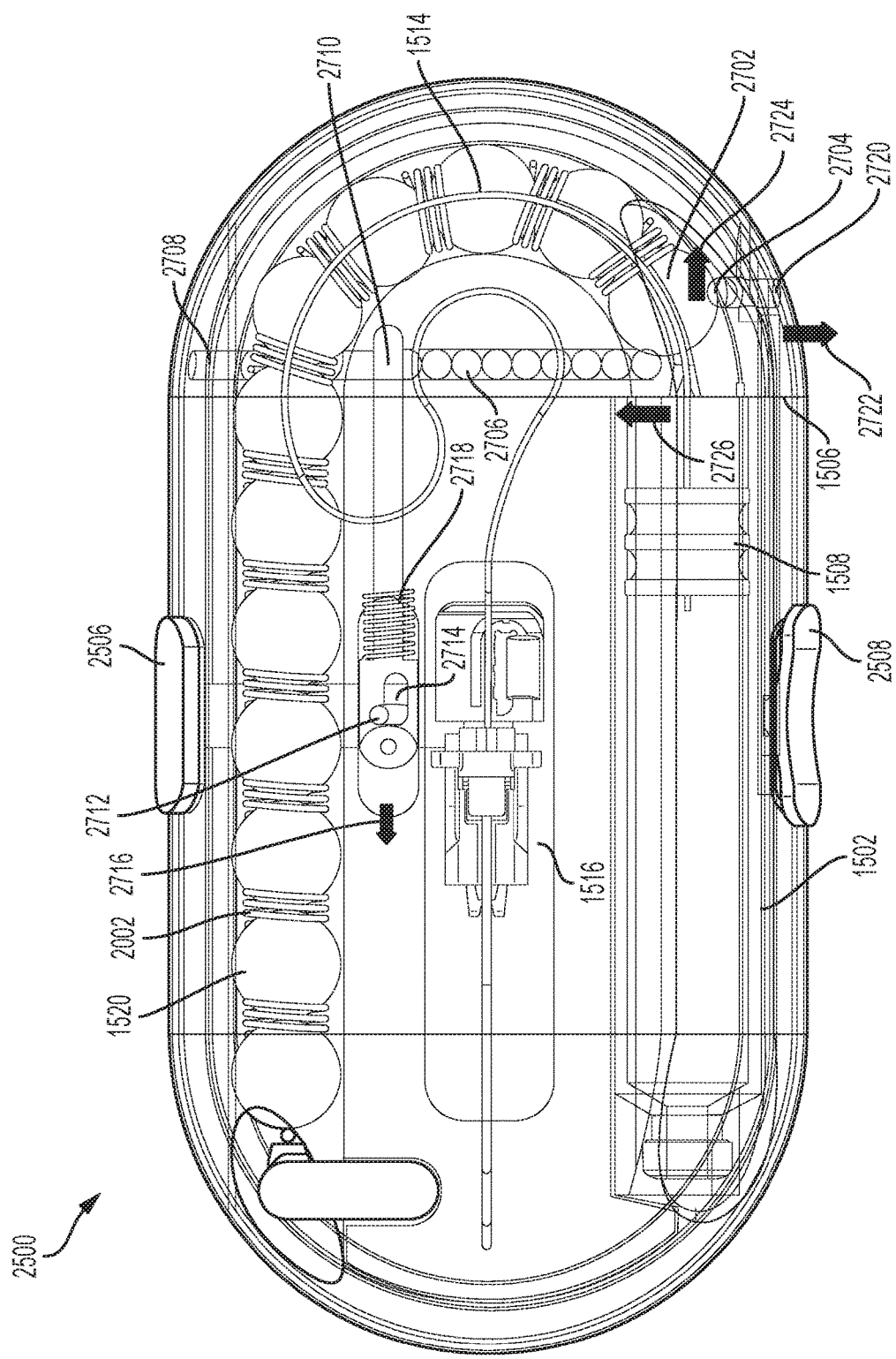
FIG. 27 illustrates an activation mechanism of the drug delivery device of FIG. 25.

FIG. 27 illustrates an activation mechanism of the drug delivery device 2500. The activation mechanism of the drug delivery device 2500 can be based on operation of the first and second buttons 2506 and 2508. The depicted activation mechanism can be included or used with any of the drug delivery devices described herein. In various embodiments, the activation mechanism of FIG. 27 may provide a "double lockout" feature that can prevent inadvertent or premature activation of the drug delivery device 2500. For example, the drug delivery device 2500 may not deliver a liquid drug to the patient until both the first and second buttons 2506 and 2508 have been activated, either in series or simultaneously, as will be described herein. As shown in FIG. 27, a first sphere 2702 is positioned adjacent to the primary drug container 1502. The first sphere 2702 is blocked from advancing toward the primary drug container 1502 by a first ball 2704 and a set of balls 2706. The first ball 2704 can be positioned on a first side of the first sphere 2702 and the set of balls 2706 can be positioned on a second, opposite side of the first sphere 2702. The set of balls 2706 can include any number of balls. The set of balls 2706 can be positioned on a track or tray 2708 that guides the movement of the balls 2706. In various embodiments, two or more balls can be used in place of the single first ball 2704. In various embodiments, as an alternative to the set of balls 2706, a rod can be used. The rod can have a length that is approximately the same as the length of the set of balls 2706 together. The rod can have rounded ends.

The first sphere 2702, and the remaining spheres 1520, can be allowed to advance toward the primary drug container 1502 when the first ball 2704 and the set of balls 2706 are moved away from the first sphere 2702. Movement of the first ball 2704 can be determined based on operation of the second button 2508. Movement of the set of balls 2706 can be determined based on operation of the first button 2506. In various embodiments, the movement of the first ball 2704 can be determined based on operation of the first button 2506 and movement of the set of balls 2706 can be determined based on operation of the second button 2508.

As mentioned, the set of balls 2706 may be coupled indirectly to the first button 2506. Movement of the set of balls 2706 can be restricted by an arm 2710. The arm 2710 can be positioned across the track 2708 to restrict or prevent movement of the set of balls 2706 along the track away from the first sphere 2702. Movement of the arm 2710 can be controlled by the first button 2506. Specifically, when the button 2506 is engaged, a pin 2712 coupled to the button 2506 can be moved in a direction (e.g., downwards and/or sideways) through an opening 2714 in the arm 2710. When the pin 2712 is moved through the opening 2714, the arm 2710 can be released, and thereby allowed to move in a direction 2716 away from the set of balls 2706, as shown in FIG. 27. A spring 2718 can assist the movement of the arm 2710 in the direction 2716 when the arm 2710 is released. Prior to pressing on the button 2506, the pin 2712 can restrict movement of the arm 2710 in the direction 2716, thereby maintaining the set of balls 2706 in the position shown in FIG. 27. The arm 2710 can be referred to as a sliding link.

Movement of the arm 2710 in the direction 2716 can allow the set of balls 2706 to move in a direction 2726 (e.g., away from the first sphere 2702). The set of balls 2706 can move in the direction 2726 along the track 2708. After moving along the track 2708, the set of balls 2706 can be positioned away from the first sphere 2702 and can no longer restrict movement of the spheres 1502. In various embodiments, upon release, the set of balls 2706 may naturally move along the track 2708 (e.g., under the force of gravity), or they may be forced to move along the track 2708 in the direction 2726 due to the force of the sphere 2702.

The second button 2508 may be indirectly coupled to the first ball 2704. Movement of the first ball 2704 can be restricted by a latch 2720. The latch 2720 can be positioned to restrict movement of the first ball 2704 in a direction 2722. Movement of the first ball 2704 can be controlled by the second button 2508. Specifically, when the button 2508 is engaged (e.g., moved laterally to slide along an outer surface of the drug delivery device 100), the latch 2720 can move in a direction that allows the first ball 2704 to move in the direction 2722 and away from the first sphere 2702. For example, the button 2508 can be slid in a direction 2724, which can cause the latch 2720 to also move in the direction 2724, thereby enabling the first ball 2704 to move away from the first sphere 2702 in the direction 2722. When the first ball 2704 moves in the direction 2722, the first ball 2704 can also no longer be positioned in front of the first sphere 2702. Consequently, the first ball 2704 can no longer restrict movement of the spheres 1520. The spheres 1520 can therefore be allowed to advance toward the primary drug container 1502 to initiate delivery of a stored liquid drug to a patient. The latch 2720 can be referred to as a push-pull rod.

The buttons 2506 and 2508 can be operated in conjunction to activate the drug delivery device 2500. In various embodiments, the buttons 2506 and 2508 can activate the drug delivery device 2500 by being manipulated at substantially the same time or in a predefined order (e.g., the button 2506 is manipulated first and the second button 2508 is manipulated subsequently). Once the buttons 2506 and 2508 are engaged, the spheres 1520 can be allowed to apply a force on the plunger 2508 to expel any liquid drug stored in the primary drug container 1502. The liquid drug can then be provided to the patient in a single dose for example.

Figure 28:
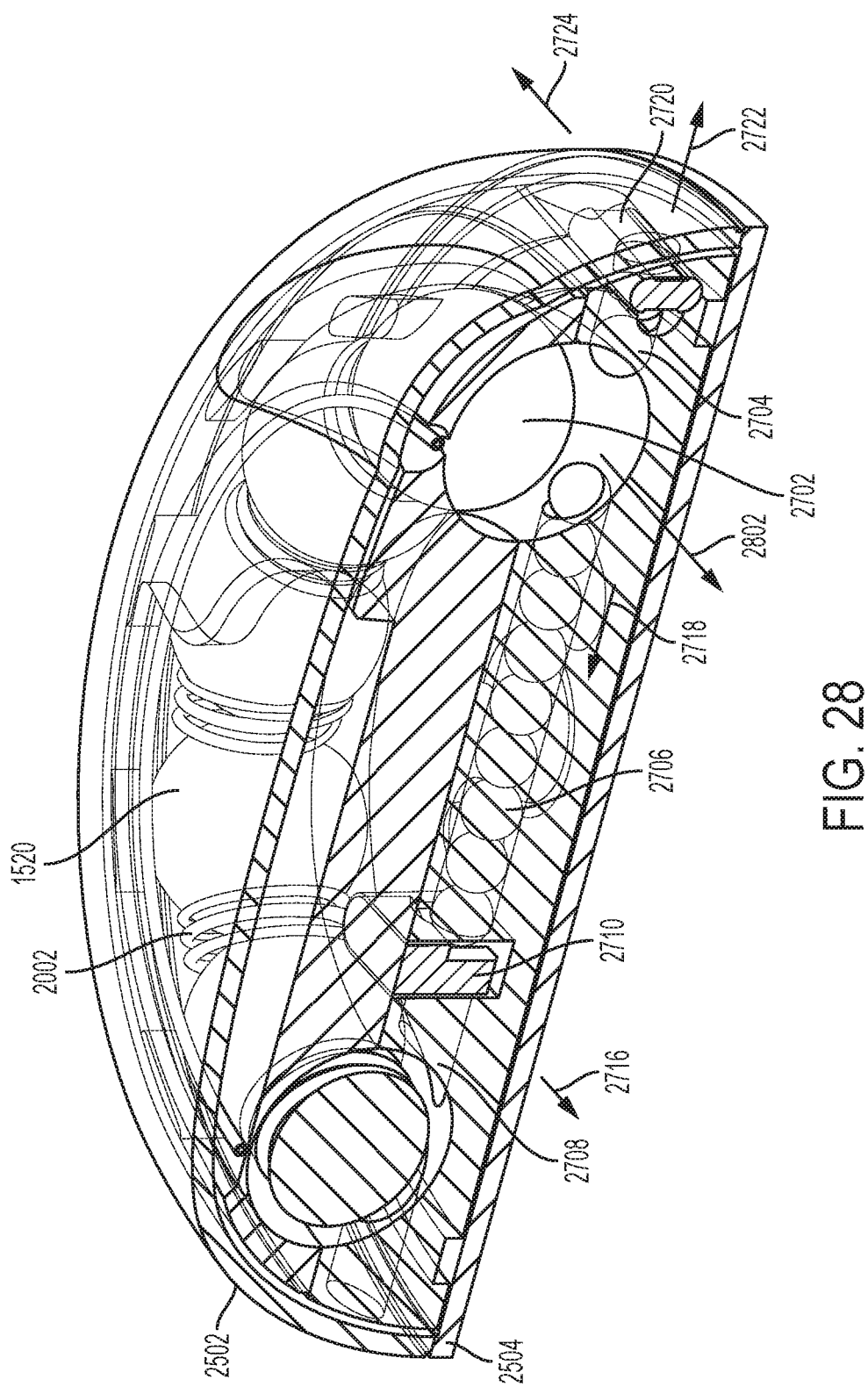
FIG. 28 illustrates a cross-sectional view of a portion of the drug delivery device shown in FIG. 27.

FIG. 28 illustrates a cross-sectional view of a portion of the drug delivery device 2500 shown in FIG. 27. FIG. 28 further shows how the drug delivery device 2500 can be activated. As shown in FIG. 28, movement of the set of balls 2706 along the guide 2708 can be restricted by the arm 2710. When the arm 2710 is moved in the direction 2716, the arm 2710 can removed from covering the guide 2708. As a result, the set of balls 2706 can be allowed to move in the direction 2726 along the guide 2708, thereby no longer blocking movement of the spheres 1520 from advancing along a direction 2802 as shown.

As further shown in FIG. 28, the latch 2720 can prevent the first ball 2704 from moving in the direction 2722. When the latch 2720 is moved in the direction 2724, the latch can be removed from restricting movement of the first ball 2704. As a result, the first ball 2704 can be allowed to move in the direction 2722, thereby no longer blocking movement of the spheres 1520 from advancing in the direction 2802.

After the first ball 2704 and the set of balls 2706 are removed from in front of the spheres 1520, the spheres 1520 can advance toward the primary drug container 1502 (not shown in FIG. 28). As mentioned, the buttons 2506 and 2508 can be operated at approximately the same time or in succession (e.g., in any order) to activate the drug delivery device.

In various embodiments, the latch 2720 can include a hole or opening through which the first ball 2704 can be forced through by the spheres 1520. The opening of the latch 2720 can be positioned adjacent to the first ball 2704 when the latch is moved by the button 2508. Prior to manipulation of the button 2508, the opening can be positioned so as not to be adjacent to the first ball 2704. When the opening of the latch 2720 is positioned next to the first ball 2704, the movement of the spheres 1520 in the direction 2802 can cause the first ball 2704 through the opening and away from the spheres 1520. Some movement of the spheres 1520 in the direction 2802 can be allowed after the set of balls 2706 are removed from being positioned in front of the spheres 1520, allowing a force of the spheres 1520 to squeeze the first ball 2704 through the opening of the latch 2720.

In various embodiments, the activation mechanism depicted in FIGS. 27 and 28 can be part of a drive mechanism or drug container access mechanism of a drug delivery device described herein (e.g., corresponding to a portion of the drive mechanism 210 and/or a portion of the primary drug container access mechanism 204 described in relation to FIGS. 2 and 3).

Figure 29:
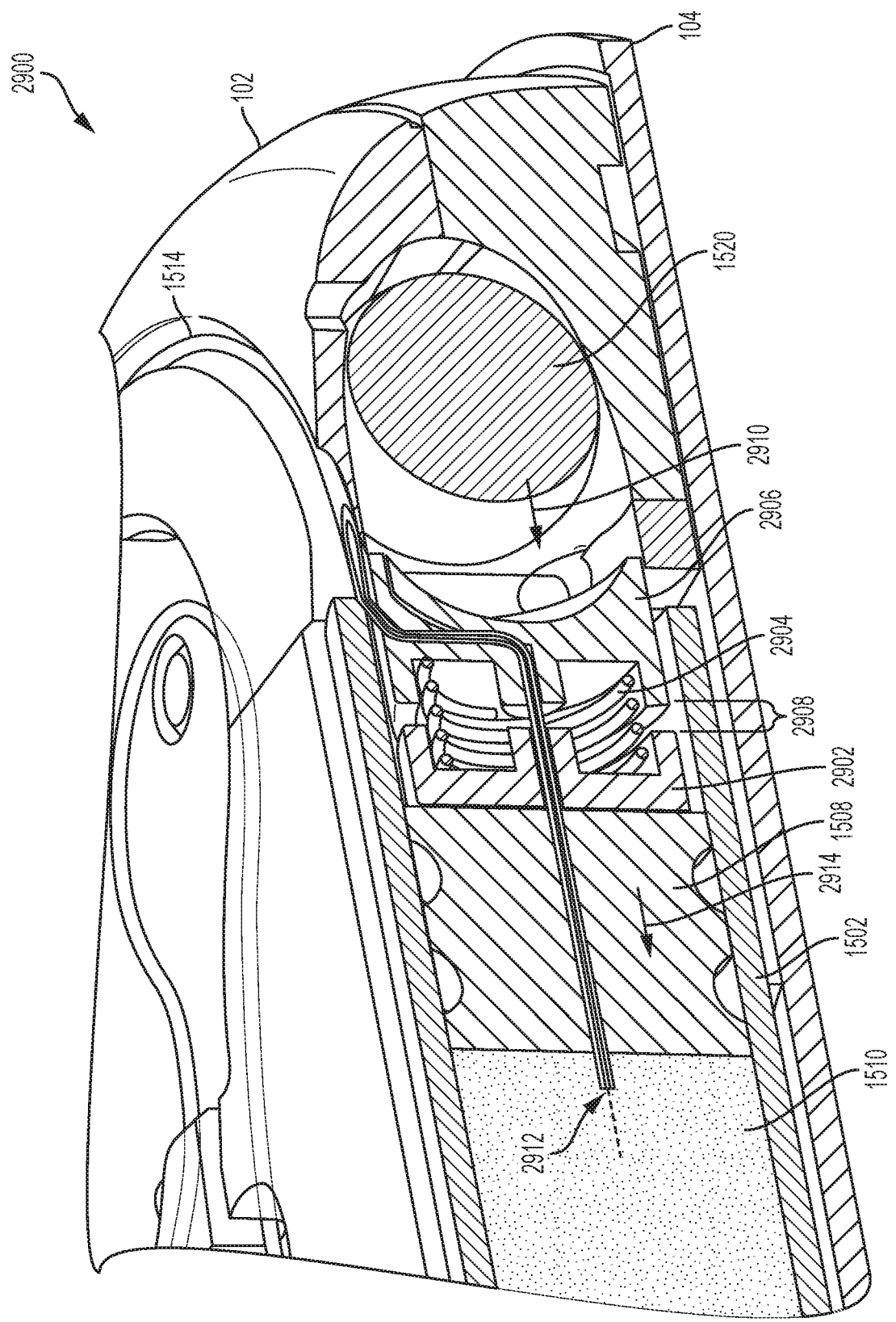
FIG. 29 illustrates an exemplary implementation of a primary drug container access mechanism.

FIG. 29 illustrates an exemplary implementation of a primary drug container access mechanism or component 2900. The primary drug container access mechanism 2900 can be an implementation of the primary drug container access mechanism 1512 depicted in FIG. 15. The primary drug container access mechanism 2900 can be used with any of the drug delivery devices described herein. FIG. 29 depicts the primary drug container access mechanism 2900 relative to a cross section of the drug delivery device 100 for purposes of describing the components and operation of the primary drug container access mechanism 2900. The primary drug container access mechanism 2900 can correspond to the primary drug container access mechanism 204 described in relation to FIGS. 2 and 3

As shown in FIG. 29, the primary drug container access mechanism 2900 can include a needle pilot element or component 2902, a spacer spring 2904, and a pusher plate element or component 2906. The needle pilot component 2902 and the pusher plate component 2906 can be made of metal or plastic. The spacer spring 2904 can be a metal compression spring 2904. The needle pilot component 2902, the spacer spring 2904, and the pusher plate component 2906 can operate to provide access to the primary drug container 1502 through the plunger 1508.

As shown in FIG. 29, the needle pilot component 2902, the spacer spring 2904, and the pusher plate component 2906 can be positioned between the plunger 1508 and a first sphere 1520. Specifically, the needle pilot component 2902 can be positioned adjacent to the plunger 1508 and the pusher plate component 2906 can be positioned adjacent to the sphere 1520. A side of the pusher plate component 2906 facing the sphere 1520 can have a curvature approximately matching a curvature of the sphere 1520, although such curvature is not critical and this surface of the pusher plate component 2906 could be flat or have another aligning feature. In one non-limiting exemplary embodiment, the plunger 1508, the needle pilot component 2902, the spacer spring 2904, and the pusher plate component 2906 can be positioned within the primary drug container 1502.

In an initial or pre-activation state, the needle pilot component 2902 can be spaced apart from the pusher plate component 2906 by a distance 2908. The pusher plate component 2906 can also be spaced apart from the first sphere 1520. The spacer spring 2904 can be positioned within an internal opening formed between the needle pilot component 2902 and the pusher plate component 2906. The needle conduit 1514 can be routed over a top of the sphere 1520 and into the pusher plate component 2906. The pusher plate component 2906 can include an opening for the needle conduit 1514. Specifically, the needle conduit 1514 can be routed approximately vertically through the pusher plate component 2906 and then routed approximately horizontally through the pusher plate component 2906 in an approximate center of the pusher plate component 2906. Other routings of the needle conduit 1514 through the pusher plate component 2906 are possible. That is, the needle conduit 1514 can be routed in any manner through the pusher plate component 2906. The needle conduit 1514 can then further extend across the distance 2908 separating the needle pilot component 2902 and the pusher plate component 2906.

Further, the needle conduit 1514 can be routed through a center of the spacer spring 2904 and through an approximate center of the needle pilot component 2902 as shown.

While in the initial state, the needle conduit 1514 can be positioned through a portion of the plunger 1508 but does not make contact with the liquid drug 1510. When positioned through a portion of the plunger 1508, the needle conduit 1514 can be considered to be partially embedded within the plunger 1508. In various other embodiments, the needle conduit 1514 can be initially positioned outside of the plunger 1508 (e.g., adjacent to the plunger 1508). When positioned outside or adjacent the plunger 1508, the needle conduit 1514 can be considered to be fully separated from the plunger 1508. The primary drug container access mechanism 2900 can be used to advance an end of the needle conduit 1514 fully through the plunger 1508 when activated with the needle conduit 1514 either initially partially embedded within the plunger 1508 or fully separated from the plunger 1508 as described herein.

During this initial, pre-activation state, the sphere 1520 can be restricted from moving forward in a direction 2910 (and/or no force can be applied to the sphere 1520). Subsequent to the initial state, when the drug delivery device of which the primary drug container access mechanism 2900 can be a part is activated, the sphere 1520 can be allowed to move in the direction 2910 toward the pusher plate component 2906. When the sphere 1520 makes contact with the pusher plate component 2906, the force from the sphere 1520 can cause the pusher plate component 2906 to move forward toward the plunger 1508.

The pusher plate component 2906 can cause the spacer spring 2904 to compress and the pusher plate component 2906 can make contact with the needle pilot component 2902, moving the needle pilot component 2902 toward the plunger 1508. As a result of the movement of the sphere 1520, the pusher plate component 2906, and the needle pilot 2902 toward the plunger, a needle 2912 or end component of the needle conduit 1514 can be pushed through the plunger 1508 into the liquid drug 1510. Overall, the end of the needle conduit 1514 (which can include the needle 2912), can be driven forward through the plunger 1508, thereby coupling the needle conduit 1514 to the liquid drug 1510.

The needle pilot component 2902 can help maintain the needle conduit 1514 centered along the plunger 1508 to facilitate efficient removal of the liquid drug 1510. The spacer spring 2904 can keep the needle pilot component 2902 and the pusher plate component 2906 separated and taught prior to activation/insertion of the tip 2912 of the needle conduit 1514 into the liquid drug 1510. The pusher plate component 2906, the spacer spring 2904, and the needle pilot component 2904 can all move in a direction 2914 to push the plunger 1508 in the direction 2914 to expel the liquid drug 1510 through the needle conduit 1514 as the spheres 1520 push on the pusher plate component 2906.

Figure 30:
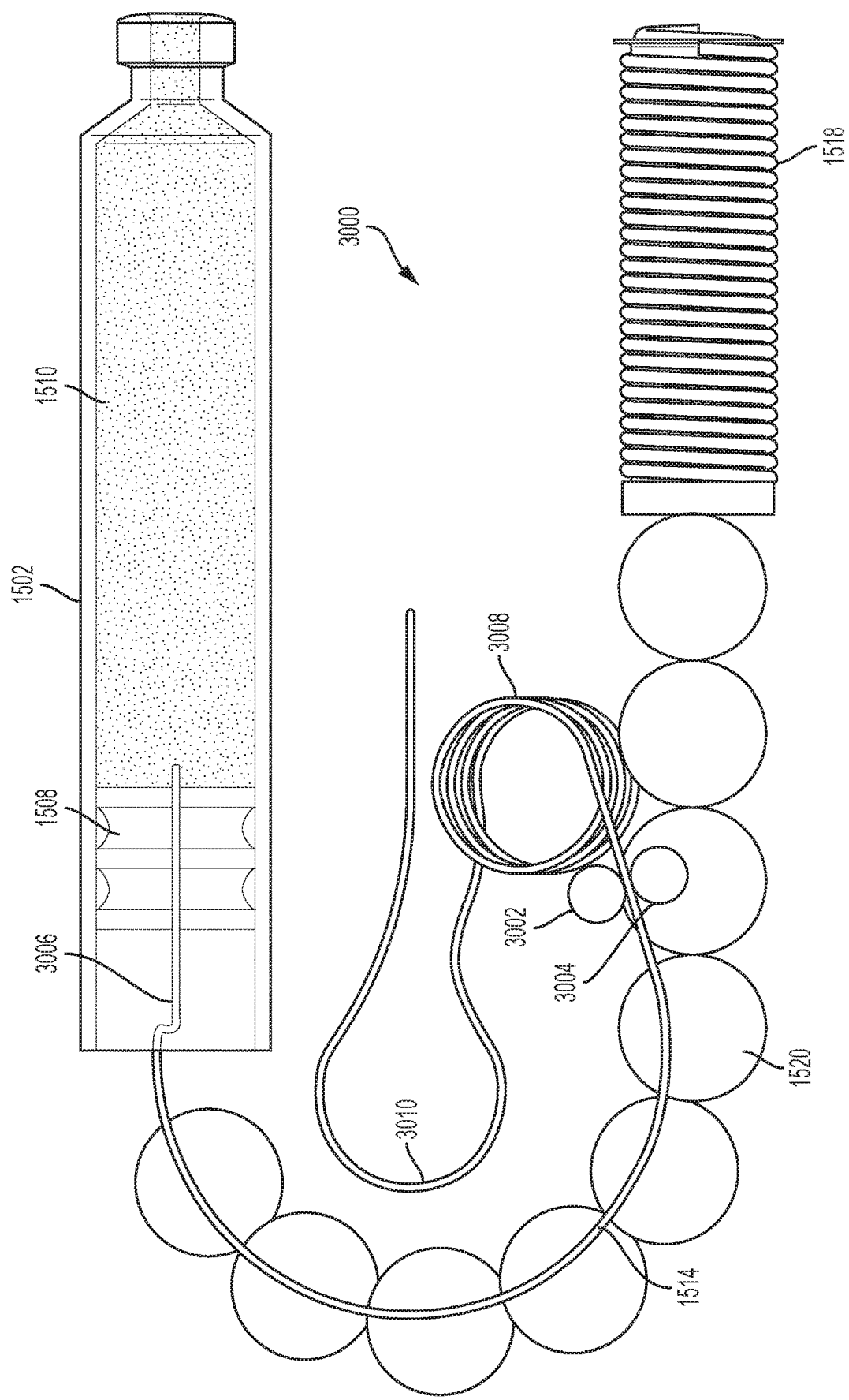
FIG. 30 illustrates a third exemplary alternative drive system for delivering a liquid drug to a patient.

FIG. 30 illustrates an exemplary alternative drive system 3000 for delivering a liquid drug to a patient. The drive system 3000 can be used with any of the drug delivery devices described herein (e.g., the drug delivery device 100). The drive system 3000 can be used to advance the movement of spheres 1520 as desired to provide delivery of the liquid drug 1510 over multiple doses. The drive system 3000 can correspond to the drive mechanism 210 described in relation to FIGS. 2 and 3. The drive system 3000 can include any feature of any of the other drive systems described herein.

As shown in FIG. 30, the drive system 3000 can include a first wheel or roller 3002 and a second wheel or roller 3004. The rollers 3002 and 3004 can be positioned above the path of the spheres 1520. The rollers 3002 and 3004 can regulate forward movement of the needle conduit 1514 toward the plunger 1508. A portion of the needle conduit 1514 can be routed between the rollers 3002 and 3004. An end portion of the needle conduit 1514 can include a hard needle 3006. The hard needle area 3006 can be advanced forward by the force of the spheres 1520. The rollers 3002 and 3004 can function as a brake or as a metering system for regulating the amount of the needle conduit 1514 that can be moved toward the plunger 1508. Specifically, the rollers 3002 and 3004 can determine when the plunger 1508 can be advanced by allowing or preventing the needle conduit 1514—and in turn the hard needle area 3006—from moving forward (e.g., as a result of the force applied by the drive spring 1518).

A portion of the needle conduit 1514 can form a coil 3008. The coil 3008 of the needle conduit 1514 can be held in place so that it can be paid out for translation to the rollers 3002 and 3004. A back portion 3010 of the needle conduit 1514 can form a loop or be otherwise shaped to provide a service loop for the needle insertion mechanism 1516.

In the drive system 3000, the needle conduit 1514 can be used as a tension member that is allowed to advance past the rollers 3002 and 3004 toward the plunger 1508 to enable the spring force form the drive spring 1518 to be applied to the plunger 1508 through the spheres 1520. Accordingly, the needle conduit 1514 can hold the drive spring 1518 back to control application of the force from the drive spring 1518 to the plunger 1508 as the spheres 1520 can be arranged to apply a force to the hard needle area 3006 of the needle conduit 1514.

The rollers 3002 and 3004 can be considered to be a clutch that regulates movement of the plunger 1508 and can therefore meter out advancement of the needle conduit 1514 and the spheres 1520, thereby allowing the drive system 3000 to be controlled for delivery of the liquid drug 1510 over multiple doses. The rollers 3002 and 3004 can be mechanically and/or electromechanically controlled. By incrementally allowing the rollers 3002 and 3004 to move or turn, incremental doses of the liquid drug 1510 to the patient. The drive system 3000 can provide for any incremental advancement of the plunger 1508. For example, the plunger 1508 can be advanced by an amount equal to less than the diameter of the spheres 1520, allowing for fine control of the amount of the liquid drug 1510 delivered to the patient. As the rollers 3002 and 3004 operate to start and stop advancement of the needle conduit 1514 and therefore the spheres 1520 and plunger 1508, the drive system 3000 can be considered to be a clutched needle drive system.

Figure 31:
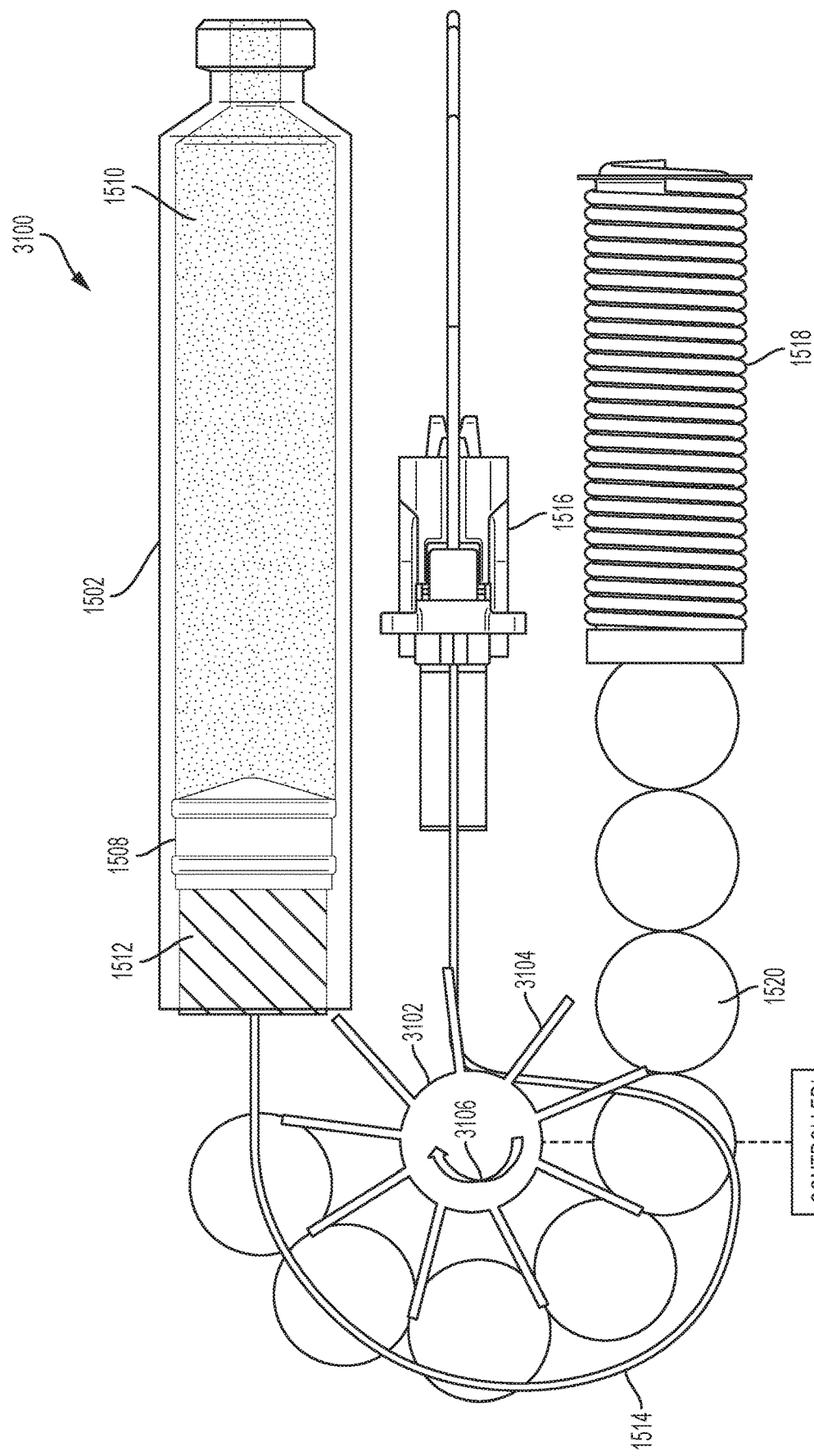
FIG. 31 illustrates a fourth exemplary alternative drive system for delivering a liquid drug to a patient.

FIG. 31 illustrates an exemplary alternative drive system 3100 for delivering a liquid drug to a patient. The drive system 3100 can be used with any of the drug delivery devices described herein (e.g., the drug delivery device 100). The drive system 3100 can be used to advance the movement of spheres 1520 as desired to provide delivery of the liquid drug 1510 over multiple doses. The drive system 3100 can correspond to the drive mechanism 210 described in relation to FIGS. 2 and 3. The drive system 3100 can include any feature of any of the other drive systems described herein.

As shown in FIG. 31, the drive system 3100 can include a dosing wheel 3102. The dosing wheel 3102 can include a number of arms or spokes 3104 that radially extend from a hub. The dosing wheel 3012 can have any number of arms 3104. One or more of the arms 3104 can be positioned between adjacent spheres 1520. The dosing wheel 3102 can rotate in a direction 3106 as shown about an axis of the dosing wheel 3102 to move the spheres 1520 forward toward the primary drug container 1502. The drive spring 1518 can provide the force to move the spheres 1520 as regulated by the dosing wheel 3102. That is, the dosing wheel 3102 can impede forward movement of the spheres 1520 until the dosing wheel 3102 rotates a desired amount in the direction 3106.

The dosing wheel 3102 can be controlled to rotate any desired amount. The dosing wheel 3102 can be triggered to rotate using a ratchet with a release that allows the dosing wheel 3102 to rotate a certain amount (e.g., a number of degrees) before re-engaging and stopping. The dosing wheel 3102 can allow less than a full sphere 1520 to advance toward the plunger 1508. That is, since the dosing wheel 3102 can rotate any desired amount, any portion of a width of one of the spheres 1520 can be allowed to advance, enabling precise multiple dose control of the liquid drug 1510. In general, an amount of rotation of the dosing wheel 3102 can determine or correspond to an amount of the liquid drug 1510 expelled from the primary drug container 1502.

As further shown in FIG. 31, the drive system 3100 can be coupled to a controller and/or patient interaction component 3108. The dosing wheel 3102 can be controlled to rotate responsive to the controller 3108. Alternatively, the patient interaction component 3108 can include a feature enabling a patient to determine when the dosing wheel 3102 rotates. For example, the patient interaction component 3108 can include a button that a patient can press to advance the dosing wheel 3102 by a fixed amount.

Figure 32:
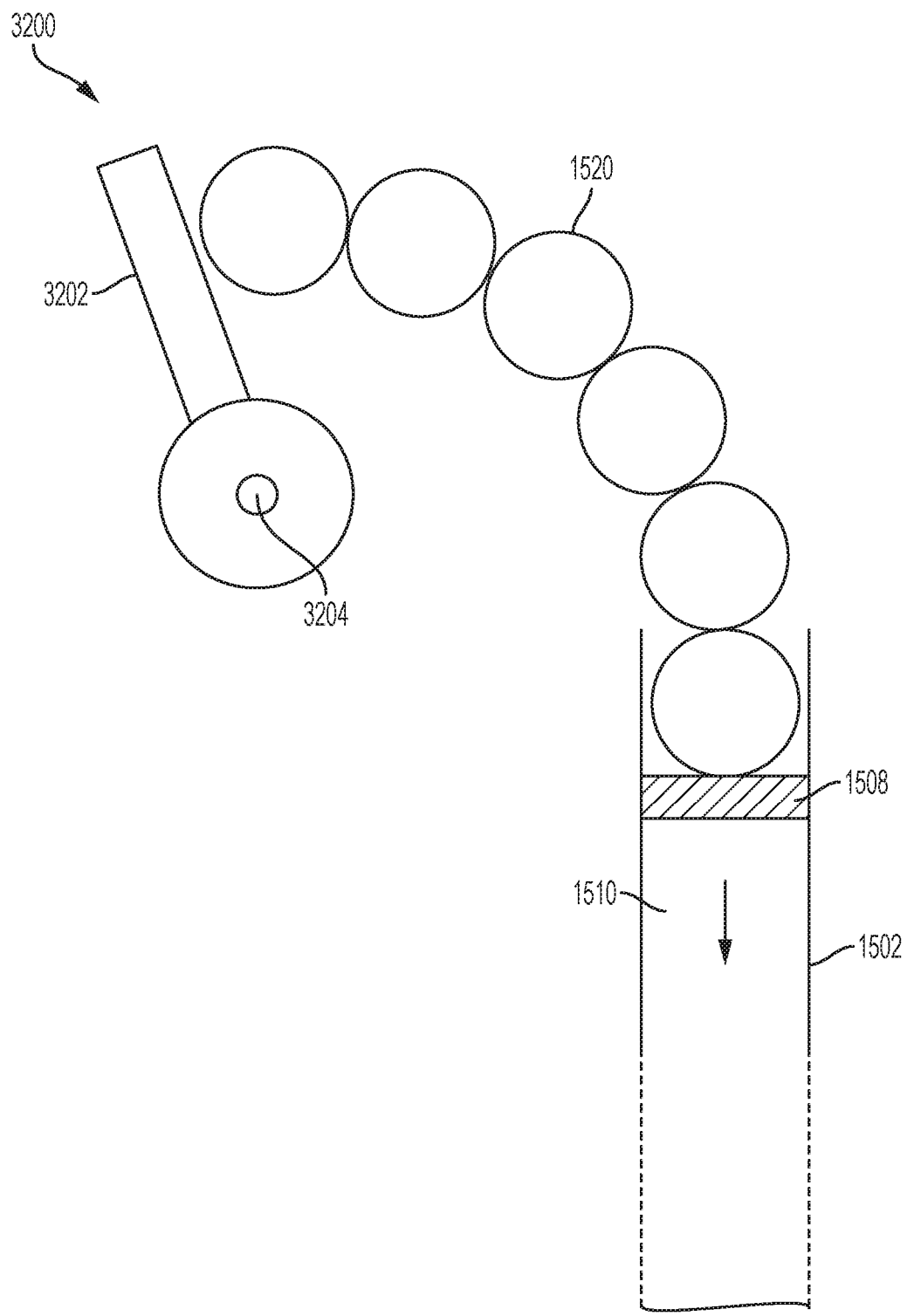
FIG. 32 illustrates a fifth exemplary alternative drive system for delivering a liquid drug to a patient.

In various embodiments, the arms 3104 can be flexing arms or flexible arms allowing the arms 3104 to fold out of the way when passing the primary drug container 1502. Further, as the arms 3104 rotate, the arms 3104 can engage a next sphere 1520 being pushed forward by the drive spring 1518. In various embodiments, the arms 3104 can include a hinge to enable the arms 3104 to fold or bend about the hinge such that the arms 3104 can be folded to prevent interference with the primary drug container 1502. The FIG. 32 illustrates an exemplary alternative drive system 3200 for delivering a liquid drug to a patient. The drive system 3200 can be used with any of the drug delivery devices described herein (e.g., the drug delivery device 100). The drive system 3200 can be used to advance the movement of spheres 1520 as desired to provide delivery of the liquid drug 1510 over multiple doses. The drive system 3200 can correspond to the drive mechanism 210 described in relation to FIGS. 2 and 3. The drive system 3200 can include any feature of any of the other drive systems described herein.

As shown in FIG. 32, the drive system 3200 can include a rotatable arm 3202. The rotatable arm 3202 can be controlled to apply a force to the spheres 1520 which can translate the force to the plunger 1508. The drive system 3200 can be implemented without a drive spring (e.g., the drive spring 1518 as described in relation to FIG. 15). The rotatable arm 3202 can rotate about a point or axis 3404.

The rotatable arm 3202 can be controlled mechanically or electromechanically. The rotatable arm 3202 can be controlled to rotate any amount relative to an axis 3404, thereby providing the ability to provide the liquid drug 1520 to the patient over multiple doses. The rotatable arm 3210 can be part of a transmission or gear reduction transmission for delivering the drug contained in the container 3202. As shown in FIG. 32, the rotatable arm 3202 can rotate in a clockwise manner to move the spheres 1520 against the plunger 1508.

Movement of the rotatable arm 3202 can be actuated by a power source such as a motor (e.g., an electrical motor). Various mechanical, electrical, and/or electromechanical mechanisms can be used to rotate or move the rotatable arm 3202. As examples, a constant force spring, a torsion spring, or a spiral torsional spring can be used to provide a force that causes the rotatable arm 3202 to move. The use of a constant force spring may be particularly advantageous as a constant force spring may not decay in the same manner as a linear spring.

The mechanism for moving the rotatable arm 3202 can allow for multiple doses of a drug to be delivered. That is, the mechanism for moving the rotatable arm 3210 can be used to deliver a dose, then stop delivery, and then restart delivery as desired (e.g., based on a desired delivery schedule in terms of dosage amount and delivery times). The mechanism for moving the rotatable arm 3210 can provide a compact movement mechanism, lending itself to inclusion in a small space within a wearable drug delivery device. Further, the mechanism can include one or more gears and/or can include one or more reduction mechanisms to adjust the efficiency of the mechanism for moving the rotatable arm 3202. Can also dose any amount, less than that corresponding to sphere.

Figure 39:
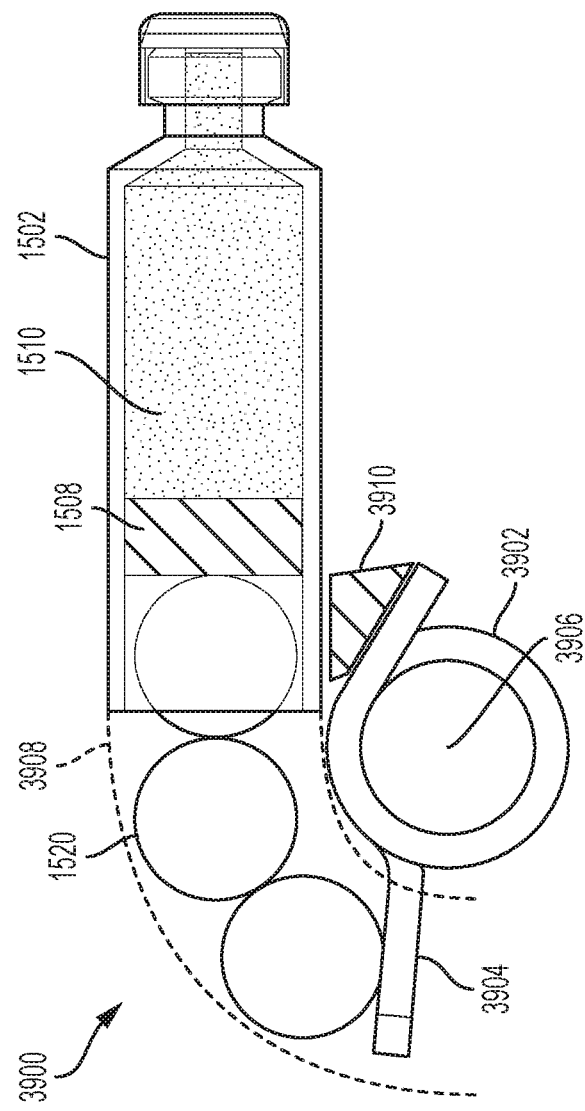
FIG. 39 illustrates a first view of an eighth exemplary alternative drive system for delivering a liquid drug to a patient.

FIG. 39 illustrates an exemplary alternative drive system 3900 for delivering a liquid drug to a patient. The drive system 3900 can be used with any of the drug delivery devices described herein (e.g., the drug delivery device 100). The drive system 3900 can be used to advance the movement of spheres 1520 as desired to provide delivery of the liquid drug 1510 over multiple doses. The drive system 3900 can correspond to the drive mechanism 210 described in relation to FIGS. 2 and 3. The drive system 3900 can represent a particular implementation of the drive system 3200 depicted in FIG. 32. The drive system 3900 can include any feature of any of the other drive systems described herein.

FIG. 39 shows a top or overhead view of the drive system 3900. The drive system 3900 can include any of the features and components of the drive systems and/or drug delivery devices described herein. Many features of the drive system 3900 such as, for example, a plunger, a sphere track, and a needle conduit are not shown in FIG. 39 for simplicity.

As shown in FIG. 39, the drive system 3900 can include a torsion spring 3902. The torsion spring 3902 can be coiled as shown to include an extending arm 3904. The arm 3904 can be positioned behind a set of spheres 1520. The torsion spring 3902 can be centered about an axis or center point 3906. The axis or center 3906 can be approximately positioned in a center of the torsion spring 3902. In various embodiments, the torsion spring 3902 can be a double-bodied torsion spring.

In an initial state, the torsion spring 3902 can be held or maintained in a coiled or compressed state. After activation, the torsion spring 3902 can be released and allowed to uncoil or expand. During release, the arm 3904 can rotate (e.g., in a clockwise direction) to advance the spheres 1520 toward the primary drug container 1502. In various embodiments, the center 3906 of the torsion spring 3902 can be offset from a center of a sphere track radius, which can improve angles of incidence for more efficient energy transfer from the torsion spring 3902 to the spheres 1520. The torsion spring 3902 can rotate about the center point 3906. In various embodiments, the tines or tongue of the torsion spring 3902 (e.g., as a double-bodied torsion spring) can be used to advance the spheres 1520.

As shown in FIG. 39, the torsion spring 3902 can be positioned adjacent to a track 3908. The track 3908 can correspond to or be an implementation of the track 1524 and/or the track 3802. The track 3908 can guide the spheres 1520 toward the plunger 1508. The track can include an open section or cutout to allow the arm 3904 to move inside of the track 3908 to advance the spheres 1520.

The arm 3904 can be retained by to activation by a number of mechanism such as, for example, a pin, rod, or other mechanical component. Once activated, the arm 3904 can be allowed to rotate (e.g., in a clockwise direction relative to FIG. 39). An inhibitor component 3910 can be used to prevent rotation and/or movement of the other portion of the torsion spring 3910. The inhibitor component 3910 can be a mechanical device such as, for example, a pin or rod restricting movement of the torsion spring 3902.

Figure 40:
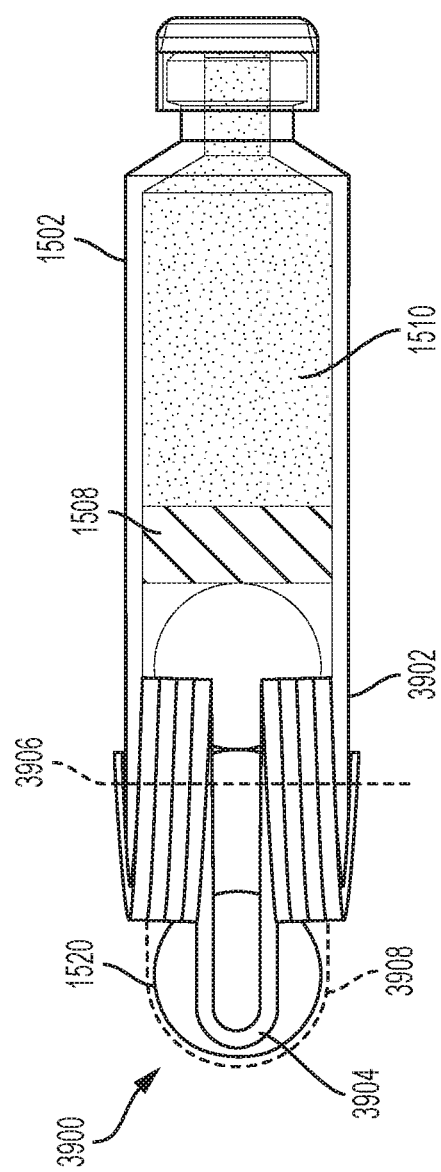
FIG. 40 illustrates a second view of an eighth exemplary alternative drive system for delivering a liquid drug to a patient.

FIG. 40 illustrates a side view of the drive system 3900 depicted in FIG. 39. As shown, the torsion spring 3902 can be positioned adjacent to the primary drug container 1502 to allow the arm 3904 to make contact with the spheres 1520. FIG. 40 shows the axis or center 3906 of the torsion spring 3902 about which the arm 3904 can rotate. The drive system 3900 can occupy less area than other drive systems described herein, enabling a drug delivery device that includes the drive system 3900 to be provided in a smaller form factor or size.

Figure 33:
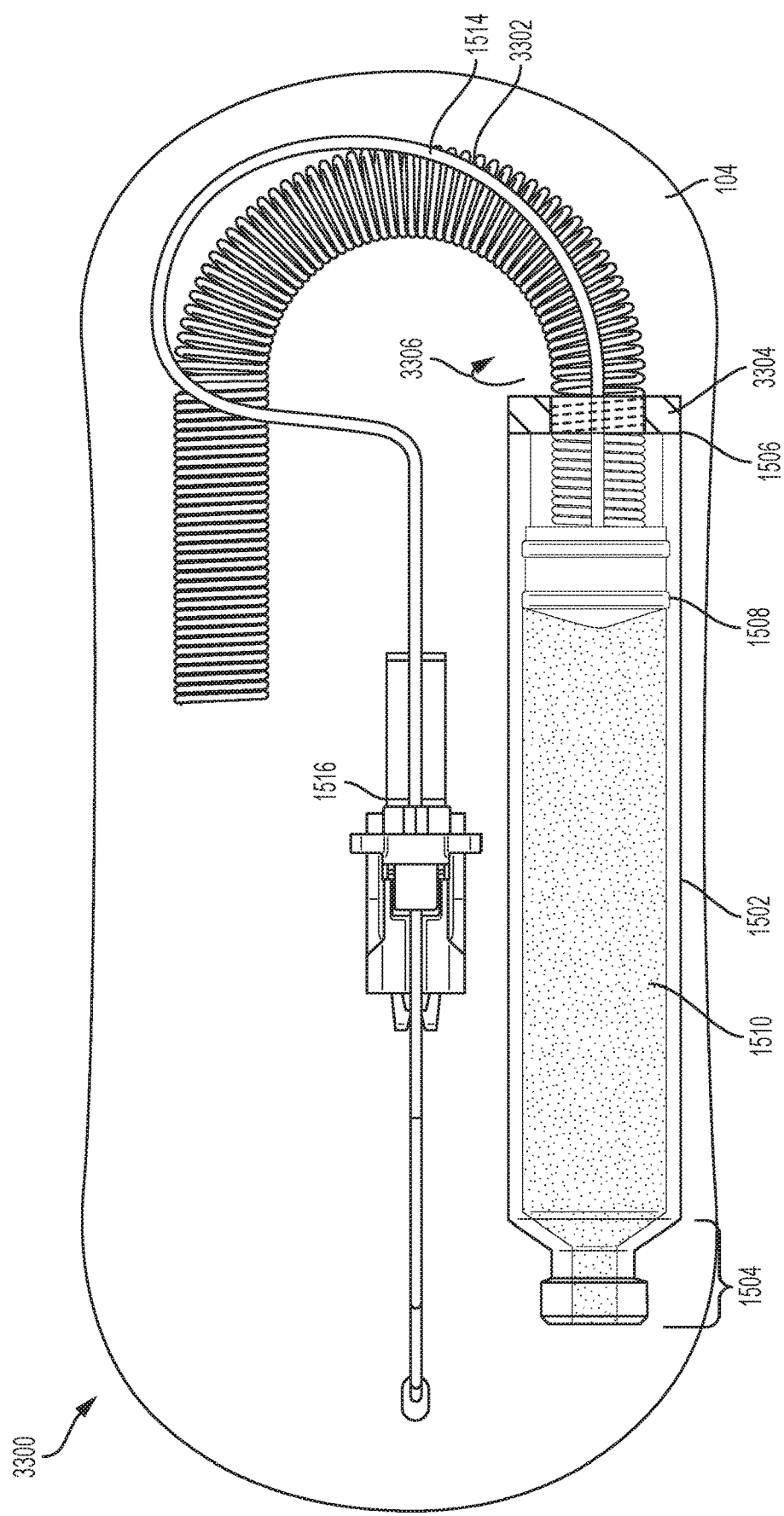
FIG. 33 illustrates a sixth exemplary alternative drive system for delivering a liquid drug to a patient.

FIG. 33 illustrates an exemplary alternative drive system 3300 for delivering a liquid drug to a patient. The drive system 3300 can be used with any of the drug delivery devices described herein (e.g., the drug delivery device 100). The drive system 3300 can be used to advance the movement of the plunger 1508 as desired to provide delivery of the liquid drug 1510 over multiple doses. The drive system 3300 can correspond to the drive mechanism 210 described in relation to FIGS. 2 and 3. The drive system 3300 can include any feature of any of the other drive systems described herein.

As shown in FIG. 33, the drive system 3300 can include a flexible drive element 3302 and a rotatable nut 3304. The flexible drive element 3302 can be a helical compression spring (e.g., a flexible lead screw). The flexible drive 3302 can be coupled to the rotatable nut 3304. The rotatable nut 3304 can be positioned at an end of the primary drug container 1502. The flexible drive element 3302 can be coupled to the rotatable nut 3304. For example, the flexible drive element 3304 can pass through a center of the rotatable nut 3304. The rotatable nut 3304 can remain in a fixed positioned, coupled to the end 1506 of the primary drug container 1502.

The rotatable nut 3304 can drive movement of the flexible drive element 3302. That is, the rotatable nut 3302 can include threads coupled to the flexible drive element 3302 to enable movement of the flexible drive element 3302 based on movement of the rotatable nut 3304. For example, rotating the rotatable nut 3304 in a first direction 3306 can move the flexible drive element 3302 in a direction toward the plunger 1508. Rotating the rotatable nut 3304 in a second, opposite direction can move the flexible drive element 3302 away from the plunger 1508. The rotatable nut 3304 can rotate perpendicularly to a vertical axis positioned in approximately a center of the primary drug container 1502. The flexible drive element 3302 can be arranged to pass through the rotatable nut 3304 to contact the plunger 1508.

The rotatable nut 3304 can be controlled mechanically or electromechanically. In various embodiments, the rotatable nut 3304 can be driven by a gear system or other mechanism such as, for example, a spring or motor. The drive system 3300 enables a force to be applied to the plunger 1508 in a tight and compact space without using a drive spring or spheres. The drive system 3300 can operate without applying any force to the flexible drive element 3302 behind the rotatable nut 3304. The flexible drive element 3302 can be routed as desired within a drug delivery device. In various embodiments, the flexible drive element 3302 can be a round wire or a rectangular wire. The rotatable nut 3304 can be controlled such that its rotation can cause the flexible drive element 3302 to advance, thereby allowing control of the rotatable nut 3304 to enable precise metering out of the liquid drug 1510. In various embodiments, one rotation of the rotatable nut 3304 can correspond to advancement of the flexible drive element by an amount corresponding to a thickness or width or the flexible drive element 3302 (e.g., a diameter of the flexible drive element 3302 when implemented as a circular or round spring).

Figure 34:
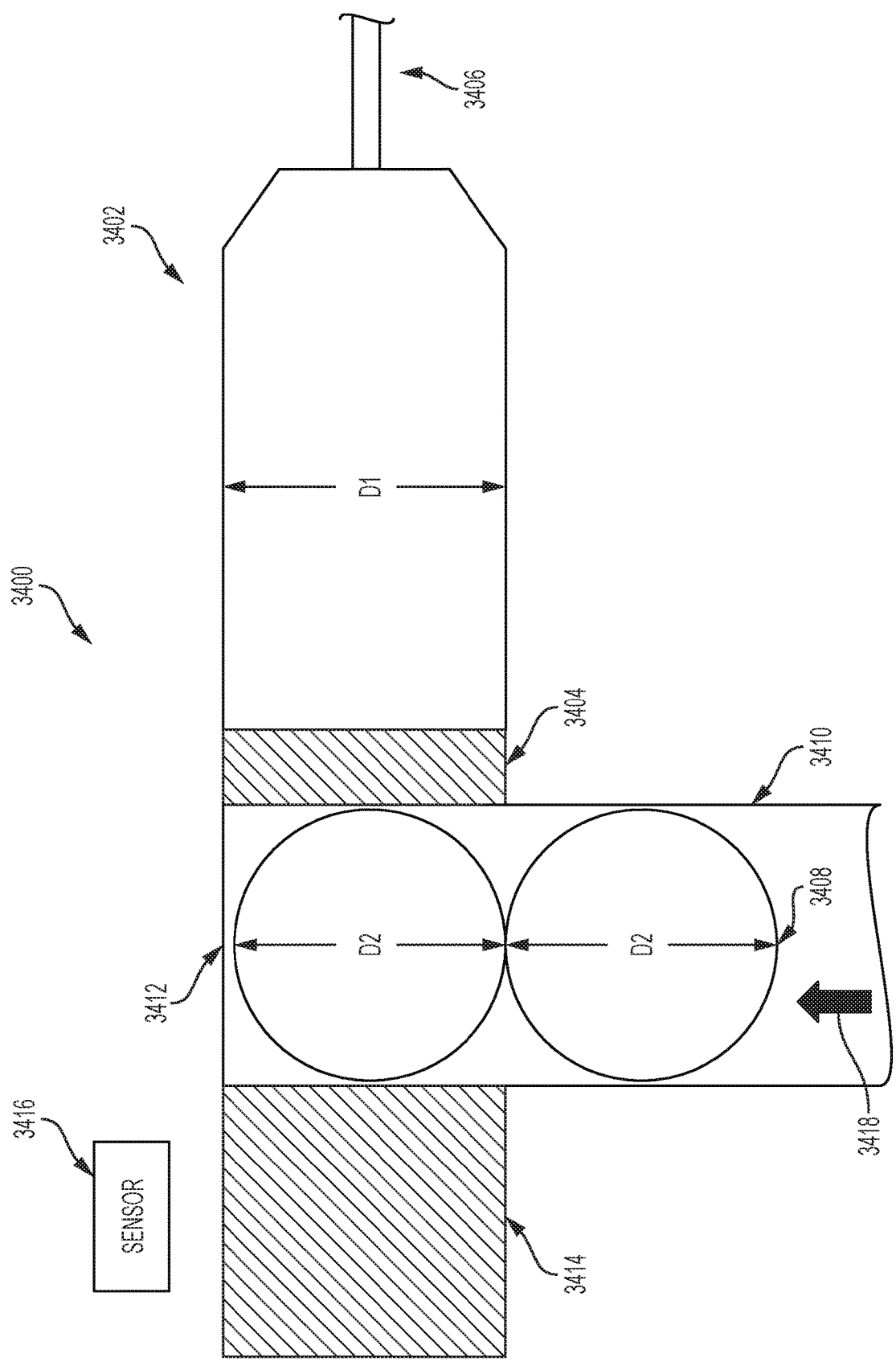
FIG. 34 illustrates a seventh exemplary alternative drive system for delivering a liquid drug to a patient in a first state of operation.

FIG. 34 illustrates an exemplary alternative drive system 3400 for delivering a liquid drug to a patient. The drive system 3400 can be used with any of the drug delivery devices described herein (e.g., the drug delivery device 100). The drive system 3400 can be used to advance the movement of a plunger as desired to provide delivery of the liquid drug over multiple doses. The drive system 3400 can correspond to the drive mechanism 210 described in relation to FIGS. 2 and 3. The drive system 3400 can include any feature of any of the other drive systems described herein.

FIG. 34 illustrates the drive system 3400 in a first position or operating state. As shown in FIG. 34, the drive system 3400 can include a drug container 3402 (e.g., corresponding to the primary drug container 1502). The container 3402 can contain a liquid drug or medicine (e.g., corresponding to the liquid drug 1510). The container 3402 can be a prefilled cartridge. A plunger 3404 (e.g., corresponding to the plunger 1508) can initially be positioned in proximity to a first end of the container 3402. A fluid exit path 3406 can be positioned in proximity to a second, opposite end of the container 3402. The fluid exit path 3406 can include tubing, a needle, and/or a cannula for transferring a fluid from one location to another. The fluid exit path 3406 can be coupled to the container 3402 and can be in fluid communication with the contents of the container 3402. The fluid exit path 3406 can correspond to the needle conduit 1514 or a portion thereof. As the plunger 3404 is moved (e.g., from the first end of the container 3402 to the second end of the container 3402), the liquid drug inside of the container 3402 can be forced out of the container 3402 and through the fluid exit path 3406 for delivery to a patient.

The plunger 3404 can be moved in a direction towards the second end of the container 3402 (towards the needle conduit 3406) by one or more spheres 3408 (e.g., corresponding to the spheres 1520). The spheres 3408 can be positioned within and can travel within a sphere path 3410. The positioning of the spheres 3408 can be maintained by a wall stop 3412 and an actuated stop 3414. Specifically, the wall stop 3412, the actuated stop 3414, and the sphere path 3410 can maintain one or more spheres adjacent to the plunger 3404.

The actuated stop 3414 can be moved by a drive system. The drive system can be an electromechanical drive system. The actuated stop 3414 can move left and right (relative to the orientation shown in FIG. 34) to open and close a space between the actuated stop 3414 and the plunger 3404. As shown in FIG. 34, the actuated stop 3404 can be considered to be in an open position such that one or more spheres 3408 can be positioned between the actuated stop 3414 and the plunger 3404. The container 3402 can generally be cylindrical in shape but is not so limited and can have a diameter of D1 as indicated in FIG. 34. The spheres 3408 can generally be spherical in shape but are not so limited and can have a diameter of D2 as shown in FIG. 34. The diameter D2 of the spheres 3408 can be slightly smaller than the diameter D1 of the container 3402.

The actuated stop 3414 can be moved by a mechanical, electrical, and/or electromechanical drive system. As an example, the actuated stop 3414 can be coupled to a linear induction motor that enables the actuated stop 3414 to move forward and backwards. When the actuated stop 3414 moves to the left, a space can open up between the actuated stop 3414 and the plunger 3404. Depending on the size of the open space, one or more spheres 3408 can move upwards from the sphere path 3410 to occupy the open space. As shown in FIG. 34, a single sphere 3408 is positioned adjacent to the wall stop 3412 and between the actuated stop 3414 and the plunger 3404.

Once at least one sphere 3408 is positioned as shown in FIG. 34, the actuated stop 3414 can be moved to the right (towards the plunger 3404). Movement of the actuated top 3414 towards the plunger 3404 can cause the sphere 3048 to push against the plunger 3404. The force of the sphere 3408 against the plunger 3404 can cause the plunger 3404 to move to the right (towards the needle conduit 3046). Movement of the plunger 3404 towards the needle conduit 3406 can cause the liquid drug stored in the container 3402 to be forced out of the container 3402 and into the fluid exit path 3406. Accordingly, the movement of the actuated stop 3414 can cause a portion of the liquid drug from the container 3402 to be delivered to a patient.

The amount of drug delivered to the patient can be determined based on the amount of movement of the actuated stop 3414 and/or the diameter D2 of the spheres 3408. For example, a single dose of a drug can correspond to the amount of drug expelled from the container 3402 when the plunger 3404 is moved by an amount corresponding to the diameter D2 of a single sphere 3408. In various embodiments, the actuated stop 3414 can be moved to allow more than one sphere 3408 to push the plunger 3404 forward during each actuation of the actuated stop 3414. In various embodiments, the actuated stop 3414 can be moved to allow the plunger 3404 to move a distance that is less than a diameter of the sphere 3408. Accordingly, any size dosage can be provided by the drive system 3400 (e.g., any dosage corresponding to any distance the plunger moves 3404 corresponding to any portion of the diameter of a sphere 3408 or more than one sphere 3408). Further, as shown in 3418, a force 3418 can be provided to position the spheres 3408 towards the wall stop 3412. The force 3418 can be provided by any mechanical and/or electromechanical mechanism such as, for example, a spring or motor.

Figure 35:
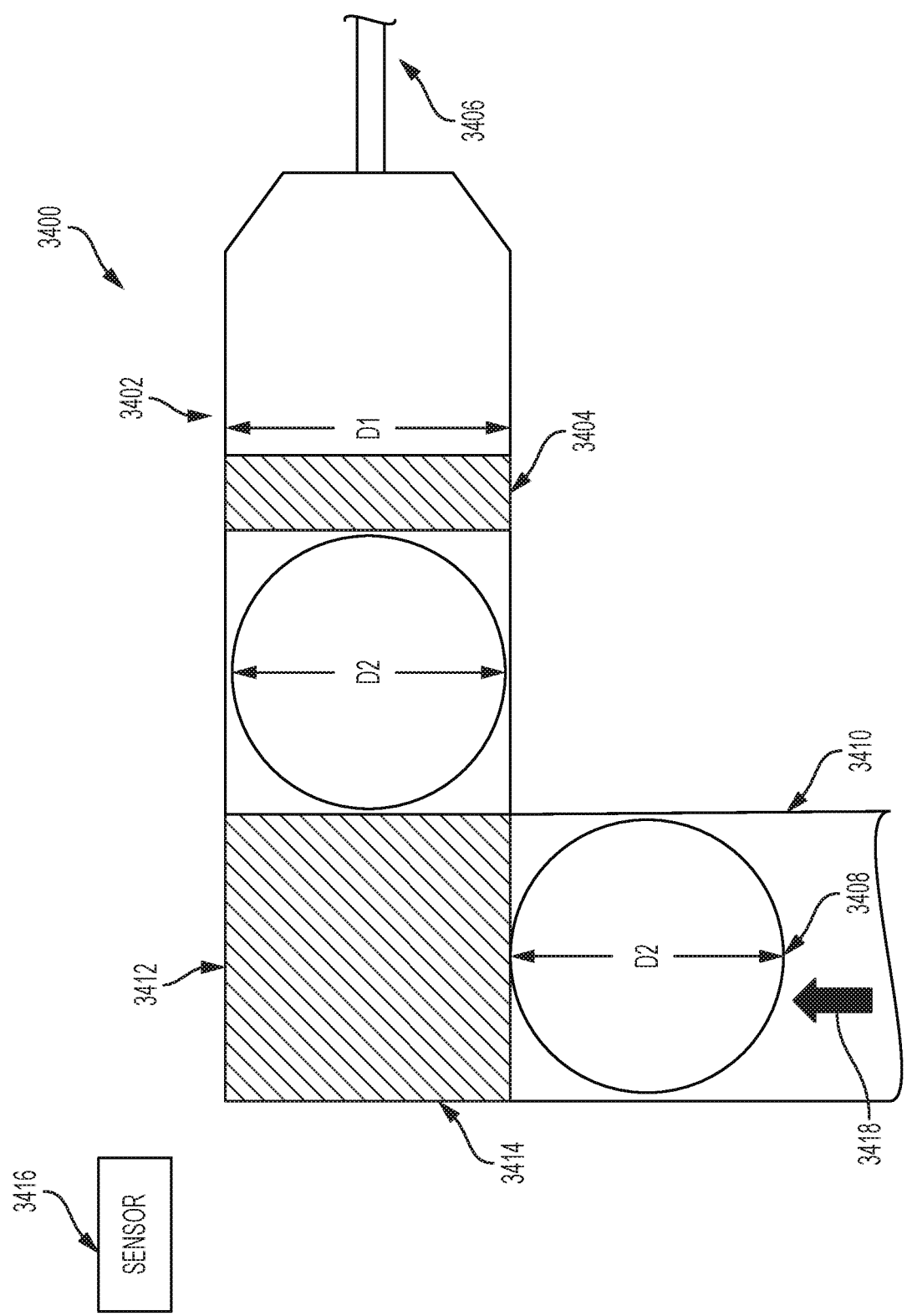
FIG. 35 illustrates the seventh exemplary alternative drive system in a second state of operation.

FIG. 35 illustrates the drive system 3400 in a second position or operating state. As shown in FIG. 35, the actuated stop 3414 has been moved to the right towards the plunger 3404. As a result, the first sphere 3408 has been moved forward towards the plunger 3404 causing the plunger to move towards the fluid exit path 3406. The movement of the plunger 3404 by being pushed by the sphere 3408 causes a portion of the liquid drug of the container 3402 to be pushed out through the fluid exit path 3406.

As shown in FIG. 35, the plunger 3404 has been moved by a distance approximately equal to the diameter D2 of the sphere 3408. This amount of plunger 3404 movement can correspond to one dosage of the liquid drug stored in the container but is not so limited. Overall, the diameter D2 of the spheres 3408 can set the dosage amount per sphere 3408 with the amount of dosage of the drug being equal to the number of sphere 3408 diameters or fractions thereof which correspond to the amount of plunger 3404 movement.

The drive system 3400 can be used to push the spheres 3408 and the plunger 3404 in a controlled manner. The speed at which these components are pushed can determine the speed of delivery of the drug and can be adjusted or varied. The operation of the drive system 3400 can toggle between the two states shown in FIGS. 34 and 35. For example, in a next operating state of the drive system 3400, the actuated stop 3414 can be moved back away from the plunger 3404 to open up a space for a next sphere 3408. As a result, two spheres 3408 can be positioned adjacent to one another in line with the actuated stop 3414 and the plunger 3404. A next amount of drug can be delivered to the patient when the actuated stop 3414 moves forward again towards to the plunger 3404 to push both spheres 3408 against the plunger 3404.

A sensor 3416 as shown in FIGS. 34 and 35 can be used to detect the position of the actuated stop 3414 and/or the positions of the spheres 3408. The sensor 3416 can provide an indication of position of these components to a drive system and/or controller for moving the actuated stop 3414. In various embodiments, the sensor 3416 can be a Hall effect sensor. The sensor 3416 can be coupled to a controller or other logic that can maintain a count of how many spheres have been moved into the position to move the plunger 3404. In doing so, a measure of the number and size of doses can be tracked. The wall stop 3412 can be fixed or can be moveable. In various embodiments, the wall stop 3412 can be moved back and forth (e.g., up and down relative to the orientation shown in FIGS. 34 and 35) to enable spheres 3408 to be moved up near the container 3402.

The drive system 3400 provides numerous benefits over conventional drug delivery systems. First, the drive system 3400 provides a mechanism for starting and stopping delivery of the drug contained in the container 3402. As a result, the drive system 3400 can start and stop delivery of the drug and can therefore provide multiple doses of a drug over a desired period of time according to a delivery schedule. Further, the compact design of the drive system 3400 enables the drive system 3400 to be placed inside of a wearable drug delivery device that can remain small and compact in size. The drive system 3400 also enables actuation of the plunger 3404 on a sphere by sphere basis.

Figure 36:
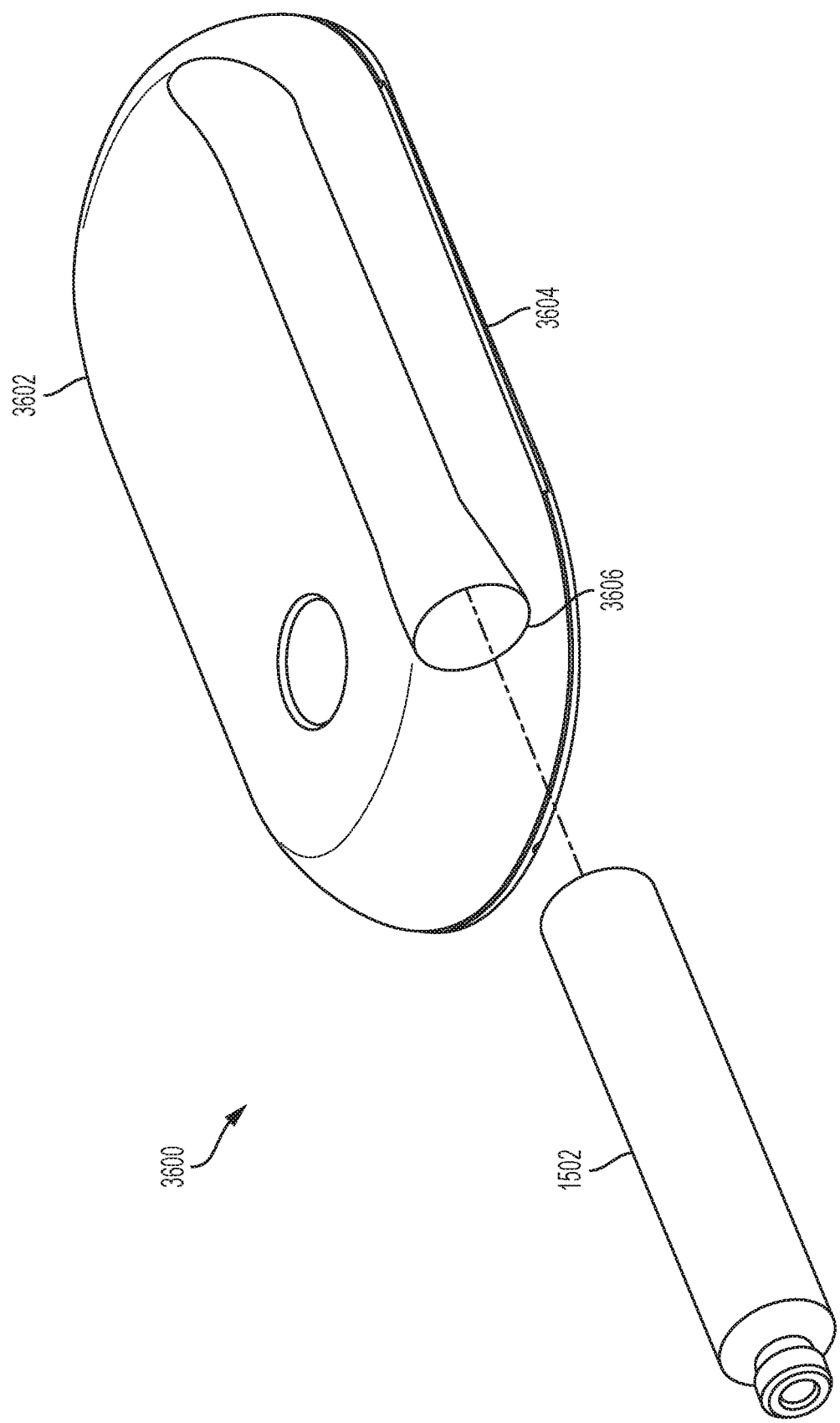
FIG. 36 illustrates a fifth exemplary embodiment of a drug delivery device.

FIG. 36 illustrates a fifth exemplary embodiment of a drug delivery device 3600. The drug delivery device 3600 can operate and provide substantially the same delivery device 3600 can include a top portion 3602 and a bottom portion 3604. The top portion 3602 and the bottom functionality as the drug device 100, the drug delivery device 900, the drug delivery device 1400, and/or the drug delivery device 2500. As shown in FIG. 36, the drug portion 3604 can together form a housing of the drug delivery device 3600. The top portion 3602 and the bottom portion 3604 can be coupled together to form an outside of the drug delivery device 3600. The drug delivery device 3600 can represent another design or form factor of the drug delivery device 100, the drug delivery device 900, the drug delivery device 1400, and/or the drug delivery device 2500.

As shown in FIG. 36, the drug delivery device 3600 includes an opening 3606. The opening 3606 can be used for inserting or removing a drug cartridge (e.g., the primary drug container 1502). The opening 3606 can be a hole or slot and can have a door (e.g., a hinged door) for maintaining the cartridge inside of the drug delivery device 3600. In this way, the drug delivery device 3600 can be loaded with prefilled cartridges and can be reused as it allows spent cartridges to removed and discarded.

Figure 37:
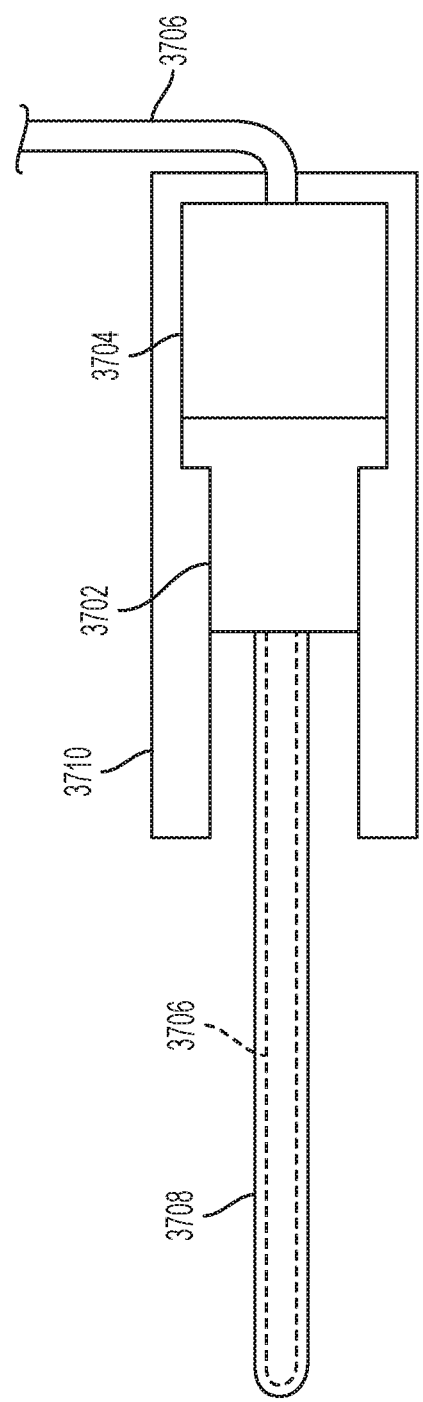
FIG. 37 illustrates an exemplary embodiment of a needle insertion mechanism.

FIG. 37 illustrates an exemplary embodiment of a needle insertion mechanism or component 3700. The needle insertion mechanism 3700 can correspond to the needle insertion mechanism 208 described in relation to FIGS. 2 and 3. The needle insertion mechanism 1516 can represent an implementation of the needle insertion mechanism 3700. The needle insertion mechanism 3700 can be used with or be a part of any of the drug delivery devices described herein.

As shown in FIG. 37, the needle insertion mechanism 3700 can include a first component 3702 and a second component 3704. The first and second components 3702 and 3704 can be coupled to a track 3710. The first and second components 3702 and 3704 can be positioned on top of the track 3710 and can slide back and forth along the track 3710.

The first and second components 3702 and 3704 can be coupled to a needle or tubing 3706. The needle 3706 can be a portion of the needle conduit 206. The needle 3706 can be routed through the first and second components 3702 and 3704. A second needle or cannula 3708 can be coupled to the first component 3702. The second needle or cannula 3708 can also be a part of the needle conduit 206. The second needle or cannula 3708 can be a soft needle or cannula and can be formed from a soft plastic material.

As shown in FIG. 37, the needle 3706 can be positioned within the cannula 3708. Together, the needle 3706 and the cannula 3708 can represent or be referred to as a transcutaneous access component. The track 3710 can be coupled to an interior portion of a bottom portion of a drug delivery device (e.g., the lower portion 104 of the drug delivery device 100).

When the needle insertion mechanism 3700 is activated, the first and second components 3702 and 3704 can slide forward, driving the cannula 3708 and the needle 3706 forward. When driven forward, the needle 3706 can be inserted into the patient. The second component 3704 can subsequently slide back, retracting the needle 3706. The first component 3702 can remain slid forward, leaving the cannula 3708 inside of the patient. The end of the needle 3706 that accesses the patient can be a hard or sharp portion of the needle 3706. When the needle 3706 is retracted, only the soft needle or cannula 3708 can remain inside of the patient. The soft needle 3704 can be coupled to the hard needle 3706 and/or the needle conduit 206, thereby providing a complete fluid path from the primary drug container of a drug delivery device to the patient.

The end of the cannula 3708 can correspond to the protrusion 502 and/or the protrusion 1102. The end of the cannula 3708 can remain inside of the drug delivery device prior to activation. The hard needle 3706 can be retracted back inside of the drug delivery device after providing access to the patient. The portion of the hard needle 3706 that extends from the second component 3704 can be relatively softer than a portion of the needle 3706 extending from the first component 3702. In various embodiments, the hard needle 3706 and the cannula 3708 can be part of the needle conduit 1514.

Figure 38:
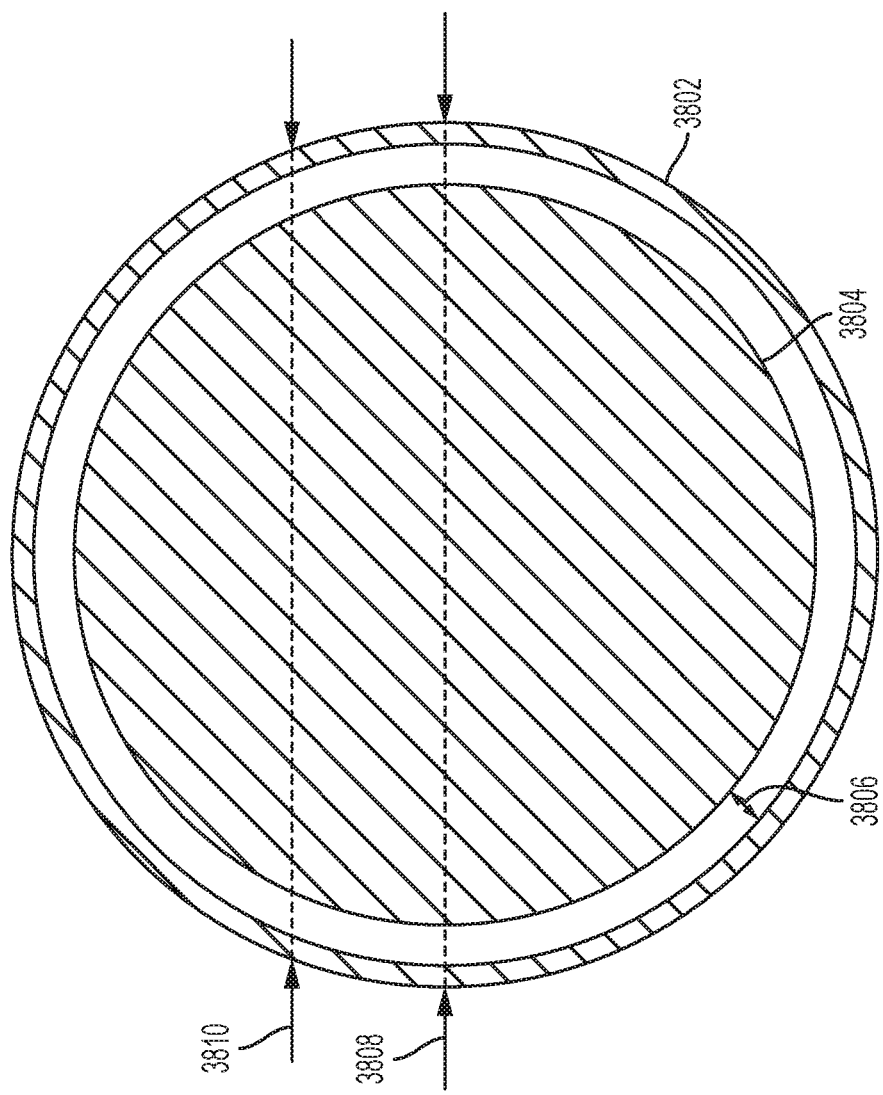
FIG. 38 illustrates an exemplary track.

FIG. 38 illustrates an exemplary embodiment of a track or guide 3802. The track 3802 can represent an implementation of the track 1514. The track 3802 can be used with any of the drug delivery systems or drive systems described herein. FIG. 38 shows a cross-sectional view of the track 3802.

As shown in FIG. 38, the track 3802 can be circular. A sphere 3804 (also shown in cross-section) can be positioned inside of the track 3802. The sphere 3804 can represent a sphere 1520.

The track 3802 can have an inner diameter that is slightly larger than a diameter of the sphere 3804, thereby allowing the sphere 3804 to move through the track 3804. A gap or distance 3806 shows a difference in the diameters of the track 3802 (e.g., inner diameter) and the sphere 3804. For purposes of illustration and explanation, the sphere 3804 is shown centered within the interior of the track 3802. During operation (e.g., movement of the sphere 3804 within the track 3802), the sphere 3804 can make contact with a portion of an inner surface of the track 3802.

The track 3802 can provide more efficient movement of the sphere 3804 than a conventional square-shaped track (i.e., a track having a square cross-sectional shape or profile). The track 3802 can enable the sphere 3804 to move through the track with less friction force to overcome than a square shaped track. In turn, the efficiency of a drive system that uses the track 3802 can be more efficient, as less force can be used to overcome frictional forces when moving the sphere 3804.

The track 3802 can be formed of any material including a plastic material or a metal material (e.g., stainless steel). The track 3802 can be formed from two or more pieces joined together at split point represented by a split line. Split line 3808 can represent a midpoint of a conventional track. The split line 3808 is positioned at an approximate halfway point of the track 3802. That is, the split line 3808 splits the track 3802 into two equal sections (e.g., an upper section and a lower section). The split line 3810 can represent a second, alternative split line of the track 3802 used in various embodiments herein. The split line 3810 can split the track 3802 at an approximately 60/40 split such that approximately 60% of the track 3802 is positioned below the split line 3810 and approximately 40% of the track is positioned above the split line 3810. The split line 3810 can represent the positioning of where the upper and lower sections of the track 3802 are joined or put together to form the circular cross-section of the track 3802 as shown in FIG. 38.

Forming the track 3802 along the split line 3810 can improve the efficiency of the track 3802 compared to forming the track along the split line 3808. The split line 3808 can introduce relatively larger frictional forces that may be required to be overcome when moving the sphere 3804 as compared to the relatively lower frictional forces introduced by forming the track 3802 along the split line 3810. As a result, the efficiency of a drive system that uses the track 3802 having the track joined at the split line 3810 can be more efficient, as less force can be used to overcome frictional forces when moving the sphere 3804.

The efficiency of the track 3802 (or a drive system using the track 3802) can also be improved when the track 3802 is formed from relatively harder materials. When the track 3802 is formed from relatively harder materials, the track 3802 may experience less deformation than when formed of relatively softer materials. Accordingly, in various embodiments, the track 3802 can be formed of relatively harder materials such as stainless steel or hard plastics to reduce deformation. The efficiency of the track 3802 (or a drive system using the track 3802) can be improved by using spheres that are lubricious. Materials such as acetyl (e.g., Delrin) or similar plastics blended with a lubricant (such as Teflon or PTFE) can be used to form the spheres and/or track 3802.

In various embodiments, the track 3802 can be formed from a single or unitary piece of material. The track 3802 can be formed from a plastic material as a single element without joining two or more pieces at a split line. For example, the track 3802 can be a plastic pipe or tube having a desired shape and curvature. In such embodiments, the track 3802 can be formed and provided without a split line. In various embodiments, the track 3802 can include one or more openings. The openings can accommodate portions of the drive systems for any of the drug delivery devices described herein.

FIG. 41 illustrates an exemplary embodiment 4100 of an alternative routing of the needle conduit 1514. The needle conduit 1514 depicted in FIG. 41 can be used with any of the drug delivery devices described herein (e.g., the drug delivery device 100).

As shown in FIG. 41, the needle conduit 1514 can be coupled to a septum 4102 of the primary drug container 1502. The needle conduit 1514 can provide a fluid path from the septum 4102 of the primary drug container 1502 to the needle insertion mechanism 1516. As shown in FIG. 41, the drive spring 1518 can apply a force to the spheres 1520. The spheres 1520 can transfer the force to the plunger 1508 to expel a liquid drug from the primary drug container 1502 through the septum 4102 and on to the needle conduit 1514.

The needle conduit 1514 can be routed along any path relative to the other components depicted in FIG. 41. The routing of the needle conduit 1514 as shown in FIG. 41 can be implemented or used with any of the drug delivery devices and/or drive systems described herein.

Overall, any of the drug delivery devices described herein can use any type of springs and any type of spring combinations for a drive spring. In general, the drive springs of the drug delivery devices described herein, including any intermediate or interstitial springs or assister springs, can be compression springs, torsion springs, or double-bodied torsion springs, or any combination thereof, and can be arranged in series, parallel, or in a combination thereof. Any of the springs described herein can be considered to be or referred to as drive springs.

Any of the drug delivery devices described herein can include any of the drive mechanisms described herein. Any of the drive mechanisms described herein can be operated to provide a stored liquid drug to a patient in a single dose or over multiple doses.

Each of the drug delivery devices and drive systems described herein can include or be implemented using a track—such as, for example the track 1524 depicted in FIG. 15—to provide a pathway or guide for the spheres. In various illustrated embodiments the track has been omitted for simplicity only. Each of the drug delivery devices and drive systems described herein can expel a stored liquid drug through the plunger sealing a first end of drug cartridge or through a septum sealing a second end of the drug cartridge as described herein. Accordingly, in various embodiments, the needle conduit can be coupled to and/or can pierce the plunger of the drug cartridge or the septum of the drug cartridge. In various embodiments providing a fluid path through the needle conduit positioned through the plunger, a primary drug container access mechanism or component can be used as described herein (e.g., positioned between the plunger and the drive mechanism or component). In various embodiments illustrating the needle conduit positioned through the plunger the primary drug container access mechanism may be omitted for purposes of illustration and simplicity only.

The following examples pertain to further embodiments:

Example 1 is a drug delivery device, comprising a drug container for storing a liquid drug, a first end of the drug container sealed by a plunger, a needle conduit coupled to the plunger, a needle insertion component coupled to the needle conduit, and a drive component coupled to the plunger, the drive component comprising a drive spring and one or more spheres.

Example 2 is an extension of Example 1 or any other example disclosed herein, wherein the plunger is movable toward a second end of the drug container by operation of the drive component to expel the liquid drug out of the drug container through the needle conduit.

Example 3 is an extension of Example 2 or any other example disclosed herein, wherein the needle conduit is arranged to enable the liquid drug to be expelled from the drug container in a direction opposite to a direction of a movement of the plunger.

Example 4 is an extension of Example 1 or any other example disclosed herein, wherein the drive spring is directly coupled to at least one of the one or more spheres.

Example 5 is an extension of Example 4 or any other example disclosed herein, wherein the drive spring comprises two or more compression springs.

Example 6 is an extension of Example 5 or any other example disclosed herein, wherein the two or more compression springs are arranged in series.

Example 7 is an extension of Example 6 or any other example disclosed herein, wherein the one or more spheres comprises a plurality of spheres, and at least one of the two or more compression springs is positioned between two adjacent spheres of the plurality of spheres.

Example 8 is an extension of Example 5 or any other example disclosed herein, wherein the two or more compression springs are arranged in parallel.

Example 9 is an extension of Example 1 or any other example disclosed herein, wherein the needle insertion component comprises a soft needle and a hard needle.

Example 10 is an extension of Example 9 or any other example disclosed herein, wherein the needle conduit is coupled to the soft needle.

Example 11 is an extension of Example 1 or any other example disclosed herein, wherein the needle conduit is directly coupled to the plunger.

Example 12 is an extension of Example 1 or any other example disclosed herein, further comprising a track providing a pathway for the one or more spheres.

Example 13 is an extension of Example 12 or any other example disclosed herein, wherein the track comprises a circular cross-sectional shape.

Example 14 is an extension of Example 13 or any other example disclosed herein, wherein the drive spring and the one or more spheres are positioned inside of the track.

Example 15 is an extension of Example 14 or any other example disclosed herein, wherein the track comprises stainless steel.

Example 16 is an extension of Example 1 or any other example disclosed herein, further comprising a drug container access component positioned between the plunger and a first sphere of the one or more spheres of the drive component.

Example 17 is an extension of Example 16 or any other example disclosed herein, wherein the drug container access component maintains an end of the needle conduit within the plunger when the drug delivery device is in an idle state.

Example 18 is an extension of Example 17 or any other example disclosed herein, wherein the drug container access component is configured to drive the end of the needle conduit through the plunger to couple the end of the needle conduit to the liquid drug when the drug delivery device is in an activated state.

Example 19 is an extension of Example 18 or any other example disclosed herein, wherein the drug container access component further comprises a needle pilot component positioned adjacent to the plunger, a pusher plate component positioned adjacent to the first sphere, and a spacer spring positioned between the needle pilot component and the pusher plate component.

Example 20 is an extension of Example 19 or any other example disclosed herein, wherein the spacer spring is configured to be in an expanded configuration when the drug delivery device is in the idle state to thereby maintain a space between the needle pilot component and the pusher plate component.

Example 21 is an extension of Example 20 or any other example disclosed herein, wherein the spacer spring is configured to be in a compressed configuration when the drug delivery device is in the activated state.

Example 22 is an extension of Example 21 or any other example disclosed herein, wherein when the drug delivery device is in the activated state, the first sphere applies a force on the pusher plate component to compress the spacer spring against the needle pilot component.

Example 23 is an extension of Example 22 or any other example disclosed herein, wherein the force applied by the first sphere drives the end of the needle conduit through the plunger by driving the needle pilot component toward the plunger.

Example 24 is an extension of Example 1 or any other example disclosed herein, wherein the drug container comprises an International Organization for Standardization (ISO) standardized cartridge.

Example 25 a method for delivering a liquid drug stored in a drug container of a drug delivery device to a patient, comprising activating the drug delivery device, accessing the patient with a needle insertion component of the drug delivery device, accessing the liquid drug in the drug container with a needle conduit extending through a plunger sealing a first end of the drug container, and driving the plunger toward a second end of the drug container to expel the liquid drug through the needle conduit for delivery to the patient through the needle insertion component.

Example 26 is an extension of Example 25 or any other example disclosed herein, wherein activating comprises receiving a patient input.

Example 27 is an extension of Example 25 or any other example disclosed herein, wherein accessing the patient comprises piercing the patient with a hard needle and a soft needle, retracting the hard needle, and maintaining the soft needle in the patient.

Example 28 is an extension of Example 25 or any other example disclosed herein, wherein accessing the liquid drug comprises piercing the plunger with an end of the needle conduit to couple the needle conduit to the liquid drug.

Example 29 is an extension of Example 25 or any other example disclosed herein, wherein driving the plunger comprises providing a force using one or more compression drive springs and applying the force to the plunger using one or more spheres.

Example 30 is an extension of Example 25 or any other example disclosed herein, further comprising expelling the liquid drug from the drug container through the first end of the drug container.

Example 31 is a drug delivery device, comprising a drug container for storing a liquid drug, a first end of the drug container sealed by a septum and second end of the plunger sealed by a plunger, a needle conduit coupled to the liquid drug, a needle insertion component coupled to the needle conduit, and a drive component coupled to the plunger, the drive component comprising one or more spheres.

Example 32 is an extension of Example 31 or any other example disclosed herein, wherein the drug container comprises an International Organization for Standardization (ISO) standardized cartridge.

Example 33 is an extension of Example 31 or any other example disclosed herein, wherein the plunger is movable toward a first end of the drug container by operation of the drive component to expel the liquid drug out of the drug container through the needle conduit.

Example 34 is an extension of Example 33 or any other example disclosed herein, wherein the needle conduit is coupled to the liquid drug through the septum.

Example 35 is an extension of Example 34 or any other example disclosed herein, wherein the needle conduit is arranged to enable the liquid drug to be expelled from the drug container in a direction corresponding to a direction of a movement of the plunger.

Example 36 is an extension of Example 33 or any other example disclosed herein, wherein the needle conduit is coupled to the liquid drug through the plunger.

Example 37 is an extension of Example 36 or any other example disclosed herein, wherein the needle conduit is arranged to enable the liquid drug to be expelled from the drug container in a direction opposite to a direction of a movement of the plunger.

Example 38 is an extension of Example 31 or any other example disclosed herein, wherein the one or more spheres comprises a plurality of spheres, wherein the drive component comprises two or more compressions springs, and at least one of the two or more compression springs is positioned between two adjacent spheres of the plurality of spheres.

Example 39 is an extension of Example 31 or any other example disclosed herein, wherein the drive component further comprises a drive spring.

Example 40 is an extension of Example 39 or any other example disclosed herein, wherein the drive spring is coupled to a sphere of the one or more spheres positioned furthest from the plunger.

Example 41 is an extension of Example 40 or any other example disclosed herein, wherein the drive spring comprises two or more compression springs.

Example 42 is an extension of Example 41 or any other example disclosed herein, wherein the two or more compression springs are arranged in series.

Example 43 is an extension of Example 41 or any other example disclosed herein, wherein the two or more compression springs are arranged in parallel.

Example 44 is an extension of Example 39 or any other example disclosed herein, further comprising a track providing a pathway for the spheres.

Example 45 is an extension of Example 44 or any other example disclosed herein, the track having a circular cross-sectional shape.

Example 46 is an extension of Example 45 or any other example disclosed herein, wherein the drive spring and the one or more spheres are positioned inside of the track.

Example 47 is an extension of Example 31 or any other example disclosed herein, the drive component further comprising a torsion spring.

Example 48 is an extension of Example 47 or any other example disclosed herein, the torsion spring comprising a double-bodied torsion spring.

Example 49 is an extension of Example 48 or any other example disclosed herein, wherein an arm of the double-bodied torsion spring is coupled to a sphere of the one or more spheres positioned furthest away from the plunger.

Example 50 is an extension of Example 49 or any other example disclosed herein, further comprising a track for containing the spheres.

Example 51 is an extension of Example 50 or any other example disclosed herein, wherein the track comprises a circular cross-sectional shape.

Example 52 is an extension of Example 51 or any other example disclosed herein, wherein the track comprising an opening positioned adjacent to the double-bodied torsion spring to allow the arm to rotate within the track.

Example 53 is an extension of Example 31 or any other example disclosed herein, the drive component further comprising two or more torsion springs.

Example 54 is an extension of Example 53 or any other example disclosed herein, the two or more torsion springs arranged in series.

Example 55 is an extension of Example 53 or any other example disclosed herein, the two or more torsion springs arranged in parallel.

Example 56 is a method for delivering a liquid drug stored in a drug container of a drug delivery device to a patient, comprising activating the drug delivery device, accessing the patient with a needle insertion component of the drug delivery device, accessing the liquid drug in the drug container with a needle conduit, and driving a plunger sealing a first end of the drug container toward a second end of the drug container to expel the liquid drug through the needle conduit for delivery to the patient through the needle insertion component.

Example 57 is an extension of Example 56 or any other example disclosed herein, wherein activating comprises receiving a patient input.

Example 58 is an extension of Example 56 or any other example disclosed herein, wherein accessing the liquid drug comprises piercing the plunger with an end of the needle conduit to couple the needle conduit to the liquid drug.

Example 59 is an extension of Example 58 or any other example disclosed herein, wherein piercing the plunger comprising applying a force to a needle pilot component coupled to the plunger to drive the needle pilot component toward the plunger, the needle pilot component housing the needle conduit.

Example 60 is an extension of Example 59 or any other example disclosed herein, further comprising compressing a spacer spring coupled to the needle pilot component to apply the force to the needle pilot component.

Example 61 is an extension of Example 60 or any other example disclosed herein, further comprising compressing the spacer spring by driving a pusher plate coupled to the spacer spring toward the spacer spring.

Example 62 is an extension of Example 56 or any other example disclosed herein, wherein accessing the liquid drug comprises piercing a septum sealing the second end of the drug container with the needle conduit to couple the needle conduit to the liquid drug.

Example 63 is an extension of Example 56 or any other example disclosed herein, wherein driving the plunger comprises providing a force using one or more compression drive springs and applying the force to the plunger through one or more spheres.

Example 64 is an extension of Example 56 or any other example disclosed herein, wherein driving the plunger comprises providing a force using a torsion spring and applying the force to the plunger through one or more spheres.

The following additional examples pertain to further embodiments:

Example 1 is a drug delivery device configured to deliver a liquid drug to a patient over two or more doses, comprising a drug container configured to store the liquid drug, a first end of the drug container sealed by a plunger, a needle conduit coupled to the plunger, a needle insertion component coupled to the needle conduit, and a drive component coupled to the plunger, the drive component comprising a dosing wheel and a plurality of spheres.

Example 2 is an extension of Example 1 or any other example disclosed herein, wherein the dosing wheel comprises a hub and a plurality of radially extending arms.

Example 3 is an extension of Example 2 or any other example disclosed herein, wherein one or more of the plurality of radially extending arms are positioned between adjacent spheres of the plurality of spheres.

Example 4 is an extension of Example 3 or any other example disclosed herein, wherein a rotation of the dosing wheel in a first direction advances the plurality of spheres toward the plunger.

Example 5 is an extension of Example 4 or any other example disclosed herein, wherein the plurality of spheres are configured to apply a force to the plunger to move the plunger toward a second end of the drug container to expel the liquid drug out of the drug container through the needle conduit.

Example 6 is an extension of Example 5 or any other example disclosed herein, wherein a predetermined amount of the rotation of the dosing wheel causes a predetermined amount of the liquid drug expelled from the drug container.

Example 7 is an extension of Example 5 or any other example disclosed herein, wherein the dosing wheel is configured such that stopping the rotation of the dosing wheel stops the liquid drug from being expelled from the drug container and restarting the rotation of the dosing wheel restarts the liquid drug being expelled from the drug container.

Example 8 is an extension of Example 4 or any other example disclosed herein, wherein the rotation of the dosing wheel is controllable by user input.

Example 9 is an extension of Example 4 or any other example disclosed herein, further comprising a controller, wherein the rotation of the dosing wheel is controllable by the controller.

Example 10 is an extension of Example 4 or any other example disclosed herein, wherein the drive component further comprises one or more compression springs.

Example 11 is an extension of Example 10 or any other example disclosed herein, wherein the one or more compressions springs are configured to apply a force to the plurality of spheres to move the plunger toward the second end of the drug container.

Example 12 is an extension of Example 5 or any other example disclosed herein, wherein the needle conduit is arranged to enable the liquid drug to be expelled from the drug container in a direction opposite to a direction of a movement of the plunger.

Example 13 is an extension of Example 1 or any other example disclosed herein, wherein the drug container comprises an International Organization for Standardization (ISO) standardized cartridge.

Example 14 is an extension of Example 1 or any other example disclosed herein, wherein the needle insertion component comprises a soft needle and a hard needle.

Example 15 is an extension of Example 14 or any other example disclosed herein, wherein the needle conduit is coupled to the soft needle.

Example 16 a method for delivering a liquid drug stored in a drug container of a drug delivery device to a user over two or more doses, comprising activating the drug delivery device, accessing the user with a needle component of the drug delivery device, coupling the liquid drug to a needle conduit, the needle conduit coupled to the needle component, driving a plurality of spheres toward a plunger sealing a first end of the drug container, and rotating a dosing wheel having one or more radially extending arms positioned between one or more spheres of the plurality of spheres to regulate a movement of the plurality of spheres toward the plunger to expel the liquid drug through the needle conduit for delivery to the user.

Example 17 is an extension of Example 16 or any other example disclosed herein, wherein rotating the dosing wheel comprises regulating the movement of the plurality of spheres toward a second end of the drug container.

Example 18 is an extension of Example 16 or any other example disclosed herein, further comprising coupling the liquid drug to the needle conduit through the plunger.

Example 19 is an extension of Example 16 or any other example disclosed herein, wherein driving further comprises driving the plurality of spheres with one or more compression drive springs.

Example 20 is an extension of Example 16 or any other example disclosed herein, wherein activating further comprises receiving a user input.

Example 21 is a drug delivery device for delivering a liquid drug to a patient over two or more doses, comprising a drug container for storing a liquid drug, a first end of the drug container sealed by a septum and second end of the plunger sealed by a plunger, a needle conduit coupled to the liquid drug, a needle insertion component coupled to the needle conduit, and a drive component coupled to the plunger, the drive component comprising one or more spheres and a rotatable arm.

Example 22 is an extension of Example 21 or any other example disclosed herein, wherein the one or more spheres are coupled to the plunger.

Example 23 is an extension of Example 22 or any other example disclosed herein, wherein the rotatable arm is coupled to a first sphere of the one or more spheres positioned furthest from the plunger.

Example 24 is an extension of Example 23 or any other example disclosed herein, wherein the plunger is movable toward the first end of the drug container by rotation of the rotatable arm to expel the liquid drug out of the drug container through the needle conduit.

Example 25 is an extension of Example 24 or any other example disclosed herein, wherein the needle conduit is arranged to enable the liquid drug to be expelled from the drug container in a direction opposite to a direction of a movement of the plunger.

Example 26 is an extension of Example 24 or any other example disclosed herein, wherein the needle conduit is arranged to enable the liquid drug to be expelled from the drug container in a direction corresponding to a direction of a movement of the plunger.

Example 27 is an extension of Example 24 or any other example disclosed herein, wherein a predetermined amount of the rotation of the rotatable arm causes a predetermined amount of the liquid drug to expel from the drug container.

Example 28 is an extension of Example 27 or any other example disclosed herein, wherein the rotatable arm is configured such that stopping the rotation of the rotatable arm stops the liquid drug from being expelled from the drug container and restarting the rotation of the rotatable arm restarts the liquid drug being expelled from the drug container.

Example 29 is an extension of Example 24 or any other example disclosed herein, wherein the rotation of the rotatable arm is controllable by user input.

Example 30 is an extension of Example 24 or any other example disclosed herein, further comprising a controller, wherein the rotation of the rotatable arm is controllable by the controller.

Example 31 is an extension of Example 21 or any other example disclosed herein, wherein the rotatable arm comprises an arm of a torsion spring.

Example 32 is a method for delivering a liquid drug stored in a drug container of a drug delivery device to a user over two or more doses, comprising activating the drug delivery device, accessing the user with a needle component of the drug delivery device, coupling the liquid drug to a needle conduit, the needle conduit coupled to the needle component, driving a plurality of spheres toward a plunger sealing a first end of the drug container, and rotating a rotatable arm coupled to the plurality of spheres to regulate a movement of the plurality of spheres toward the plunger to expel the liquid drug through the needle conduit for delivery to the user.

Example 33 is an extension of Example 32 or any other example disclosed herein, further comprising rotating the rotatable arm a predetermined amount to cause a predetermined amount of the liquid drug to expel from the drug container.

Example 34 is a drug delivery device for delivering a liquid drug to a patient over two or more doses, comprising a drug container for storing a liquid drug, a first end of the drug container sealed by a septum and second end of the plunger sealed by a plunger, a needle conduit coupled to the liquid drug, a needle insertion component coupled to the needle conduit, and a drive component coupled to the plunger, the drive component comprising a flexible drive component and a rotatable nut.

Example 35 is an extension of Example 34 or any other example disclosed herein, wherein the rotatable nut is coupled to the second end of the drug container.

Example 36 is an extension of Example 35 or any other example disclosed herein, wherein the flexible drive component is coupled to the plunger through the rotatable nut.

Example 37 is an extension of Example 36 or any other example disclosed herein, wherein the plunger is movable toward the first end of the drug container by rotation of the rotatable nut to expel the liquid drug out of the drug container through the needle conduit.

Example 38 is an extension of Example 37 or any other example disclosed herein, wherein the rotation of the rotatable nut is configured to drive the flexible drive component towards the plunger to apply a force to the plunger to move the plunger toward the first end of the drug container.

Example 39 is an extension of Example 37 or any other example disclosed herein, wherein the needle conduit is arranged to enable the liquid drug to be expelled from the drug container in a direction opposite to a direction of a movement of the plunger.

Example 40 is an extension of Example 37 or any other example disclosed herein, wherein the needle conduit is arranged to enable the liquid drug to be expelled from the drug container in a direction corresponding to a direction of a movement of the plunger.

Example 41 is an extension of Example 37 or any other example disclosed herein, wherein a predetermined amount of the rotation of the rotatable nut causes a predetermined amount of the liquid drug to expel from the drug container.

Example 42 is an extension of Example 41 or any other example disclosed herein, wherein the rotatable nut is configured such that stopping the rotation of the rotatable nut stops the liquid drug from being expelled from the drug container and restarting the rotation of the rotatable nut restarts the liquid drug being expelled from the drug container.

Example 43 is an extension of Example 36 or any other example disclosed herein, wherein the rotation of the rotatable nut is controllable by user input.

Example 44 is an extension of Example 36 or any other example disclosed herein, further comprising a controller, wherein the rotation of the rotatable arm is controllable by the controller.

Example 45 is an extension of Example 34 or any other example disclosed herein, wherein the flexible drive component comprises a compression spring.

Example 46 is a method for delivering a liquid drug stored in a drug container of a drug delivery device to a user over two or more doses, comprising activating the drug delivery device, accessing the user with a needle component of the drug delivery device, coupling the liquid drug to a needle conduit, the needle conduit coupled to the needle component, coupling a rotatable component to a flexible component, the rotatable component coupled to a first end of the drug container sealed by a plunger, coupling the flexible component to the plunger through the rotatable component, and rotating the rotatable component to drive the flexible component toward the plunger to move the plunger toward a second end of the drug container to expel the liquid drug through the needle conduit for delivery to the user.

Example 46 is an extension of Example 46 or any other example disclosed herein, further comprising rotating the rotatable component a predetermined amount to cause a predetermined amount of the liquid drug to expel from the drug container.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A drug delivery device, comprising:
a housing, containing:
a container configured to store a liquid drug;
a needle insertion mechanism configured, upon activation, to extend a hard needle with a soft needle into a user and retract the hard needle leaving the soft needle in the user;
a drive component configured to engage a plunger to expel a portion of the liquid drug from the container;
a needle conduit coupled to the container and configured to transfer the expelled portion of the liquid drug from the container to the needle insertion mechanism;
an activation mechanism including a first lockout and a second lockout, wherein the first lockout is positioned opposite the second lockout and the first lockout and the second lockout are configured to prevent the drive component from engaging the plunger until actuation of the activation mechanism;
a first user interaction component located on a first side of the housing, wherein the first user interaction component is configured, in response to engagement by the user, to release the first lockout of the activation mechanism; and
a second user interaction component located on a second side of the housing, the second user interaction component configured, in response to engagement by the user, to release the second lockout of the activation mechanism, wherein, upon engagement of each of the first user interaction component and the second user interaction component, the activation mechanism is actuated and the liquid drug is expelled.

2. The drug delivery device of claim 1, wherein the first user interaction component and the second user interaction component are configured to initiate delivery of the liquid drug when the first user interaction component and second user interaction component are activated in series.

3. The drug delivery device of claim 1, wherein the first user interaction component and second user interaction component are configured to initiate delivery of the liquid drug when the first user interaction component and the second user interaction component are activated simultaneously.

4. The drug delivery device of claim 1, wherein the first user interaction component and the second user interaction component each comprise a push button.

5. The drug delivery device of claim 1, wherein the drug delivery device is a wearable drug delivery device.

6. The drug delivery device of claim 5, further comprising an adhesive component positioned on the drug delivery device configured to attach to the user.

7. The drug delivery device of claim 6, wherein the adhesive component comprises at least one of a strip or pad positioned on a bottom surface of the drug delivery device.

8. The drug delivery device of claim 1, wherein the needle insertion mechanism is further configured to:
retract the hard needle inside of the drug delivery device after the soft needle is coupled for drug delivery.

9. The drug delivery device of claim 1, wherein the hard needle and the soft needle extend from the drug delivery device at an angle.

10. A drug delivery device, comprising:
a housing, containing:
a container configured to store a liquid drug;
a needle insertion mechanism including a hard needle and a soft needle maintained prior to activation within the drug delivery device and configured, upon activation, to extend the hard needle with the soft needle into a user and retract the hard needle leaving the soft needle in the user;
a drive component, including a plurality of spheres configured to engage a plunger to expel a portion of the liquid drug from the container;
a needle conduit coupled to the container and configured to transfer the expelled portion of the liquid drug from the container to the needle insertion mechanism;
an activation mechanism including a first lockout and a second lockout, wherein the first lockout is positioned opposite the second lockout and a first sphere of the plurality of spheres is prevented from engaging the plunger by the first lockout and the second lockout until actuation of the activation mechanism;
a movable first user interaction component located on a first side of the housing, wherein the movable first user interaction component is configured, in response to engagement by the user, to release the first lockout of the activation mechanism; and
a movable second user interaction component, located on a second side of the housing, the movable second user interaction component configured, in response to engagement by the user, to actuate a push-pull rod of the activation mechanism that releases the second lockout of the activation mechanism, wherein, upon engagement of each of the movable first user interaction component and the movable second user interaction component, the activation mechanism is actuated and the first sphere of the plurality of spheres engages the plunger to expel the liquid drug.

11. The drug delivery device of claim 10, wherein the first lockout comprises either:
a set of balls positioned on a track or tray and in contact with the first sphere of the plurality of spheres, or
a rod configured to move in response to the moveable first user interaction component.

12. The drug delivery device of claim 11, wherein the movable first user interaction component is configured to move an arm of the activation mechanism that allows the set of balls to move away from the first sphere of the plurality of spheres.

13. The drug delivery device of claim 10, wherein the second lockout comprises:
a first ball positioned against the first sphere of the plurality of spheres, wherein the first ball is configured to move away from the first sphere of the plurality of spheres in response to the engagement of the movable second user interaction component.

14. The drug delivery device of claim 10, wherein the movable first user interaction component and the movable second user interaction component are configured to initiate delivery of the liquid drug when the movable first user interaction component and the movable second user interaction component are activated in series.

15. The drug delivery device of claim 10, wherein the movable first user interaction component and the movable second user interaction component are configured to initiate delivery of the liquid drug when the movable first user interaction component and the movable second user interaction component are activated simultaneously.

16. The drug delivery device of claim 10, wherein the drug delivery device is a wearable drug delivery device.

17. The drug delivery device of claim 10, further comprising an adhesive component positioned on the drug delivery device configured to attach to the user.

18. The drug delivery device of claim 17, wherein the adhesive component comprises at least one of a strip or pad positioned on a bottom surface of the drug delivery device.

19. The drug delivery device of claim 10, wherein the needle insertion mechanism is further configured to:
   retract the hard needle inside of the drug delivery device after the soft needle is coupled for drug delivery.

20. The drug delivery device of claim 10, wherein the hard needle and the soft needle extend from the drug delivery device at an angle.

* * * * *